United States Patent
Reinke et al.

(10) Patent No.: US 11,912,874 B2
(45) Date of Patent: Feb. 27, 2024

(54) CRUDE STEROL AS AN ADDITIVE IN ASPHALT BINDER

(71) Applicants: A.L.M. Holding Co., Onalaska, WI (US); Ergon Asphalt & Emulsions, Inc., Jackson, MS (US)

(72) Inventors: Gerald H. Reinke, La Crosse, WI (US); Gaylon L. Baumgardner, Arkadelphia, AR (US); Andrew Hanz, La Crosse, WI (US)

(73) Assignees: A.L.M. Holding Company, Onalaska, WI (US); Ergon Asphalt & Emulsions, Inc., Jackson, MS (US)

( * ) Notice: Subject to any disclaimer, the term of this patent is extended or adjusted under 35 U.S.C. 154(b) by 1151 days.

(21) Appl. No.: 16/308,408

(22) PCT Filed: Dec. 5, 2016

(86) PCT No.: PCT/US2016/064961
§ 371 (c)(1),
(2) Date: Dec. 7, 2018

(87) PCT Pub. No.: WO2017/213693
PCT Pub. Date: Dec. 14, 2017

(65) Prior Publication Data
US 2019/0153229 A1    May 23, 2019

Related U.S. Application Data

(63) Continuation-in-part of application No. PCT/US2016/037077, filed on Jun. 10, 2016.
(Continued)

(51) Int. Cl.
*C08L 95/00* (2006.01)
*C08K 5/05* (2006.01)
(Continued)

(52) U.S. Cl.
CPC .............. *C08L 95/00* (2013.01); *C04B 18/16* (2013.01); *C04B 26/26* (2013.01); *C08K 5/05* (2013.01);
(Continued)

(58) Field of Classification Search
CPC ....................................... C08L 95/00
See application file for complete search history.

(56) References Cited

U.S. PATENT DOCUMENTS

| | | |
|---|---|---|
| 1,112,492 A | 10/1914 | Turner |
| 2,280,843 A | 4/1942 | Oliver et al. |

(Continued)

FOREIGN PATENT DOCUMENTS

| | | |
|---|---|---|
| CA | 3 026 997 A1 | 12/2017 |
| CL | 2011002791 A1 | 4/2012 |

(Continued)

OTHER PUBLICATIONS

ASTM D6521-13 (2013) "Standard Practice for Accelerated Aging of Asphalt Binder Using a Pressurized Aging Vessel (PAV)", ASTM International, 6 pages.
(Continued)

*Primary Examiner* — Alexandra M Moore
(74) *Attorney, Agent, or Firm* — Kagan Binder, PLLC

(57) ABSTRACT

Disclosed are binders and methods for making such binders with crude sterols. The crude sterols improve various rheological properties of the binders. The disclosure provides a method for slowing the aging rate of aged asphalt binder comprising adding a crude sterol to an asphalt binder, wherein the asphalt binder comprises both virgin asphalt binder, and reclaimed asphalt binder material comprising asphalt pavement (RAP), asphalt shingles (RAS) or combinations of RAP and RAS.

16 Claims, 24 Drawing Sheets

Related U.S. Application Data

(60) Provisional application No. 62/385,899, filed on Sep. 9, 2016, provisional application No. 62/385,905, filed on Sep. 9, 2016.

(51) Int. Cl.
  G01N 33/42 (2006.01)
  C04B 26/26 (2006.01)
  E01C 1/00 (2006.01)
  C04B 18/16 (2023.01)
  G01Q 60/24 (2010.01)
  E01C 7/18 (2006.01)

(52) U.S. Cl.
  CPC .............. *E01C 1/00* (2013.01); *G01N 33/42* (2013.01); *C08K 2201/00* (2013.01); *C08L 2555/10* (2013.01); *C08L 2555/22* (2013.01); *C08L 2555/34* (2013.01); *C08L 2555/52* (2013.01); *C08L 2555/60* (2013.01); *C08L 2555/64* (2013.01); *C08L 2555/74* (2013.01); *E01C 7/18* (2013.01); *G01Q 60/24* (2013.01)

(56) References Cited

U.S. PATENT DOCUMENTS

| | | | |
|---|---|---|---|
| 2,286,244 A | | 6/1942 | Whitacre et al. |
| 2,392,863 A | * | 1/1946 | Rudd ............... C08L 95/00 106/269 |
| 2,411,634 A | | 11/1946 | Pearson |
| 2,585,336 A | | 2/1952 | McCoy |
| 2,715,638 A | | 8/1955 | Albrecht et al. |
| 2,728,682 A | | 12/1955 | Kalinowski et al. |
| 2,793,138 A | | 5/1957 | Wilkinson |
| 2,860,067 A | | 11/1958 | Crews et al. |
| 3,032,507 A | | 5/1962 | Wright |
| 3,044,373 A | | 7/1962 | Sommer |
| 3,556,827 A | | 1/1971 | McConnaughay |
| 3,691,211 A | * | 9/1972 | Julian ............... C07J 9/00 552/545 |
| 3,926,936 A | | 12/1975 | Lehtinen |
| 3,951,676 A | | 4/1976 | Elste, Jr. |
| 4,044,031 A | | 8/1977 | Johnansson et al. |
| 4,549,834 A | | 10/1985 | Allen |
| 4,874,432 A | | 10/1989 | Kriech et al. |
| 5,234,494 A | | 8/1993 | Sawatzky et al. |
| 5,437,717 A | | 8/1995 | Doyle et al. |
| 5,473,000 A | | 12/1995 | Pinomaa |
| 5,496,400 A | | 3/1996 | Doyle et al. |
| 6,057,462 A | | 5/2000 | Robinson et al. |
| 6,770,127 B2 | | 8/2004 | Kriech et al. |
| 6,987,207 B1 | | 1/2006 | Ronyak |
| 7,448,825 B2 | | 11/2008 | Kasahara et al. |
| 7,575,767 B2 | | 8/2009 | May et al. |
| 7,811,372 B2 | | 10/2010 | Nigen-Chaidron et al. |
| 8,513,338 B2 | | 8/2013 | Rodrigues |
| 8,696,806 B2 | | 4/2014 | Williams et al. |
| 8,741,052 B2 | | 6/2014 | Naidoo et al. |
| 8,821,064 B1 | | 9/2014 | Morris et al. |
| 9,481,794 B2 | | 11/2016 | Cox |
| 9,828,506 B2 | | 11/2017 | Grady et al. |
| 9,994,485 B2 | | 6/2018 | Warner et al. |
| 10,030,145 B2 | | 7/2018 | Severance et al. |
| 10,077,356 B2 | | 9/2018 | Fini |
| 10,167,390 B2 | | 1/2019 | Cox |
| 10,669,202 B2 | | 6/2020 | Reinke et al. |
| 10,793,720 B2 | | 10/2020 | Puchalski et al. |
| 10,961,395 B2 | | 3/2021 | Williams et al. |
| 11,097,981 B2 | | 8/2021 | Reinke et al. |
| 11,124,926 B2 | | 9/2021 | Fennell et al. |
| 11,168,214 B2 | | 11/2021 | Reinke et al. |
| 2003/0087789 A1 | | 5/2003 | Scheffler |
| 2003/0128467 A1 | | 7/2003 | Blair et al. |
| 2003/0144536 A1 | | 7/2003 | Sonnier et al. |
| 2007/0122235 A1 | | 5/2007 | Kasahara et al. |
| 2007/0151480 A1 | | 7/2007 | Bloom et al. |
| 2010/0170417 A1 | | 7/2010 | Naidoo et al. |
| 2010/0190892 A1 | | 7/2010 | Binkley |
| 2010/0227954 A1 | | 9/2010 | Naidoo et al. |
| 2010/0305342 A1 | | 12/2010 | Wong et al. |
| 2010/0319577 A1 | | 12/2010 | Naidoo et al. |
| 2011/0020519 A1 | | 1/2011 | Bowman et al. |
| 2012/0060722 A1 | | 3/2012 | Montpeyroux et al. |
| 2014/0234027 A1 | | 8/2014 | Morris |
| 2014/0338565 A1 | | 11/2014 | Severance et al. |
| 2015/0087753 A1 | | 3/2015 | Koleas et al. |
| 2015/0329702 A1 | | 11/2015 | Hwang et al. |
| 2016/0122507 A1 | | 5/2016 | Cox |
| 2016/0160453 A1 | | 6/2016 | Donelson |
| 2016/0304718 A1 | | 10/2016 | Bindschedler et al. |
| 2016/0362338 A1 | | 12/2016 | Reinke et al. |
| 2017/0370899 A1 | | 12/2017 | Porot et al. |
| 2018/0171146 A1 | | 6/2018 | Allen et al. |
| 2018/0209102 A1 | | 7/2018 | Baumgardner et al. |
| 2018/0215919 A1 | | 8/2018 | Reinke et al. |
| 2019/0152850 A1 | | 5/2019 | Warner et al. |
| 2019/0153229 A1 | | 5/2019 | Reinke et al. |
| 2019/0265221 A1 | | 8/2019 | Reinke et al. |
| 2020/0207944 A1 | | 7/2020 | Reinke et al. |
| 2020/0277497 A1 | | 9/2020 | Reinke et al. |
| 2021/0017386 A1 | | 1/2021 | Reinke et al. |
| 2021/0380477 A1 | | 12/2021 | Reinke et al. |
| 2022/0195193 A1 | | 6/2022 | Reinke et al. |
| 2022/0251387 A1 | | 8/2022 | Reinke et al. |
| 2023/0257303 A1 | | 8/2023 | Reinke et al. |

FOREIGN PATENT DOCUMENTS

| | | | |
|---|---|---|---|
| CL | 2014002871 A1 | | 7/2015 |
| CN | 103387749 A | | 11/2013 |
| CN | 104245850 A | | 12/2014 |
| CN | 104364318 A | | 2/2015 |
| CN | 104629392 A | | 5/2015 |
| CN | 110799597 A | | 2/2020 |
| EP | 1 728 831 A1 | | 12/2006 |
| GB | 233430 A | * | 5/1925 |
| GB | 575484 A | | 2/1946 |
| JP | H10-81827 A | | 3/1998 |
| JP | H11-60960 A | | 3/1999 |
| JP | 2005-154465 A | | 6/2005 |
| JP | 2012-093108 A | | 5/2012 |
| JP | 2016-509611 A | | 3/2016 |
| WO | 01/072315 A1 | | 10/2001 |
| WO | 2004/016336 A1 | | 2/2004 |
| WO | 2010/110651 A1 | | 9/2010 |
| WO | 2010/128105 A1 | | 11/2010 |
| WO | 2013/090283 A1 | | 6/2013 |
| WO | 2013/163463 A1 | | 10/2013 |
| WO | 2013/163467 A1 | | 10/2013 |
| WO | 2014/047462 A1 | | 3/2014 |
| WO | 2015/070180 A1 | | 5/2015 |
| WO | 2016/065270 A1 | | 4/2016 |
| WO | 2016/073442 A1 | | 5/2016 |
| WO | 2017/011747 A1 | | 1/2017 |
| WO | 2017/027096 A2 | | 2/2017 |
| WO | 2017/213692 A1 | | 12/2017 |
| WO | 2017/213693 A1 | | 12/2017 |
| WO | 2018/031540 A1 | | 2/2018 |
| WO | 2018/144731 A1 | | 8/2018 |
| WO | 2019/023172 A1 | | 1/2019 |
| WO | 2019/079101 A1 | | 4/2019 |
| WO | 2021/011703 A1 | | 1/2021 |
| WO | 2021/011704 A1 | | 1/2021 |

OTHER PUBLICATIONS

"Material Safety Data Sheet (Aug. 8, 2013)", Sylfat.TM. DP8, Arizona Chemical Company LLC, 7 pages.

"Refining and Properties of Asphalt Binders", Asphalt Handbook, 7th Edition, 2007, 2 pages.

"Sylvaroad.TM. RP 1000 Performance Additive", Safety Data Sheet, Arizona Chemical Company LLC, Apr. 1, 2015, 7 pages.

(56) References Cited

OTHER PUBLICATIONS

"Tall Oil Fatty Acid", Ataman Kimya, retrieved on Aug. 10, 2021, 8 pages.

"Tallex Pitch", Ingevity Holdings SPRL, Safety Data Sheet, Jul. 21, 2017, 12 pages.

Allen, et al. (2013) "Microstructural Characterization of the Chemo-Mechanical Behavior of Asphalt in Terms of Aging and Fatigue Performance Properties", UMI Dissertation Publishing, Proquest LLC., 162 pages.

Anderson, et al. (1994) "Binder Characterization and Evaluation, vol. 3: Physical Characterization", SHRP-A-369, Strategic Highway Research Program, 4 pages.

Cao, et al. (2011) "Chemical Structures of Swine-Manure Chars Produced under Different Carbonization Conditions Investigated by Advanced Solid-State 13C Nuclear Magnetic Resonance (NMR) Spectroscopy ", Energy Fuels, 25:388-397.

Cox, Russell Brian "Asphalt Binders Containing a Glyceride and Fatty Acid Mixture and Methods for Making and Using Same", U.S. Appl. No. 62/074,526, filed Nov. 3, 2014, 64 pages.

Endo, Yasushi (1990) "Minor Components in Edible Fats and Oils" Oil Chemistry, 39(9):611-617 (English Abstract on p. 611).

Farrar, et al. (2012) "Thin Film Oxidative Aging and low Temperature Performance Grading using Small Plate Dynamic Shear Rheometry: An Alternative to Standard RTFO, PAV, and BBR", 5th Eurasphalt & Eurobitume Congress, 10 pages.

Fini et al. (2012) "Application of Swine Manure in Development of Bio-Adhesive", Allen D. Leman Swine Conference, p. 244.

Fini, et al. (2010) "Characterization and Application of Manure-Based Bio-Binder in Asphalt Industry", Transportation Research Board 89th Annual Meeting, 14 pages.

Fini, et al. (2011) "Chemical Characterization of Biobinder from Swine Manure: Sustainable Modifier for Asphalt Binder", Journal of Materials in Civil Engineering, 23(11): 1506-1513.

Fini, et al.(2011) "Application of Bio-Binder from Swine Manure in Asphalt Binder", Annual Meeting, 15 pages.

Hill, (2015) "The When, How and Benefits of Using Thinlays for Pavement Preservation", Equipment World, 9 pages.

International Search Report and Written Opinion for International Application No. PCT/US2018/055443, dated Jan. 31, 2019, 14 pages.

International Search Report and Written Opinion for International Application No. PCT/US2018/043387, dated Nov. 28, 2018, 17 pages.

International Search Report and Written Opinion for International Application No. PCT/US2020/042202, dated Oct. 15, 2020, 24 pages.

Jarde, et al. (2007) "Using Sterols to Detect Pig Slurry Contribution to Soil Organic Matter", Water Air Soil Pollut, 178:169-178.

Kriz, et al. (2007) "Glass Transition and Phase Stability in Asphalt Binders", Road Materials and Pavements Design, 30 pages.

Logan, R.L., (Nov. 1979) "Tall Oil Fatty Acids", Journal of American Oil Chemists Society, 56:777A-779A.

Loughrin, et al. (2006) "Free Fatty Acids and Sterols in Swine Manure", Journal of Environmental Science and Health, Part B, 41:31-42.

Mogawer, et al. (2012) "Performance Characteristics of High Rap Bio-Modified Asphalt Mixtures", Transportation Research Board 91st Annual Meeting, 16 pages.

Reinke, et al. (2017) "Investigation of Sterol Chemistry to Retard the Aging of Asphalt Binders", Transportation Research Record, 2633:127-135.

Rossi, et al. (2017) "Adhesion Promoters in Bituminous Road Materials: A Review", Applied Sciences, 7(524):1-10.

Wakefield, Amma (Aug. 15, 2018) "ΔTc: A Parameter to Monitor Asphalt Binder's Kryptonite" Asphalt, 33(2):24-27.

Yan, et al., (2011), "Recovery of Phytosterols from Waste Residue of Soybean Oil Deodorizer Distillate", Soybean-Applications and Technology, 13 pages.

Zaumanis, et al. (2014) "Evaluation of Different Recycling Agents for Restoring Aged Asphalt Binder and Performance of 100% Recycled Asphalt", Materials and Structures, 48(8):2475-2488.

International Search Report and Written Opinion of International Application No. PCT/US2018/016451, dated May 8, 2018, 18 pp.

International Search Report and Written Opinion of International Application No. PCT/US2020/042203, dated Oct. 15, 2020, 27 pp.

King et al., "Temperature Dependent Imaging of Aged Asphalt Binders using AFM," Petersen Asphalt Research Conference, Jul. 2019, 28 pp.

Reinke et al., "Retardation of Binder Aging Using Sterol Chemistry— Focused on Re-Aging Properties of Treated Binder Based on Theological & Compositional Properties for Six Treatments & Four Aging Levels," Petersen Asphalt Research Conference, Jul. 2019, 41 pp.

Faller, R., "Chapter 1.6: Sterols and Sterol Induced Phases," from UCD Biophysics 241: Membrane Biology, Mar. 2021, 4 pp.

International Search Report and Written Opinion of International Application No. PCT/US2022/026310, dated Jul. 11, 2022, 11 pp.

Anonymous: "Standard Test Method for Determining the Flexural Creep Stiffness of Asphalt Binder Using the Bending Beam Rheometer (BBR); ASTM D 6648-01", Aug. 1, 2001, pp. 1-14, Retrieved from the Internet: URL: ftp://185.72.26.245/Astm/1/Section04/ASTM0403/PDF/D6648.pdf, retrieved on Mar. 14, 2017.

Changping Sui et al., "New Technique for Measuring Low-Temperature Properties of Asphalt Binders with Small Amounts of Material", Transportation Research Record, Transportation Research Board, Washington, DC, US, vol. 2179, Dec. 1, 2010, pp. 23-28.

G.M. Rowe, "[Delta]Tc—Some Thoughts on the Historical Development," Binder ETG Meeting, Apr. 28, 2016, pp. 1-43, retrieved from the Internet: URL:https://www.asphaltpavement.org/PDFs/Engineering_ETGs/Binder_201604/13Rowe-DTc- Historical development.pdf [retrived on Mar. 22, 2017].

Amy Epps Martin et al., The Effects of Recycling Agents on Asphalt Mixtures with High RAS and RAP Binder Ratios (Project N 9-58), Mar. 1, 2015, Retrieved from the Internet: URL:http://onlinepubs.trb.org/onlinepubs/nchrp/docs/HNCHP09-58_Phl_InterimReport.pdf [retrieved on Mar. 20, 2017].

Gerald Reinke et al., "Further Investigations Into the Impact of REOB & Paraffinic Oils on the Performance of Bituminous Mixtures", Binder ETG Meeting, Apr. 9, 2015, pp. 1-92, Fall River, MA, USA, Retrieved from the Internet: URL:http://www.asphaltinstitute.org/wo-content/uploads/2015-April-Binder-ETG-04_Reinke_MTE-REOB-OTHER-PARAFFINIC-OILS-w-notes-w-crack-maps.pdf.

Geoffrey M. Rowe, "Asphalt Modification", 56th Illinois Bituminous Paving Conference, Dec. 15, 2015, pp. 1-42, Champaign, Illinois, USA, Retrieved from the Internet: URL:http://conferences.ict.illinois.edu/bituminousconference/56th Annual Presentations and Attendees/Rowe.pdf [retrieved on Mar. 20, 2017].

Anonymous, "The Use of REOB/VTAE in Asphalt (IS-235)," Apr. 13, 2016, pp. 1-92, Retrieved from the Internet: URL:http://www.asphaltinstitute.org/wp-content/uploads/IS235_REOB_VTAE_Asphaltinstitute.pdf [retrieved on Mar. 20, 2017].

E.E. McSweeney et al., "Composition of Crude Tall Oil & Fractionation Products (Chapter 2)" in "Tall Oil and Its Uses-II", Jan. 1, 1987, Pulp Chemicals Association, pp. 12-19.

B. Holmbom et al., "Compostion of Tall Oil Pitch", Journal of the American Oil Chemist's Society, vol. 55, Feb. 23, 1978, pp. 342-344, Retrieved from the Internet: URL:http:www.springerlink.com/content/j37742625p63ggtl/fulltext.pdf [retrieved on Apr. 24, 2012].

T. Verleyen et al., "Analysis of Free and Esterified Sterols in Vegetable Oils", Journal of the American Oil Chemists Society (Jaocs), vol. 79, No. 2, Feb. 1, 2002, pp. 117-122.

Hajime Takano et al., "Chemical and Biochemical Analysis Using Scanning Force Microscopy", Chemical Reviews, vol. 99, No. 10, Oct. 1, 1999, pp. 2845-2890.

R.M. Overney et al., "Friction Measurement on Phase-Separated Thin Films with a Modified Atomic Force Microscope", Nature, Nature Publishing Group, United Kingdom, vol. 359, Sep. 10, 1992, pp. 133-135.

(56) References Cited

OTHER PUBLICATIONS

Rubab et a., (2011) "Effects of Engine Oil Residues on Asphalt Cement Quality", Canadian Technical Asphalt Association Conference, 12 pages.
"B-Sitosterol from Soybeans" downloaded from http://www.mpbio.com/product.php?pid=02102886, downloaded on May 21, 2015, 2 pages.
"Digging Into Asphaltenes", Sep. 21, 2009, vol. 87, No. 38, 7 pages, downloaded from http://pubs.acs.org/cen/coverstory/87/8738cover.html, downloaded on Jun. 5, 2011.
T. Verleyen et al., "Influence of the Vegetable Oil Refining Process on Free and Esterified Sterols. J Am Oil Chem Soc", Article in Journal of the American Oil Chemists' Society, Sep. 2002, 8 pages.
Material Safety Data Sheet, Catalog No. 102886, Revision date: Apr. 26, 2006, Product Name: beta-Sitosterol Practical Grade, 5 pages.
B-Sitosterol.Powder, Supplier: MP Biomedicals, Printed from VWR Website, Date: Jun. 9, 2016, 1 page.
International Search Report and Written Opinion for International Application No. PCT/US2017/045887, dated Dec. 8, 2017, 14 pages.
Richard Cantrill, Ph.D., "Phytosterols, Phytostanols and Their Esters", 2008, 13 pages.
International Search Report and Written Opinion for International Application No. PCT/US2016/037077, dated Apr. 5, 2017, 20 pages.
International Search Report and Written Opinion for International Application No. PCT/US2016/064950, dated Apr. 19, 2017, 12 pages.
International Search Report and Written Opinion for International Application No. PCT/US2016/064961, dated Apr. 5, 2017, 23 pages.
Andrew Hanz et al., "Extended Aging of RAS Mixes with Rejuvenator", Aug. 10, 2016, Binder Expert task Group Meeting, retrieved from the Internet: URL:https://www.asphaltpavement.org/PDFs/Engineering_ETGs/Binder201609/06 Hanz Extended Aging of RAS Mixes with Rejuvenator.pdf, retrieved on Nov. 23, 2017.
Gerald Reinke et al., "Extended Aging of RAS Mixes with Rejuvenator An Update", May 4, 2017, Binder Expert task Group Meeting, retrieved from the Internet: URL:https://www.asphaltpavement.org/PDFs/Engineering_ETGs/ Binder201705/12_Reinke&Hanz_UpdateExtendedAgingofRAS.pdf, retrieved on Nov. 23, 2017.
Allen, Robert, "Structural Characterization of Micromechanical Properties in Asphalt Using Atomic Force Microscopy," Thesis, Office of Graduate Studies at Texas A&M University for a Master of Science Degree, Dec. 2010, pp. 104.
Wang et al., "Study of extraction of phytosterol from masson pine raw tall oil," Journal of Wood Science, vol. 48, No. 6, Dec. 2002, pp. 505-511 (XP002580474).
Zaumanis et al., "Evaluation of Rejuvenator's Effectiveness with Conventional Mix Testing for 100% Reclaimed Asphalt Pavement Mixtures," Transportation Research Board of the National Academies, vol. 2370, No. 1, Jan. 2013, pp. 17-25. (XP055526878).
Zaumanis et al., "Influence of six rejuvenators on the performance properties of Reclaimed Asphalt Pavement (RAP) binder and 100% recycled asphalt mixtures," Construction and Building Materials, vol. 71, Sep. 2014, pp. 538-550. (XP029080483).
Harhar et al., "Chemical Characterization and Oxidative Stability of Castor Oil Grown in Morocco", Moroccan Journal of Chemistry, vol. 4, No. 2, Apr. 2016, pp. 279-284.
Mühlen et al., "Chapter 7—Introduction to Atomic Force Microscopy and its Application to the Study of Lipid Nanoparticles," in Particle and Surface Characterization Methods, ISBN 3887630572, Feb. 1998, pp. 99-127.
Product Data Sheet from MP Biomedicals Website, Catalog No. 102886, beta-Sitosterol, 2015, 1 page.
Sui et al., "New Low-Temperature Performance-Grading Method: Using 4-mm Parallel Plates on a Dynamic Shear Rheometer," Transportation Research Record: Journal of the Transportation Research Board, vol. 2207, Jan. 2011, pp. 43-48.
Wood Chemistry, PSE 406/Chem E 470, Lecture 13, Diterpenes and Triterpenes, Wood Chemistry, 2015. pp. 5.
Alvarez-Henao et al., "Supercritical fluid extraction of phytosterols from sugarcane bagasse: Evaluation of extraction parameters," The Journal of Supercritical Fluids, vol. 179, Oct. 2021, 105427. (8 pp).
Appleton et al., "The Sterol Content of Fungi II. Screening of Representative Yeasts and Molds for Sterol Content," Applied Microbiology Applied Microbiology, vol. 3, No. 4, Mar. 1955, pp. 249-251.
"Sterols" retrieved from http://www.cyberlipid.org/sterols/ster0003.htm, Nov. 2016, 22 pp.
Weete et al., "Phylogenetic Distribution of Fungal Sterols," PLoS One, vol. 5, No. 5, May 2010, e10899, pp. 6.

\* cited by examiner

CRUDE STEROL AS AN ADDITIVE IN ASPHALT BINDER

CROSS-REFERENCE TO RELATED APPLICATIONS

This application claims priority to PCT International Application No. PCT/US2016/064961, filed on Dec. 5, 2016, which claims priority to PCT International Application No. PCT/US2016/037077 filed on Jun. 10, 2016 and claims the benefit of U.S. Provisional Patent Application Nos. 62/385,905 filed Sep. 9, 2016 and 62/385,899, filed Sep. 9, 2016, each reference herein incorporated by reference in their entirety.

BACKGROUND

Asphalt pavement is one of the most recycled materials in the world, finding uses when recycled in shoulders of paved surfaces and bridge abutments, as a gravel substitute on unpaved roads, and as a replacement for virgin aggregate and binder in new asphalt pavement. Typically, use of recycled asphalt pavement is limited to sub-surface pavement layers or to controlled amounts in asphalt base and surface layers. Such uses are limited in part because asphalt deteriorates with time, loses its flexibility, becomes oxidized and brittle, and tends to crack, particularly under stress or at low temperatures. These effects are primarily due to aging of the organic components of the asphalt, e.g., the bitumen-containing binder, particularly upon exposure to weather. The aged binder is also highly viscous. Consequently, reclaimed asphalt pavement has different properties than virgin asphalt and is difficult to process.

To reduce or retard the impact of asphalt aging on the long-range performance of mixtures, numerous materials have been investigated. For example, rejuvenators are marketed with a stated goal of reversing the aging that has taken place in recycled raw materials such as reclaimed asphalt pavement (RAP) and reclaimed asphalt shingles (RAS). It is unlikely that rejuvenation of asphalt can actually occur and the more likely scenario is that these additives may instead serve as softening agents for the virgin binders employed in mixtures containing RAP and/or RAS. In some instances, 10% or more by weight of these softening agents are added to the virgin binder when such mixtures are produced.

Aging can be assessed by measuring $\Delta Tc$, the difference between the Stiffness critical temperature and the creep critical temperature after aging.

SUMMARY

Disclosed are compositions and methods that may retard, reduce or otherwise overcome the effects of aging in recycled or reclaimed aged asphalt so as to preserve or retain some or all of the original properties of the virgin binder or virgin asphalt originally used when laying down the aged asphalt. In some embodiments, the disclosed compositions and methods may alter the aging rate of the total binder present in a mix containing virgin asphalt and high levels of RAP or RAS. The disclosed compositions and methods use a class of plant derived chemistry, the sterol class of compounds like those depicted in FIG. 1. While plant sterols do not contain the same number of condensed or partially unsaturated rings as asphaltenes, they do have the benefit of not being a linear or branched linear molecule.

In one embodiment, the present disclosure provides a method for slowing the aging or restoring aged asphalt binder comprising adding a crude sterol to an asphalt binder, wherein the asphalt binder comprises a virgin asphalt binder, reclaimed asphalt binder material comprising asphalt pavement (RAP), asphalt shingles (RAS) or combinations of both and from 0.5 to 15 wt. % of the crude sterol source based on the virgin asphalt binder In one embodiment, the present disclosure provides a method for reusing reclaimed asphalt binder for asphalt binder pavement production, comprising adding a crude sterol to an asphalt binder, wherein the asphalt binder comprises a virgin asphalt binder, reclaimed asphalt binder material comprising asphalt pavement (RAP), asphalt shingles (RAS) or combinations of both and from 0.5 to 15 wt. % of the crude sterol based on the virgin asphalt binder.

In another embodiment, the present disclosure provides an asphalt binder comprising, virgin asphalt binder, reclaimed asphalt binder material comprising reclaimed asphalt pavement (RAP), reclaimed asphalt shingles (RAS) or combinations of both, a crude sterol, wherein and from 0.5 to 15 wt. % of the crude sterol source based on the virgin asphalt binder.

In yet another embodiment, the present disclosure provides method for restoring aged asphalt binder comprising adding a crude sterol and virgin asphalt binder to a reclaimed asphalt binder, wherein 0.5 to 15 wt. % of the crude sterol is based on virgin asphalt binder.

In one embodiment, the present disclosure provides an asphalt binder comprising virgin asphalt binder, reclaimed asphalt binder material comprising reclaimed asphalt pavement (RAP), reclaimed asphalt shingles (RAS) or combinations of both, and an anti-aging additive in the range of 0.5 to 15 wt. % of the virgin binder, wherein the anti-aging additive is free of cyclic organic compositions that contain esters or ester blends.

In one embodiment, the present disclosure provides an asphalt binder comprising virgin asphalt binder, reclaimed asphalt binder material comprising reclaimed asphalt pavement (RAP), reclaimed asphalt shingles (RAS) or combinations of both, and a restorative additive in the range of 0.5 to 15 wt. % of the virgin binder, wherein the restorative additive is free of cyclic organic compositions that contain esters or ester blends.

In another embodiment, the present disclosure provides a method for slowing the aging or restoring aged asphalt binder comprising:

adding a restorative additive to an asphalt binder, wherein the asphalt binder comprises a binder, reclaimed asphalt binder material comprising reclaimed asphalt pavement (RAP), reclaimed asphalt shingles (RAS) or combinations of both, wherein the restorative additive is added in a range of 0.5 to 15 wt. % of the virgin asphalt binder.

In one embodiment, the present disclosure provides an asphalt paving comprising aggregate, virgin asphalt binder, reclaimed asphalt material comprising RAP, RAS or combinations of both, a triterpenoid, and a softening agent, wherein the triterpenoid preferably is free of cyclic organic esters, and has a triterpenoid content (e.g., a sterol content) of at least about 0.5, at least about 1 wt. %, at least about 5 wt. %, up to about 8%, up about 10%, or up to about 15 wt. % based on the virgin asphalt binder weight.

In another embodiment, the present disclosure provides an asphalt comprising virgin asphalt binder, reclaimed asphalt material comprising RAP, RAS or combinations of both, a triterpenoid, and a softening agent, wherein the triterpenoid preferably is free of cyclic organic esters, and has a sterol content of at least about 0.5, at least about 1 wt.

%, at least about 5 wt. %, up to about 8%, up to about 10%, or up to about 15 wt. % based on the virgin asphalt binder weight.

The triterpenoid in the disclosed embodiments for example, may be a sterol, a stanol, a plant sterol, or a plant stanol.

In other embodiments, the present disclosure provides a method for retarding oxidative aging of the asphalt binder, which method comprises adding one or more triterpenoids (e.g., a triterpenoid blend) to a binder or asphalt, wherein the terpenoid(s) preferably do not contain an ester or an ester blend, and wherein the triterpenoid content in the composition is of at least about 0.5, at least about 1 wt. %, at least about 5 wt. %, up to about 8%, up about 10%, or up to about 15 wt. % based on the virgin asphalt binder weight.

Exemplary embodiments of the present disclosure include, for example, i) asphalt binder comprising RAS at a binder replacement level 1% and greater, ii) asphalt binder comprising RAP at binder replacement levels 20% and greater, iii) asphalt binders comprising RAP and RAS used in combination at binder replacement levels of 10% and greater RAP-derived binder and binder replacement levels of 1% and greater RAS-derived binder, iv) asphalt binder comprising asphalt binder extracted and recovered from post-consumer waste shingles at binder replacement levels of 3% by weight and greater, v) asphalt binder comprising asphalt binder extracted from manufacture's waste shingles at binder replacement levels of 5% by weight and greater, vi) asphalt binder comprising oxidized asphalts meeting ASTM specification D312 for Type II, Type III, or Type IV and coating asphalt at binder replacement levels of 3% by weight and greater, vii) asphalt binder comprising extracted and recovered RAP at binder replacement levels of 10% by weight and greater, viii) asphalt binder comprising re-refined engine oil bottoms (REOB) at binder replacement levels of 1% and grater by weight, ix) asphalt binder comprising paraffinic oils at binder replacement levels of 1% and greater by weight, x) asphalt paving comprising aggregate, aggregate and RAP, aggregate and RAS, or aggregate and a combination of RAP and RAS mixed with binder containing REOB at binder replacement levels of 1% and higher by weight; xi) said asphalt paving as enumerated in x) mixed with paraffinic oils at binder replacement levels of 1% and higher by weight.

In still other embodiments, the disclosure provides a method for reusing reclaimed asphalt for asphalt pavement production, which method comprises the use of one or more triterpenoids (e.g., a triterpenoid blend) as an additive to a bituminous or asphalt mixture that preferably the additive does not contain an ester or an ester blend, and wherein the triterpenoid additive is at least about 0.5, at least about 1 wt. %, and up to about 3, up to about 10, or up to about 15 wt. % based on the virgin asphalt weight.

A method for identifying an anti-aging additive comprising:
(a) determining a ΔTc for an asphalt binder after aging;
(b) determining a ΔTc for an asphalt binder that is the same as the asphalt binder in (a) but with an anti-aging additive;
(c) comparing the ΔTcs after aging of the asphalt binder with and without the anti-aging additive; and
(d) identifying the anti-aging additive that provides a higher ΔTc after 40 hours of PAV aging of at least 25% higher than the asphalt binder without the additive or a higher ΔTc after 60 hours of PAV aging than the asphalt binder without the additive.

Other embodiments comprise a method for applying a road pavement surface, which method employs an asphalt comprising aggregate, virgin asphalt binder, reclaimed asphalt material comprising RAP, RAS or combinations of both, a triterpenoid, and a softening agent, wherein the triterpenoid preferably is free of cyclic organic esters or ester blends, and has a sterol content of at least about 0.5, at least about 1 wt. %,or up to about 15 or up to about 10 wt. % based on the virgin asphalt binder weight. In a further embodiment, the asphalt paving is prepared, mixed, applied to a base surface, and compacted.

Figure 15:
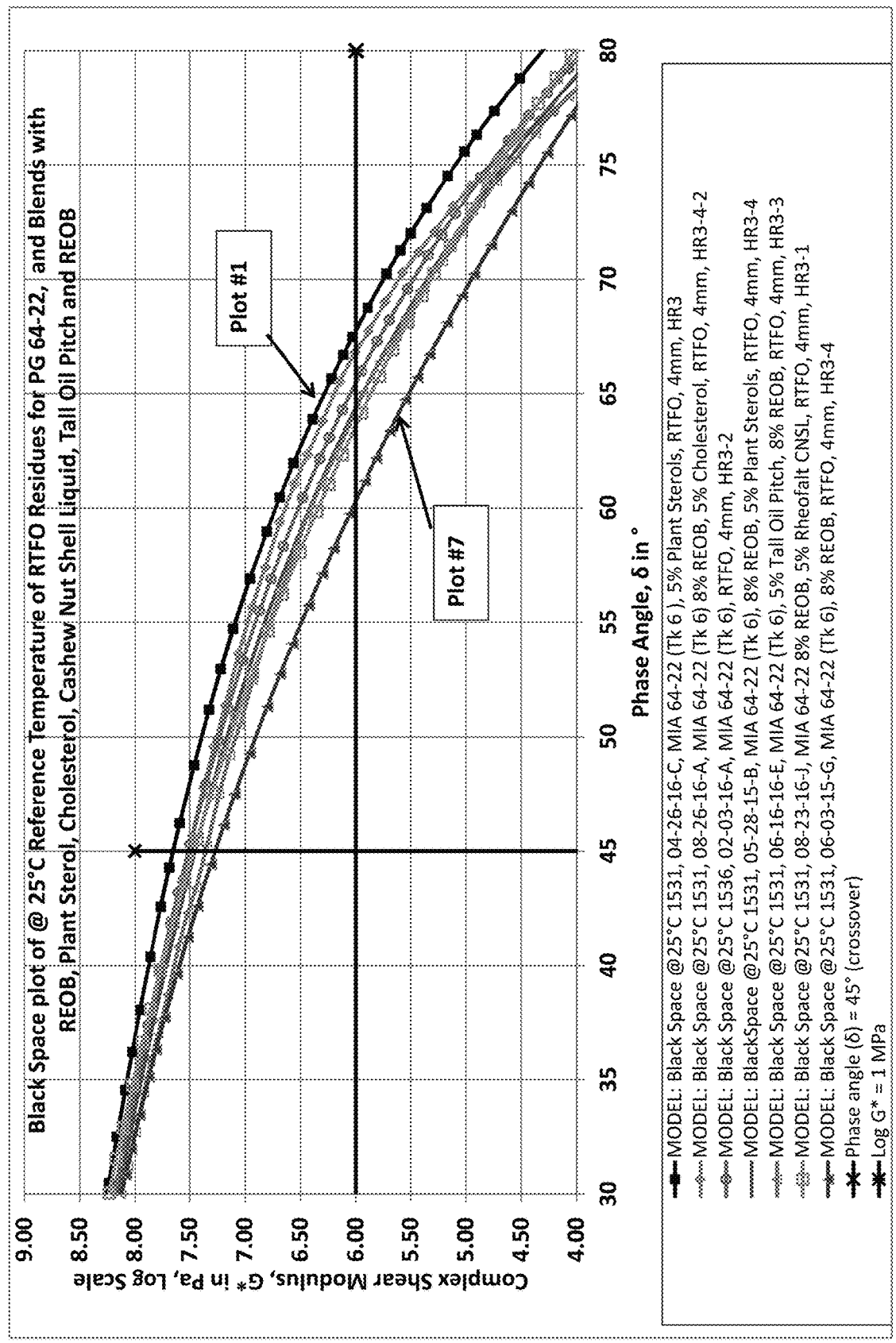

FIG. 15 is a Black Space plot at a reference temperature of 25° C. of RTFO samples. The samples were produced with PG 64-22 and containing (1) 5% plant sterol only, (2) 8% REOB, plus 5% cholesterol, (3) no REOB and no other additive [serves as positive control], (4) 8% REOB, 5% blended plant sterols, (5) 8% REOB, 5% tall oil pitch, (6) 8% REOB, 5% cashew nut shell liquid (CNSL), (7) 8% REOB and no other additive [serves as negative control].

Figure 16:
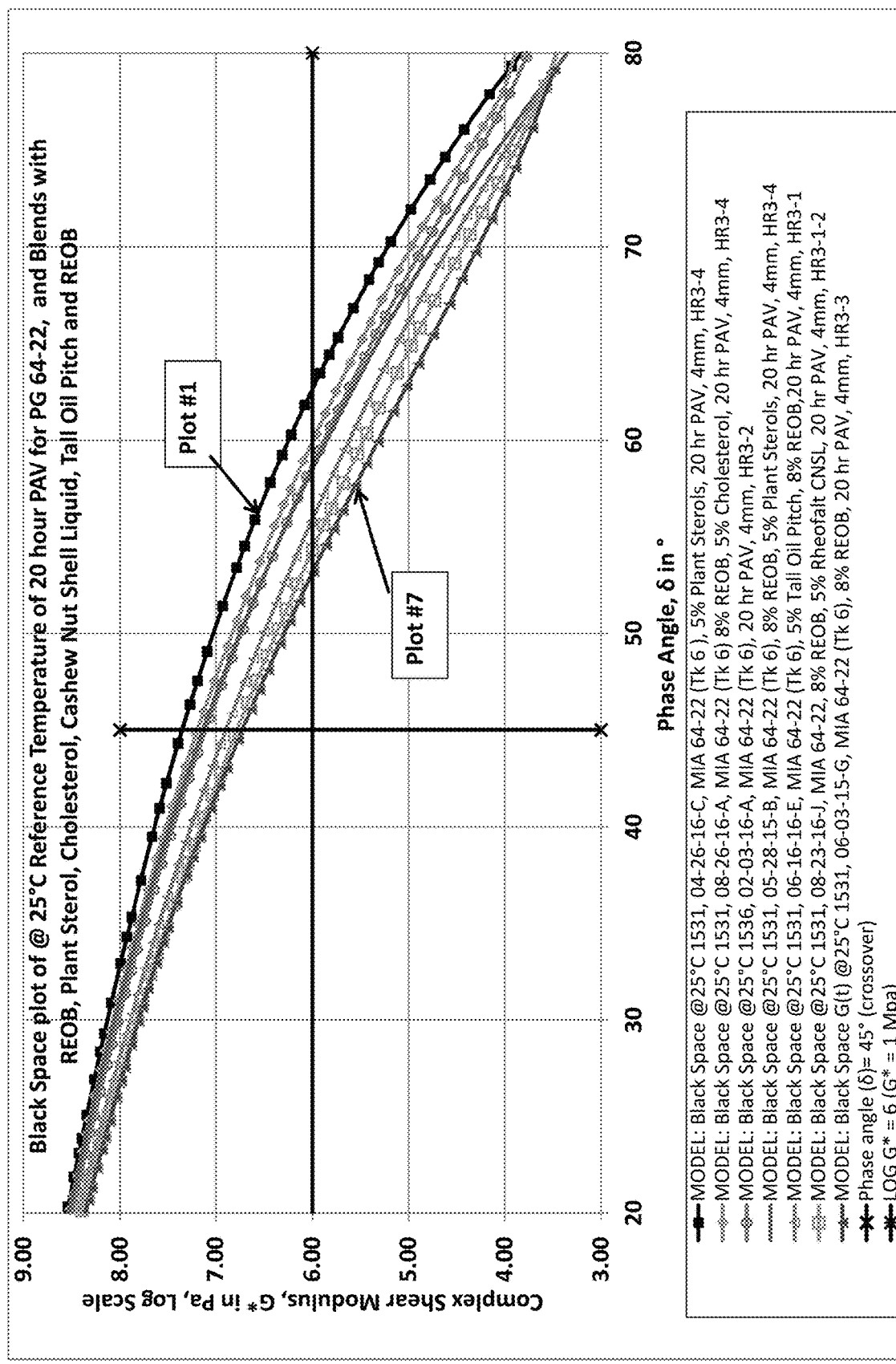

FIG. 16 is a Black Space plot at a reference temperature of 25° C. of 20 hours PAV aging for samples described in Figure legend 15.

Figure 17:
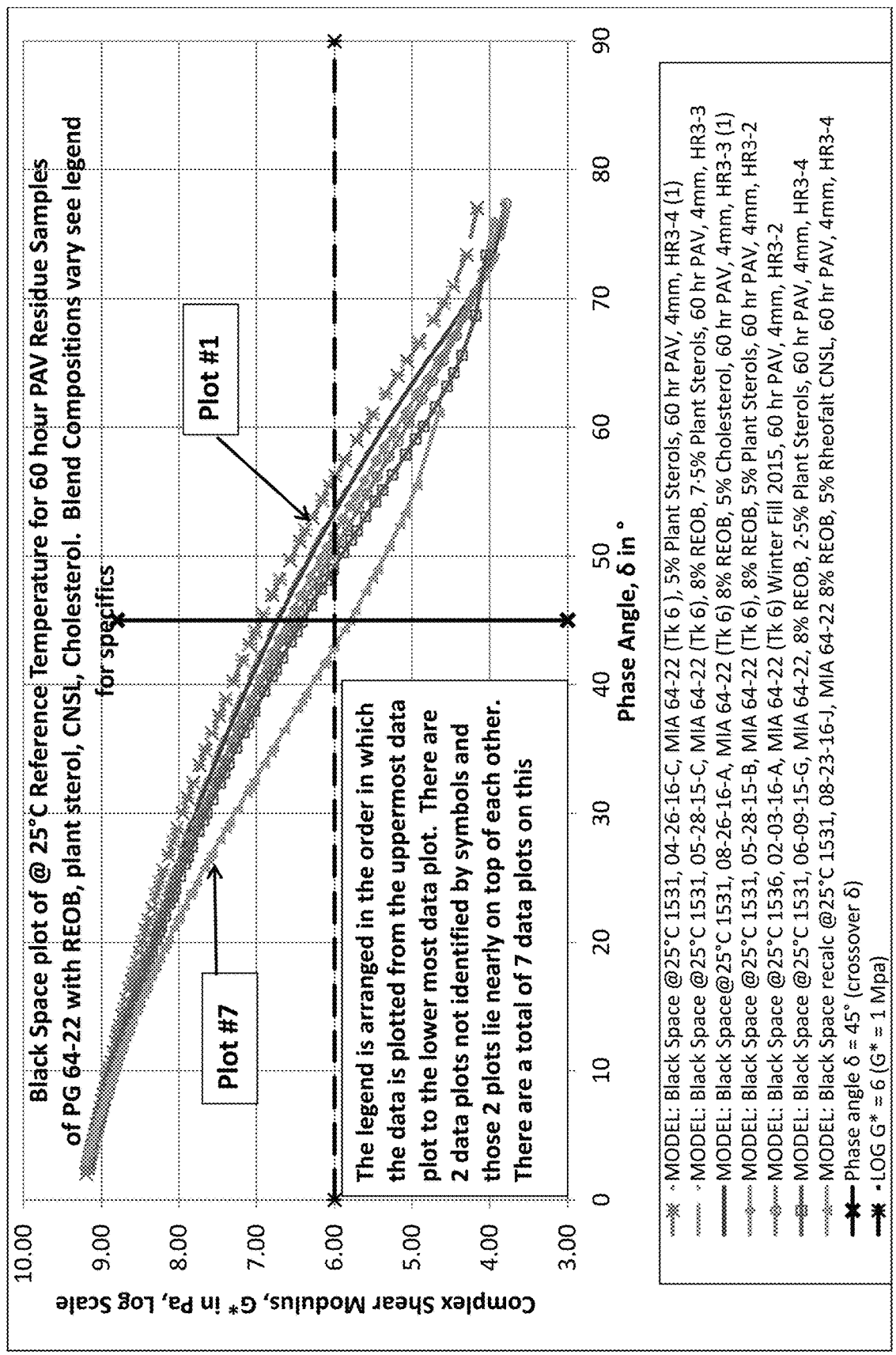

FIG. 17 is a Black Space plot at a reference temperature of 25° C. of 60 hours PAV aging. This plot compares samples produced with PG 64-22 and containing (1) 5% plant sterols [positive control] (2) 8% REOB and 7.5% blended plant sterol (3) 8% REOB, 5% cholesterol, (4) 8% REOB and 5% blended plant sterols, (5) no additives (6) 8% REOB, 2.5% blended plant sterol (7) 8% REOB and 5% cashew nut shell liquid (CNSL).

Figure 18:
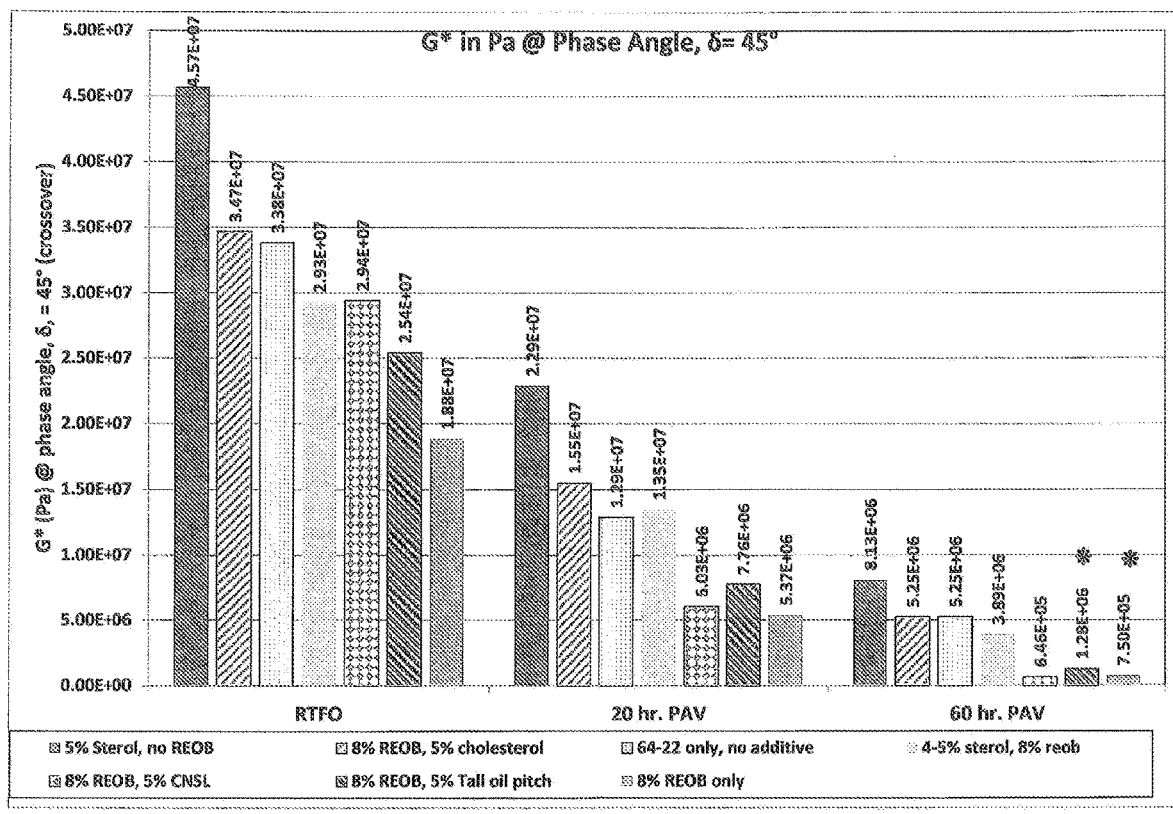

FIG. 18 is a bar graph plot comparing the complex shear modulus, G*, at a phase angle of 45° for binders shown in FIGS. 15 through 17.

Figure 19:
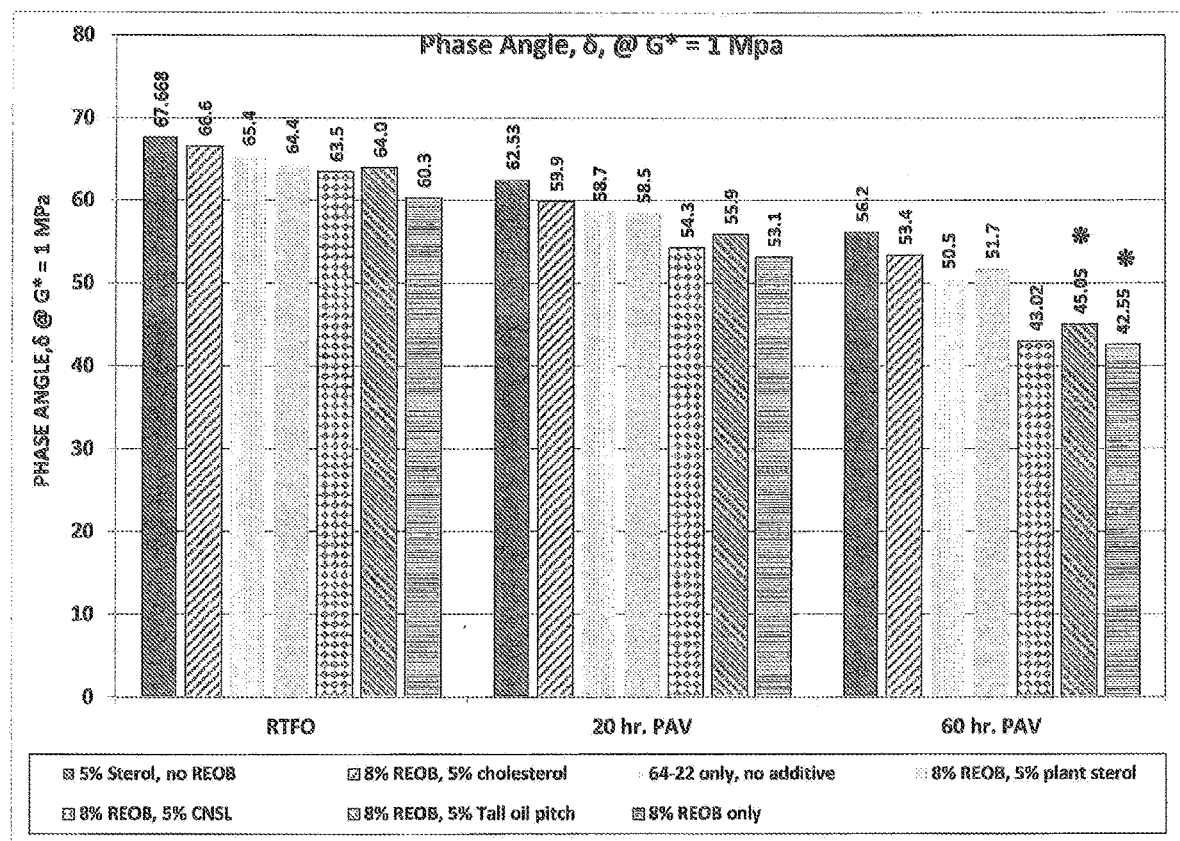

FIG. 19 is a bar graph plot comparing the phase angle at a complex shear modulus, G*, of 1 mega Pascal (MPa) for the binders shown in FIGS. 15 through 17.

Figure 20:
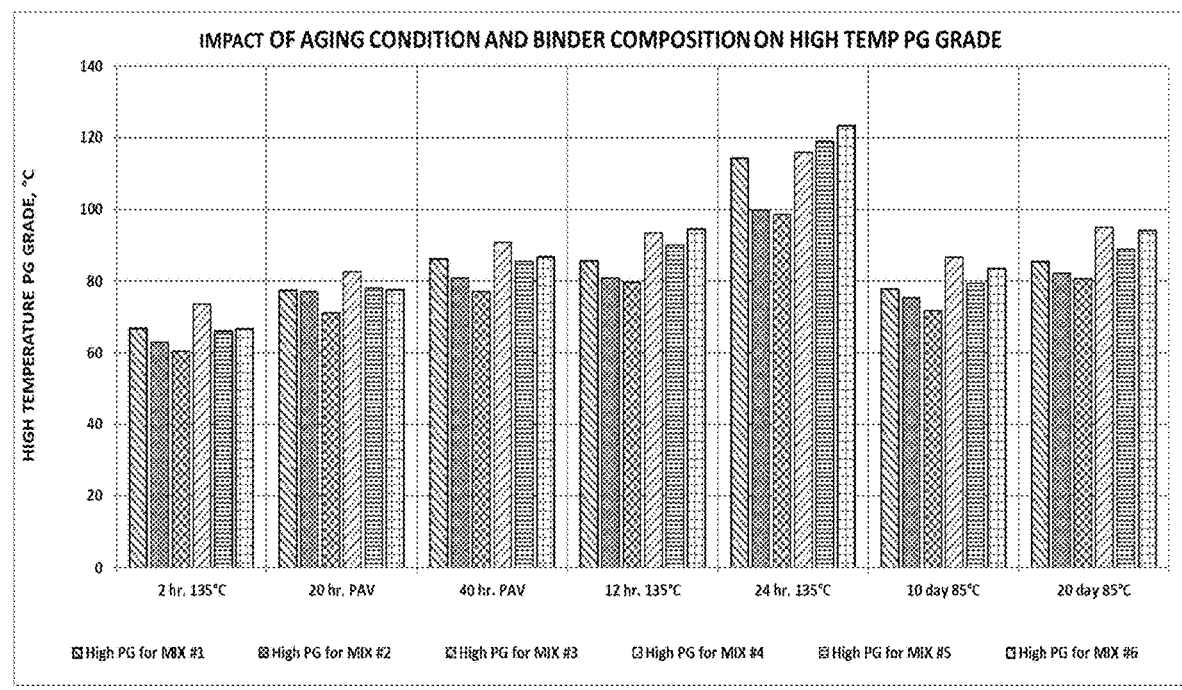

FIG. 20 is a bar graph plot showing variation in high temperature PG grade of binders described in Example 10.

Figure 21:
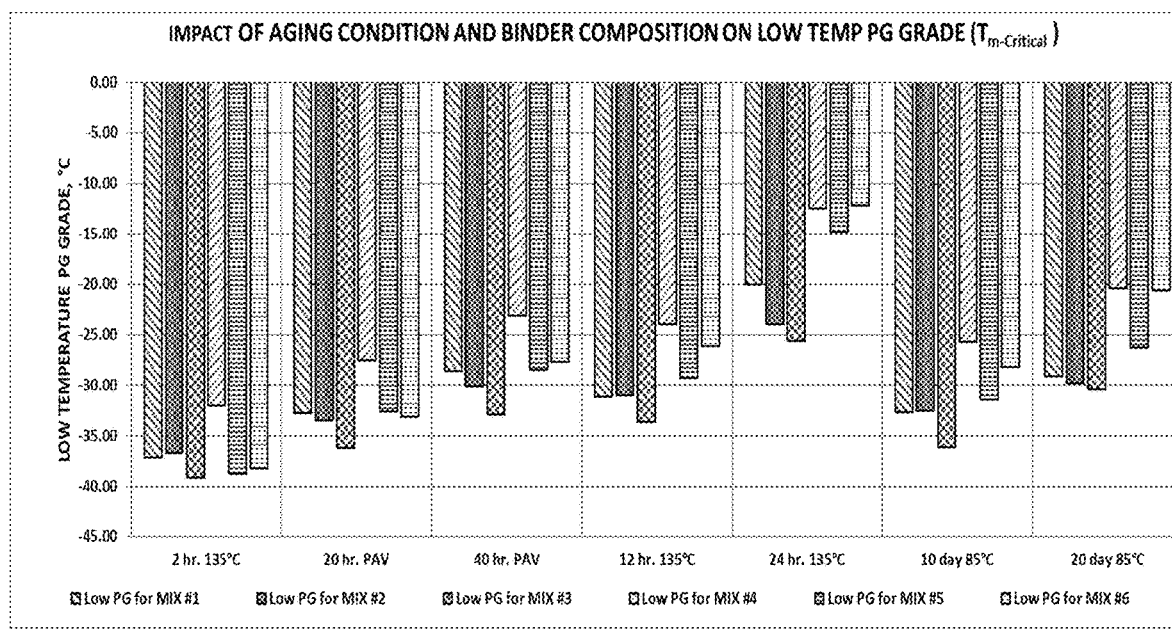

FIG. 21 is a bar graph plot showing the variation in low temperature PG grade failure temperatures of binders described in Example 10.

Figure 22:
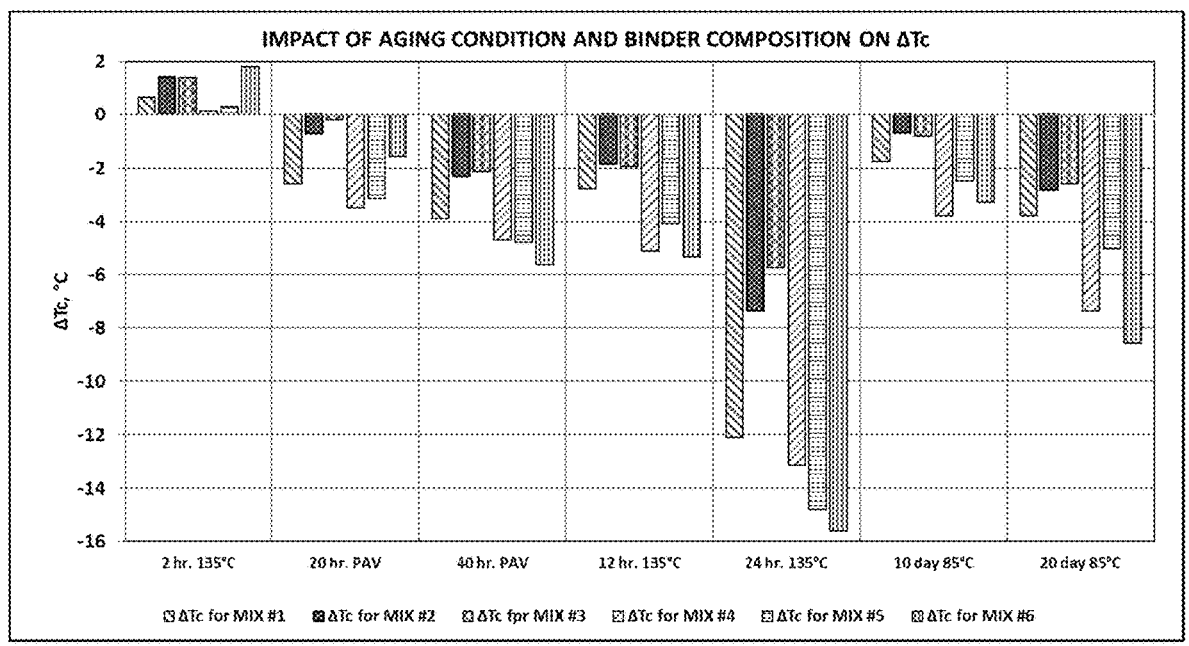

FIG. 22 is a bar graph plot showing the variation in ΔTc for the binders described in Example 10.

Figure 23:
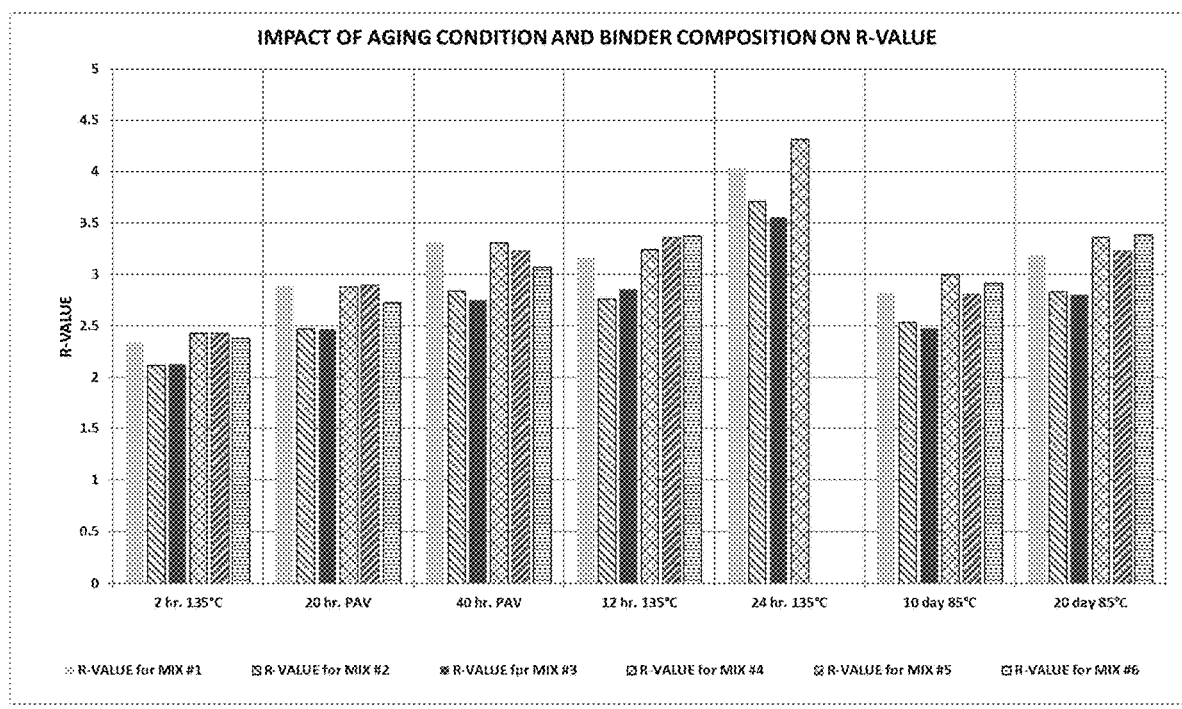

FIG. 23 is a plot of R-Value for the binders described in Example 10.

Figure 24:
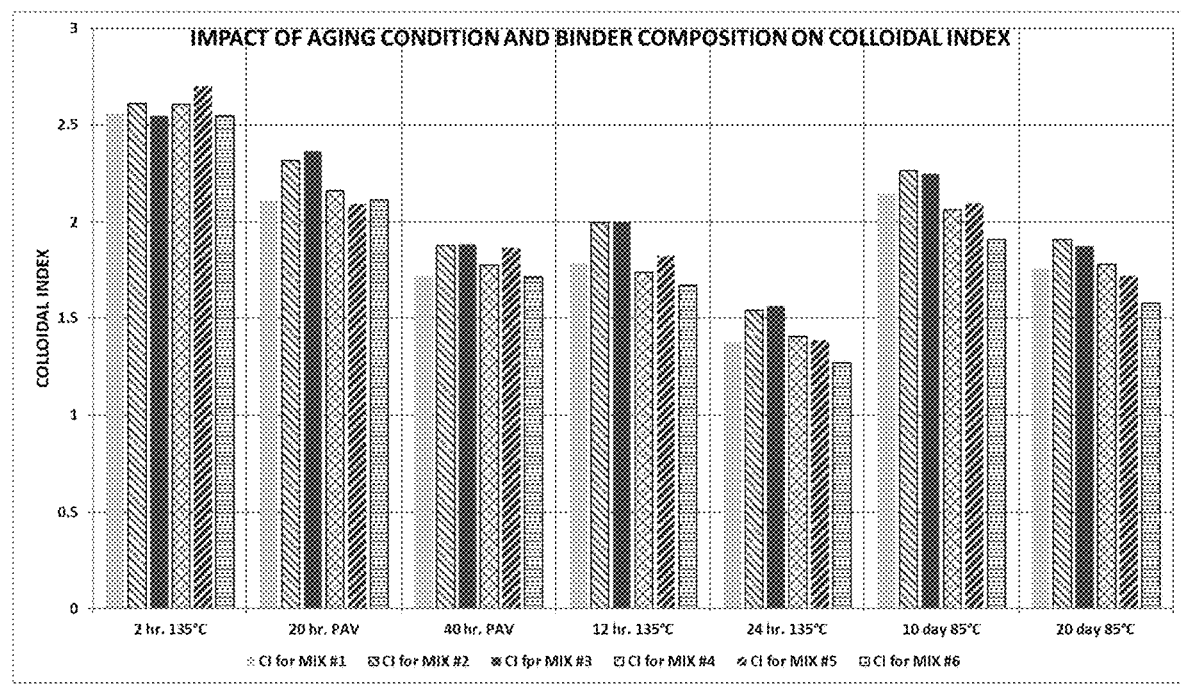

FIG. 24 is a bar graph plot showing the variation in Colloidal Index for the binders described in Example 10.

DETAILED DESCRIPTION

The disclosed asphalt or asphalt binders contain anti-aging (viz., age reducing or aging retarding) additives that help in the preservation, recycling and reuse of asphalt or asphalt bindes. The anti-aging additive preferably is free of cyclic organic compositions that contain esters or ester blends. The disclosed compositions have particular value for the renewal of reclaimed asphalt, and especially RAP.

The disclosed asphalt binders can provide recycled asphalt (e.g. RAP or RAS) improved physical and rheological characteristics such as stiffness, effective temperature range, and low temperature properties. Some embodiments provide for the use of binder extracted from RAS in asphalt. Certain embodiments provide for the addition of an additive to minimize potential detrimental low-temperature effects of recycled asphalt while allowing for higher stiffness at high temperatures.

Headings are provided herein solely for ease of reading and should not be interpreted as limiting.

Abbreviations, Acronyms & Definitions

"Aged" refers to asphalt or binder that is present in or is recovered from reclaimed asphalt. Aged binder has high viscosity compared with that of virgin asphalt or virgin binder as a result of aging and exposure to outdoor weather. The term "aged" also refers to virgin asphalt or virgin binder that has been aged using the laboratory aging test methods described herein (e.g. RTFO and PAV). "Aged" may also refer to hard, poor-quality, or out-of-specification virgin asphalt or virgin binder particularly virgin binders having a ring-and-ball softening point greater than 65° C. by EN 1427 and a penetration value at 25° C. by EN 1426 less than or equal to 12 dmm.

"Aggregate" and "construction aggregate" refer to particulate mineral material such as limestone, granite, trap rock, gravel, crushed gravel sand, crushed stone, crushed rock and slag useful in paving and pavement applications.

"Anti-aging additive" refers to sterols or sterol mixes that can be combined with aged binder to retard the rate of aging of asphalt or binder, or to restore or renew the aged asphalt or aged binder to provide some or all of the original properties of virgin asphalt or virgin binder.

"Asphalt" refers to a binder and aggregate and optionally other components that are suitable for mixing with aggregate and binder. Depending on local usage, the terms "asphalt mix" or "mix" may be used interchangeably with the term "asphalt."

"Asphalt pavement" refers to compacted asphalt.

"Binder" refers to a highly viscous liquid or semi-solid form of petroleum. "Binder" can include, for example bitumen. The term "asphalt binder" is used interchangeably with the term "binder."

"Bitumen" refers to a class of black or dark-colored (solid, semisolid, or viscous) cementitious substances, natural or manufactured, composed principally of high molecular weight hydrocarbons, of which asphalts, tars, pitches, and asphaltenes are typical.

Black Space Plot or Black Space Diagram is the term for a plot of rheological data where complex modulus is plotted on the Y-Axis and phase angle is plotted on the X-Axis. These plots have been used by researchers to rank the impact of aging on binders and to rank the impact of additives, including those being marketed as rejuvenating additives, on binders. As binders age the binder stiffness modulus increases and the binder phase angle decreases as the binder becomes more brittle. Lower phase angles are associated with a binder becoming more elastic and less viscous at a given temperature.

"Crude" when used with respect to a material containing a sterol means sterol that has not been fully refined and can contain components in addition to sterol.

"M-critical" or "Creep critical" grade refers to the low temperature relaxation grade of a binder. The creep critical temperature is the temperature at which the slope of the flexural creep stiffness versus creep time according to ASTM D6648 has an absolute value of 0.300. Alternatively the stiffness and creep critical temperatures can be determined from a 4 mm Dynamic Shear Rheometer (DSR) test or Bending Beam Rheometer (BBR).

"Neat" or "Virgin" binders are binders not yet used in or recycled from asphalt pavement or asphalt shingles, and can include Performance Grade binders.

"PAV" refers to a Pressurized Aging Vessel. The PAV is used to simulate accelerated aging of asphalt or binder as described in ASTM D6521-13, Standard Practice for Accelerated Aging of Asphalt Binder Using a Pressurized Aging Vessel (PAV).

"Pure" when used with respect to a sterol or mixture of sterols means having at least a technical grade of purity or at least a reagent grade of purity.

"Reclaimed asphalt" and "recycled asphalt" refer to RAP, RAS, and reclaimed binder from old pavements, shingle manufacturing scrap, roofing felt, and other products or applications.

"Reclaimed asphalt pavement" and "RAP" refer to asphalt that has been removed or excavated from a previously used road or pavement or other similar structure, and processed for reuse by any of a variety of well-known methods, including milling, ripping, breaking, crushing, or pulverizing.

"Reclaimed asphalt shingles" and "RAS" refer to shingles from sources including roof tear-off, manufacture's waste asphalt shingles and post-consumer waste.

"RTFO" refers to a Rolling Thin Film Oven. The RFTO is used for simulating the short-term aging of binders as described in ASTM D2872-12e1, Standard Test Method for Effect of Heat and Air on a Moving Film of Asphalt (Rolling Thin-Film Oven Test).

"S-Critical" or "stiffness critical" grade refers to the low temperature stiffness grade of a binder. The stiffness critical temperature is the temperature at which a binder tested according to ASTM D6648 has a flexural creep stiffness value of 300 MPa or as determined by either the Bending Beam Rheometer test or 4 mm DSR test as described in ΔTc.

SHRP refers to the Strategic Highway Research Program which develops new binder specifications in 1993.

"Softening agent" refers to low viscosity additives that ease (or facilitate) the mixing and incorporation of a recycled binder into virgin binder during an asphalt production process.

"Temp" is used in Tables and Figures as a contraction for the word Temperature.

"ΔTc" refers to the value obtained when the low temperature creep or m-value critical temperature is subtracted from the low temperature stiffness critical temperature. The 4 mm dynamic shear rheometer (DSR) test and analysis procedures are described by Sui, C., Farrar, M., Tuminello, W., Turner, T., A New Technique for Measuring low-temperature Properties of Asphalt Binders with Small Amounts of Material, Transportation Research Record: No 1681, TRB 2010. See also Sui, C., Farrar, M. J., Harnsberger, P. M., Tuminello, W. H., Turner, T. F., New Low Temperature Performance Grading Method Using 4 mm Parallel Plates on a Dynamic Shear Rheometer. TRB Preprint CD, 2011, and by Farrar, M., et al, (2012), Thin Film Oxidative Aging and Low Temperature Performance Grading Using Small Plate Dynamic Shear Rheometry: An Alternative to Standard RTFO, PAV and BBr. Eurasphalt & Eurobitume 5th E&E Congress—2012 Istanbul (pp. Paper O5ee-467). Istanbul: Foundation Euraspalt.

All weights, parts and percentages are based on weight unless otherwise specified.

Binders

Current asphalt paving practices involve the use of high percentages of RAP and RAS as components in the asphalt being paved. Typically RAP concentrations can be as high as 50% and RAS concentrations can be as high as 6% by weight of the paving mixture. The typical binder content of RAP is in the range of 5-6% by weight and the typical binder content of RAS is in the range of 20-25% by weight. Consequently, a binder containing 50% by weight of RAP will contain 2.5% to 3% RAP binder contributed to the final binder mixture and a binder mixture containing 6% RAS by weight will contain 1.2% to 1.5% RAS binder contributed to the final binder mixture. In many instances RAP and RAS are combined in binder mixtures; for example 20% to 30% RAP and 5% to 6% RAS can be incorporated into a binder mixture. Based on the typical asphalt binder contents of RAP and RAS, asphalt binders containing 20% to 30% RAP and 5% to 6% RAS can result in 2% binder coming from the RAP and RAS combination to as much as 3.3% binder being derived from the RAP and RAS combination. Since a typical asphalt paving will contain about 5.5% total bitumen there can be about 36% to as much as 60% of the total bitumen in the bituminous mixture from these recycled sources.

Characteristics of bitumen in these reclaimed sources relative to virgin binders used in bituminous mixtures are shown in Table 1.

TABLE 1

| Binder & source | High temperature stiffness grade, ° C. | 4 mm DSR S-critical Grade ° C., 20 hr. PAV | Critical Low temperature grade based on 4 mm DSR m-critical Grade ° C. 20 hr. PAV | ΔTc° C., 20 hr. PAV | Critical Low temperature grade based on 4 mm DSR S-Critical Grade ° C., 40 hr. PAV | 4 mm DSR m-critical Grade ° C. 40 hr. PAV | ΔTc° C., 40 hr. PAV |
|---|---|---|---|---|---|---|---|
| PG 58-28 | 60.3 | −31.4 | −30.9 | −0.5 | −30.7 | −27.8 | −2.9 |
| PG 64-22 | 67.1 | −27.1 | −26.2 | −.9 | −25.8 | −23.2 | −2.6 |

| Binder recovered from RAP or RAS | | 4 mm DSR S-critical Grade | Critical Low temperature creep grade based on 4 mm DSR m-critical grade | ΔTc° C. |
|---|---|---|---|---|
| RAP 03-16-15-D | 85.0 | −25.5 | −22.3 | −3.2 |
| RAP 02-23-15-B | 89.5 | −25.3 | −21.3 | −4.0 |
| RAP 03-24-15-D | 98.8 | −22.4 | −17.1 | −5.3 |

TABLE 1-continued

| | | | | |
|---|---|---|---|---|
| RAP 02-09-15-B | 87.5 | −27.8 | −26.2 | −1.6 |
| RAS 04-03-15-D | 158.2 | −27.5 | −0.3 | −27.2 |
| RAS 02-09-15-C | 137.7 | −25.7 | +9.7 | −35.4 |

Table 2 shows the high and low temperature properties of samples produced with virgin binders and bitumen recovered from post-consumer waste shingles after different periods of aging. Also shown in Table 2 are high and low temperature properties of mixtures containing RAP and RAS. Some of these mixtures have undergone extended laboratory aging and some are from field cores.

TABLE 2

| Binder recovered from RAP or RAS containing mixtures either lab or field aged | High temperature grade | Critical Low temperature stiffness grade based on 4 mm DSR | Critical Low temperature creep grade based on 4 mm DSR | ΔTc° C. |
|---|---|---|---|---|
| Field mix 09-27-13-F PG 58-28 + 5% RAS, unaged | 83.1 | −32.3 | −30.6 | −1.7 |
| Field mix 09-27-13-E PG 58-28 + 5% RAS, 5 day aged @ 85° C. | 102.8 | −28.5 | −23.9 | −4.6 |
| US Hwy 14 PG 58-28 + 6% RAS & 11% RAP, 10 day aged @ 85° C. | 85.4 | −30.9 | −24.1 | −6.8 |
| US Hwy 14 PG 52-34 + 6% RAS & 11% RAP, 10 day aged @ 85° C. | 80.8 | −35.6 | −29.9 | −5.7 |
| US Hwy 14 PG 58-28 + 31% RAP, 10 day aged @ 85° C. | 79.5 | −29.6 | −26.7 | −2.9 |
| Core from field paved 2011, cored 2013, binder from top ½ inch of core (mix contained PG 58-28 + 5% RAS or 22% shingle binder replacement) | 87.6 | −25.9 | −21.7 | −4.2 |
| Core from field paved 2011, cored 2013, binder from second ½ inch of core below the surface (mix contained PG 58-28 + 5% RAS or 22% shingle binder replacement) | 86.0 | −25.6 | −21.9 | −3.8 |
| Core from field paved 2011, cored 2013, binder from layer 2 inches below surface (mix contained PG 58-28 + 5% RAS or 22% shingle binder replacement) | 80.7 | −26.0 | −24.2 | −1.8 |

Tables 1 and 2 show the impact of incorporating high binder replacement levels of recycled materials, especially those derived from post-consumer waste shingles. The data demonstrate the desirability of incorporating additives into bitumen and bituminous mixtures to mitigate the impact of the bitumen from these recycled components and retard further oxidative aging of the total bitumen in the final mixture. The last three rows of Table 2 show that the further away from the air-mixture interface, the lower the impact on ΔTc parameter. This parameter may be used to assess the impact of aging on binder properties and more specifically the impact of aging on the relaxation properties of the binder; the relaxation property is characterized by the property referred to as "low temperature creep grade".

Research published in 2011 showed, based on recovered binder data from field cores, that ΔTc could be used to identify when a pavement reached a point where there was a danger of non-load related mixture cracking and also when potential failure limit had been reached. In that research the authors subtracted the stiffness-critical temperature from the creep or m-critical temperature and therefore binders with poor performance properties had calculated ΔTc values that were positive. Since 2011 industry researchers have agreed to reverse the order of subtraction and therefore when the m-critical temperature is subtracted from the stiffness critical temperature binders exhibiting poor performance properties calculate to ΔTc values that are negative. The industry generally agreed that to have poor performing binders become more negative as performance decreased seemed to be more intuitive. Therefore, today in the industry and as used in the application, a ΔTc warning limit value is −3° C. and a potential failure value is −5° C.

Reports at two Federal Highway Administration Expert Task Group meetings have shown a correlation between ΔTc values of binders recovered from field test projects and severity of pavement distress related to fatigue cracking. Additionally, it has been shown that when binders used to construct these field test projects were subjected to 40 hours of PAV aging, the ΔTc values showed a correlation to pavement distress related to fatigue cracking, especially top down fatigue cracking which is generally considered to result from loss of binder relaxation at the bituminous mixture surface.

It is therefore desirable to obtain bituminous mixtures with bitumen materials that have a reduced susceptibility to the development of excessively negative ΔTc values.

The data in Table 1 show typical virgin binders produced at refineries can maintain a ΔTc of greater than −3° C. after 40 hours of PAV aging. Further, the data in Table 1 show that binder recovered from RAP can have ΔTc values of less than −4° C., and that the impact of high RAP levels in new bituminous mixtures should be evaluated. Further, the extremely negative values of ΔTc for RAS recovered binders require additional scrutiny as to the overall impact of RAS incorporation into bituminous mixtures.

Table 2 shows that it is possible to age bituminous mixtures under laboratory aging followed by recovery of the binder from the mixtures and determination of the recovered binder ΔTc. The long term aging protocol for bituminous mixtures in AASHTO R30 specifies compacted mix aging for five days at 85° C. Some research studies have extended the aging time to ten days to investigate the impact of more severe aging. Recently, aging loose bituminous mixes at 135° C. for 12 and 24 hours and in some instances for even greater time periods have been presented as alternatives to compacted mix aging. The goal of these aging protocols is to produce rapid binder aging similar to field aging representative of more than five years in service and more desirably eight to 10 years in service. For example, it has been shown for mixtures in service for around eight years that the ΔTc of the reclaimed or recycled asphalt from the top ½ inch of pavement was more severe than 12 hours aging at 135° C. but less severe than 24 hours aging at 135° C.

The data in the first two rows of Table 2 show why long-term aging of mixtures containing recycled products is important. The binder recovered from the unaged mix (row 1) exhibited a ΔTc of −1.7° C., whereas the binder recovered from the 5 day aged mix exhibited a ΔTc of −4.6° C.

Anti-Aging Additives

The disclosed anti-aging additives preferably can alter (e.g., reduce or retard) an asphalt binder aging rate, or can restore or renew an aged or recycled binder to provide some or all of the properties of a virgin asphalt binder. For example, the crude sterol can alter or improve physical and rheological characteristics such as stiffness, effective temperature range, and low temperature properties of an asphalt binder.

In some embodiments, the anti-aging additive belongs to the class of triterpenoids, and in particular to sterols or stanols. The disclosed sterols (e.g. triterpenoids) can effectively work with asphaltenes. Asphaltenes include extensive condensed ring systems with some level of unsaturation. The asphaltene content of typical binders can range from less than 10% to more than 20%. Asphaltenes are typically described as materials that are insoluble in n-heptane. An exact structure is unknown and based on the performance behavior of different binders it is unlikely that the asphaltene structure in any two binders is the same, especially those from different crude sources. Asphaltenes give a binder its color and stiffness and they increase in content as the binder ages. Consequently, the addition of RAP and/or RAS causes the asphaltene content to increase. Increasing asphaltene content along with other products of oxidation such as carbonyls and sulfoxides are responsible for the stiffening of bituminous mixtures and their ultimate failure. By their very chemical nature asphaltenes are not readily soluble in aliphatic chemicals. Aromatic solvents will readily dissolve asphaltenes and aromatic process oils have been used in recycled mixtures. However these oils may contain polynuclear aromatic compounds including listed potential carcinogens and therefore are not desirable additives. Most plant based oils are straight or branched chain hydrocarbons with some level of unsaturation and therefore are not as effective at retarding aging as they are at softening the overall binders in a mixture.

Triterpenoids are a major group of plant natural products that include sterols, triterpene saponins, and related structures. Triterpenoids can be natural or synthetic. Typically they are obtained by extraction from plant material. Extraction processes for the isolation of triterpenoids are described e.g. in the international applications WO 01/72315 A1 and WO 2004/016336 A1, the disclosures of which are each incorporated herein by reference in their entirety.

The triterpenoids include plant sterols and plant stanols. The disclosed triterpenoids refer to the non-esterified forms of any of the plant sterols mentioned herein.

Exemplary pure plant sterols include campesterol, stigasterol, stigmasterol, β-sitosterol, Δ5-avenosterol, Δ7-stigasterol, Δ7-avenosterol, brassicasterol or mixtures thereof. In some embodiments, the sterol blend contains β-sitosterol as the pure sterol. In other embodiments, the sterol blend contains a mixture of pure sterols. Commercially available pure sterols and mixtures of pure sterols include those available from MP Biomedicals (Catalog No. 02102886) referred to as beta-Sitosterol (beta-Sitosterol ~40-60%; campesterol ~20-40%; Stigmasterol ~5%). In some embodiments, a pure sterol can have at least 70 wt. % sterols, and in some embodiments can have at least 80 wt %, at least 85 wt % or at least 95 wt % sterols.

Exemplary crude plant sterols include modified or unmodified natural products containing significant quantities of sterols, including such diverse plant sources as corn oil, wheat germ oil, sarsaparilla root, soybean pitch and corn oil pitch. For example, tall oil pitch is obtained during the process of preparing paper from wood, particularly pine wood. Tall oil pitch is an extremely complex material that can contain rosins, fatty acids, oxidation products and esterified materials, an appreciable fraction of which are sterol esters. Plant sources of crude sterols are inexpensive in that they are the foots or tailings left from various manufacturing processes.

In some embodiments, the crude sterol sources include stigmasterol, β-sitosterol, campesterol, ergosterol, brassicasterol, cholesterol and lanosterol or mixtures thereof. In some embodiments, the crude sterol sources include soy bean oil, corn oil, rice bran oil, peanut oil, sunflower seed oil, safflower oil, cottonseed oil, rapeseed oil, coffee seed oil, wheat germ oil, tall oil, and wool grease. In some embodiments the crude sterol includes a bio-derived source or partially distilled residue of the bio-derived source. In some embodiments, the crude sterol source includes tall oil pitch, soybean oil or corn oil.

Any of the oil tailings or pitches from the disclosed plant sources are suitable crude sterol sources. U.S. Pat. No. 2,715,638, Aug. 16, 1955, to Albrecht, discloses a process for recovering sterols from tall oil pitch whereby the fatty acid impurities are removed by a neutralization process. Following this, the sterol esters are saponified; the free sterols are then recovered and washed with isopropanol and dried.

The crude sterols preferably are obtained from plant sources. The crude sterol can include components in addition to the desired sterol or sterols. Exemplary plant sources for crude sterols include tall oil pitch, crude tall oil, sugar cane oil, hot well skimmings, cottonseed pitch, soybean pitch, corn oil pitch, wheat germ oil or rye germ oil. In some embodiments, tall oil pitch is a source of the crude sterol. Tall oil pitch can include about 30 to 40% unsaponifiable molecules. Unsaponifiables are molecules that do not react with alkali hydroxides. Fatty and rosin acids remaining in the tall oil pitch readily react with potassium or sodium hydroxides and thus the unsaponifiables can be readily separated. It has been shown that 45% of the unsaponifiable fraction can include sitosterols. Therefore, a tall oil pitch sample can contain approximately 13.5% to 18% sterol molecules by weight. In some embodiments the crude sterol can have less than a food grade of purity (e.g., less than 85 wt. % sterols) or contain more than 85 wt. % sterols but also can contain impurities or contaminants that render the material unsuitable for use in foods.

In some embodiments, the crude sterol may be animal derived such cholesterol. Cholesterol is shown here to have similar effects as plant sterols.

The crude sterol added to the asphalt may for example range from about 0.5 to about 15 wt. %, about 1 to about 10 wt. %, or about 1 to about 3 wt. % of the virgin binder in an asphalt.

In some embodiments, crude sterol can alter, reduce or retard the degradation of rheological properties in binders containing recycled bituminous materials that include softening agents such as RAS, RAP, REOB, virgin paraffin or naphthenic base oils, untreated or non-re-refined waste drain oils or waste engine oil materials, vacuum tower asphalt extenders, paraffinic or naphthenic processing oils or lubricating base oils. In some embodiments, the crude sterol when used in an asphalt or asphalt pavement maintains a $\Delta Tc$ value greater than or equal to $-5°$ C. as the asphalt or asphalt pavement is aged.

In some embodiments, the crude sterol can provide an asphalt binder with a $\Delta Tc$ of greater than or equal to $-5.0°$ C. In some embodiments, the crude sterol can provide an asphalt binder with a $\Delta Tc$ of greater than or equal to $-5.0°$ C. after 40 hours of PAV aging. In still other embodiments, the disclosed crude sterol can provide an asphalt binder with a less negative $\Delta Tc$ value and a decreased R-Value following aging, when compared to a similarly-aged asphalt binder without the crude sterol.

It should be noted that in addition to the above mentioned crude sterols such as tall oil pitch, as used herein, a term or phrase that is not qualified by the word "crude" may be considered a pure sterol. The terms "mixed sterol" or "sterol blends" or "sterol in blend" or grammatically equivalent phrases have been used interchangeably to refer to pure sterols.

Softening Agents & Other Additives

Softening agents that may be used in binders include waste engine oil and waste engine oil that may be further processed to provide REOB. REOB is a low cost softening additive and asphalt extender obtained from the residual material remaining after the distillation of waste engine oil either under vacuum or at atmospheric pressure conditions. The distilled fraction from the re-refining process is converted into new lubricating oil for vehicles, but the bottoms do not have an available market due to the presence of metals and other particulates from internal combustion engines. Also these bottoms contain paraffinic hydrocarbons and additives incorporated into the original lubricating oil. For many years REOB were used by some companies as an asphalt extender, but the usage was localized.

Greater amounts of waste engine oils are being re-refined and therefore greater amounts of REOB are being sold into the asphalt binder market. The use of REOB may result in bituminous mixtures, which when aged, exhibit $\Delta Tc$ values of $-4°$ C. or lower with consequent poor performance in pavements. When REOB are added to some asphalts at levels as low as 5% by weight, the resulting $\Delta Tc$ after 40 hr. PAV aging can be $-5°$ C. or lower (viz., more negative). Recovered binders from field mixes shown to contain REOB by means of metals testing have shown greater distress than field mixtures of the same age and the same aggregate and paved at the same time but not containing REOB.

The disclosed crude sterol can mitigate the impact of waste engine oils (e.g. REOB) on $\Delta Tc$ (as evaluated, for example, using 40 hr. of PAV aging) and renew or retard the aging rate of the recycled asphalt.

The disclosed crude sterol can also be used to mitigate the impact of other softening agents, which behave similarly to REOB. In other words, the other softening agents are agents when aged, have $\Delta Tc$ values of $-4°$ C. or lower with consequent poor performance in pavements. These other softening agents include synthetic or virgin lubricating oils (such as MOBIL™ 1 synthetic oil from ExxonMobil Corp. and HAVOLINE™ 10W40 oil from Chevron USA Inc.), virgin paraffin or naphthenic base oils, untreated or non-rerefined waste drain oils or waste engine oil materials, vacuum tower asphalt extenders (the non-distillable fraction from re-refining used engine oil) and paraffinic or naphthenic process oils.

It should be noted that softening agents such as bioderived softening agents (e.g. Cargill's 1103 and Arizona Chemical's RS1100) can soften an asphalt binder without adversely affecting the asphalt binder in the same manner as REOB. The crude sterol can retain much of the beneficial softening of these bioderived softening agents.

The asphalt may contain other components in addition to the disclosed sterol. Such other components can include elastomers, non-bituminous binders, adhesion promoters, softening agents, rejuvenating agents and other suitable components.

Useful elastomers include, for example, ethylene-vinyl acetate copolymers, polybutadienes, ethylene-propylene copolymers, ethylene-propylene-diene terpolymers, reactive ethylene terpolymers (e.g. ELVALOY™), butadiene-styrene block copolymers, styrene-butadiene-styrene (SBS) block terpolymers, isoprene-styrene block copolymers and styrene-isoprene-styrene (SIS) block terpolymers, chloroprene polymers (e.g., neoprenes) and the like. Cured elastomer additives may include ground tire rubber materials.

In one embodiment, the binder includes a blend of binders. In certain embodiments, the binder blend includes virgin binder and binder extracted from reclaimed asphalt. For example, the binder extracted from RAS material may be extracted from manufacturer asphalt shingle waste, from consumer asphalt shingle waste, or from a mixture of binders extracted from manufacturer and consumer asphalt shingle waste. In certain embodiments, a binder blend may include from about 60 wt % to about 95 wt % of virgin binder and from about 5 wt % to about 40 wt % of binder extracted from reclaimed asphalt such as RAS. In certain embodiments, the binder blend includes the addition of an anti-aging additive from about 0.5 wt % to about 15.0 wt % of the virgin asphalt. In certain embodiments, the binder blend can include the addition of from about 0.2 wt % to about 1.0 wt % anti-aging additive. The anti-aging additive has been shown to improve high and low temperature properties and PG grading for both low and high temperature ends of RAS-containing asphalt binder blends.

The asphalt binder may be prepared by mixing or blending the crude sterol with the virgin binder to form a mixture or blend. The mixture or blend can be added to recycled asphalt materials (e.g. RAS and/or RAP) and aggregate. One of skill in the art will recognize that any sequences of adding and mixing components are possible. Asphalt can be prepared by applying mechanical or thermal convection. In one aspect, a method of preparing an asphalt involves mixing or blending a crude sterol with virgin asphalt at a temperature from about 100° C. to about 250° C. In some embodiments, the crude sterol is mixed with the virgin asphalt at a temperature from about 125° C. to about 175° C., or 180° C. to 205° C. In some embodiments, the asphalt is mixed with asphalt, crude sterol and softening agent. In still other embodiments, the asphalt is mixed with asphalt, RAS, RAP, or combinations of RAS and RAP, crude sterol and aggregate.

The disclosed asphalt can be characterized according to ASTM specifications and test methods, in addition to many standard tests. For example, the disclosed asphalts and binders can be characterized using rheological tests (viz., dynamic shear rheometer, rotational viscosity, and bending beam).

At low temperatures (e.g., −10° C.), road surfaces need cracking resistance. Under ambient conditions, stiffness and fatigue properties are important. At elevated temperature, roads need to resist rutting when the asphalt becomes too soft. Criteria have been established by the asphalt industry to identify rheological properties of a binder that correlate with likely paved road surface performance over the three common sets of temperature conditions.

To determine the $\Delta Tc$ parameter, a 4 mm dynamic shear rheometer (DSR) test procedure and data analysis methodology as described above can be used.

The $\Delta Tc$ parameter can also be determined using a BBR test procedure based on AASHTO T313 or ASTM D6648. It is important that when the BBR test procedure is used that the test is conducted at a sufficient number of temperatures such that results for the Stiffness failure criteria of 300 MPa and Creep or m-value failure criteria of 0.300 are obtained with one result being below the failure criteria and one result being above the failure criteria. In some instances for binders with $\Delta Tc$ values less than −5° C. this can require performing the BBR test at three or more test temperatures. $\Delta Tc$ values calculated from data when the BBR criteria requirements referred to above are not met may not be accurate.

Other anti-aging additives, preferably ones that can alter (e.g., reduce or retard) a binder aging rate, or can restore or renew an aged or recycled binder to provide some or all of the properties of a virgin binder may be able to be identified. For example, the $\Delta Tc$ for an asphalt containing an additive after aging may be determined; the $\Delta Tc$ for an asphalt without the additive is also analyzed and the results for the two $\Delta Tcs$ compared after aging of the asphalt with and without the additive. The asphalt with the additive that has a higher $\Delta Tc$ after 40 hours of PAV aging of at least 25% higher than the asphalt without the additive or a higher $\Delta Tc$ after 60 hours of PAV aging than the asphalt without the additive may be identified as an anti-aging additive.

In some embodiments, the additive can provide a higher $\Delta Tc$ after 40 hours of PAV aging of at least 35% higher, of at least 45% than the asphalt without the additive. In some embodiments the additive can provide a higher $\Delta Tc$ after 60 hours of PAV aging of at least 25% higher, of at least 35% or of at least 45% than the asphalt without the additive.

In one embodiment, the method to identify an anti-aging additive may include using for example PG 64-22 that has a $\Delta Tc$ after 40 hours of PAV aging of −5° C. or greater (e.g. −4, −3, etc.). About 8% Re-refined engine oil bottoms or about 5% paraffinic base oil may be added to the PG 64-22, RTFO aged, PAV aged for 20, 40 and 60 hours and determining $\Delta Tc$ after each aging step using either BBR or 4 mm DSR. This is followed by addition of about 5% or the manufacturer's recommend amount of an additive to the PG 64-22, and 8% re-refined engine oil bottoms or 5% paraffinic base oil. RTFO aging is followed by 20, 40 and 60 hours of PAV aging and the $\Delta Tc$ after each aging step is determined using either BBR or 4 mm DSR. An additive should be considered anti-aging at the dosage level used if the $\Delta Tc$ after 40 hours of PAV aging is at least 205% higher than the sample containing REOB or paraffinic base oil, but no rejuvenating additive. After 60 hours of PAV aging the additive could be considered anti-aging at the dosage level used if the $\Delta Tc$ after 60 hours of PAV aging is higher than the sample containing REOB or paraffinic base oil but no rejuvenating additive.

Pavement surface characteristics and changes in them can be revealed in an asphalt. These surface characteristics can be determined using atomic force microscopy (AFM). AFM is described for example in R. M. Overney, E. Meyer, J. Frommer, D. Brodbeck, R. Lüthi, L. Howald, H.-J. Güntherodt, M. Fujihira, H. Takano, and Y. Gotoh, "Friction Measurements on Phase-Separated Thin Films with a Modified Atomic Force Microscope", Nature, 1992, 359, 133-135; E. zer Muhlen and H. Niehus, "Introduction to Atomic Force Microscopy and its Application to the Study of Lipid Nanoparticles", Chapter 7 in Particle and Surface Characterization Methods, R. H. Muller and W. Mehnert Eds, Medpharm Scientific Pub, Stuttgart, 1997; and in H. Takano, J. R. Kenseth, S.-S. Wong, J. C. O'Brien, M. D. Porter, "Chemical and Biochemical Analysis Using Scanning Force Microscopy", Chemical Reviews 1999, 99, 2845-2890.

AFM is a type of scanning microscopy that provides high resolution, three-dimensional imaging at the atomic and molecular level. AFM can be used for both topographical imaging and force measurements. Topographical imaging involves scanning a cantilever/tip across the sample surface. A laser beam is reflected off the back of the cantilever, and small changes in cantilever deflection are detected with a position-sensitive photodiode detector. This deflection is processed by the system electronics to determine topological height changes on the sample surface. The basics of AFM and the origin of the topographic and friction signals are described in Overney et al. "Friction Measurements on Phase-Separated Thin Films with a Modified Atomic Force Microscope", Nature, 1992, 359, 133-135 (1992); Muhlen et al. "Introduction to Atomic Force Microscopy and its Application to the Study of Lipid Nanoparticles"; Chapter 7 "Particle and Surface Characterization Methods, R. H. Muller and W. Mehnert Eds, Medpharm Scientific Pub, Stuttgart, 1997; and Takano et al. "Chemical and Biochemical Analysis Using Scanning Force Microscopy", Chemical Reviews 1999, 99, 2845-2890 (1999)).

The surface defects may be measured as the surface roughness, expressed as average roughness over an image surface, based on the average height of the roughness extending out of the surface of the sample expressed in μm, and with the defect area (i.e. the non-smooth plane of the sample) expressed in μm2 and as a percent of the image area (e.g., as a percent of a 400 μm2image area). AFM can be used to determine the effects of the crude sterol on an asphalt as was used in the above-mentioned International Application No. PCT US2016/37077 and ALM0019/WO/2 filed herewith.

In some embodiments, a method for identifying aging in an asphalt and slowing the aging or restoring the aged asphalt includes analyzing an asphalt for the presence or absence of surface defects, wherein the asphalt is determined as aging if minimal surface defects are detected; and adding a sterol and virgin binder to the aged binder to reduce or slow the aging. In some embodiments, the aged asphalt include recycled asphalts, softening agents, and rejuvenating agents. For example, some asphalt include RAS, RAP, REOB, virgin paraffinic or naphthenic base oils, untreated or non-rerefined waste drain oils or waste engine oil materials, vacuum tower asphalt extenders, paraffinic or naphthenic processing oils and lubricating base oils. In some embodiments, the average roughness of an asphalt with sterol is 1.5 to 350 μm from 3.6 to 232 μm, or from 10 to 230 μm.

The present application is further illustrated in the following non-limiting examples, in which all parts and percentages are by weight unless otherwise indicated.

EXAMPLE 1

To investigate the efficacy of the anti-aging additive, four binders were produced and aged for 20 and 40 hours in the PAV (Pressured aging vessel) following ASTM D65217.

The binders were produced by mixing the components with a low shear Lightning mixer in a 1 gallon can at a temperature of 187.8° C.-204° C. (370-400° F.) for approximately 30 minutes. The test results for all binders used are shown in Table 3.

Sample #1 consisted of 80% PG 52-34 blended with 20% binder recovered from manufacturer's waste shingles obtained from Recovery Technology Solutions (RTS), Shakopee, MN and no sterol.

Sample #2 consisted of 90% PG 58-28 blended with 10% binder recovered from post-consumer waste shingles obtained from Recovery Technology Solutions (RTS), Shakopee, MN and contained no sterol.

Sample #3 consisted of 75% of a conventional PG 52-34 binder, 20% binder recovered from manufacturer's waste shingles obtained from Recovery Technology Solutions (RTS), Shakopee, MN and 5% mixed sterols obtained from MP Biomedicals (Catalog No. 02102886) referred to as beta-Sitosterol (beta-Sitosterol ~40-60%; campesterol ~20-40%; Stigmasterol ~5%).

Sample #4 consisted of 72.5% of a conventional PG 58-28 binder, 20% binder recovered from post-consumer waste shingles obtained from Recovery Technology Solutions (RTS), Shakopee, MN and 7.5% of mixed sterols obtained from MP Biomedicals (Catalog No. 02102886) referred to as beta-Sitosterol (beta-Sitosterol ~40-60%; campesterol ~20-40%; Stigmasterol ~5%).

The high temperature binder grade for binders in the unaged condition is the temperature at which the binder stiffness equals 1 kiloPascal (kPa) when tested in accordance with ASTM D7175. The high temperature stiffness grade for binders in all other aged conditions is the temperature at which the binder stiffness equals 2.2 kPa when tested in accordance with ASTM D7175. This convention is in keeping with typical SHRP PG grading practices. The results in Table 3 show that when no sterol is present in the sample the high temperature grade increases at a faster rate than when sterol is present. For Sample #1 the high temperature stiffness grade after the 20 hour PAV was 5.1° C. higher than Sample #3. After the 40 hour PAV the difference was 6.5° C., or one full PG grade greater in high the high temperature grade. For Sample #2 (with only 10% recovered shingle binder) with no sterol has a high temperature grade that is 3.2° C. higher than Sample #4 with 20% recovered shingle binder and 7.5% sterol after the 20 hour PAV and a stiffness grade 5.8° C. higher after the 40 hour PAV. The impact on low temperature properties is similar in scope. After 20 hours of PAV aging Sample #4 still has a positive ΔTc of 1.3° C. which is beneficial difference of 2.9° C. After 40 hours PAV aging the ΔTc of Sample #4 is ~1.9° C. which is 2.8° C. better than Sample #2. These are significant improvements considering that Sample #2 contained half the amount of recovered shingle binder as compared to Sample #4. The data summarized in Table 3 shows that not only does the use of sterol retard the impact of aging on low temperature properties, especially the critical relaxation property related to the m-value, but sterol addition also slows the rate at which the high temperature stiffness of the binder increases with age.

TABLE 3

| Binder | % RTS shingle binder | % Sterol | Aging | High Temp Grade | S-Critical Temp | m-Critical Temp | ΔTc |
|---|---|---|---|---|---|---|---|
| PG 52-34 | 20 | 0 | Unaged | 59.8 | −36.2 | −39.8 | 3.6 |
| PG 52-34 | 20 | 0 | RTFO | 60.7 | −37.0 | −38.2 | 1.2 |
| PG 52-34 | 20 | 0 | 20 hr. | 74.8 | −34.7 | −33.1 | −1.6 |
| PG 52-34 | 20 | 0 | 40 hr. | 83.2 | −34.3 | −29.6 | −4.7 |
| PG 58-28 | 10 | 0 | Unaged | 63.9 | −34.3 | −36.7 | 2.4 |
| PG 58-28 | 10 | 0 | RTFO | 66.5 | −32.2 | −33.1 | 0.9 |
| PG 58-28 | 10 | 0 | 20 hr. | 77.9 | −31.7 | −30.5 | −1.2 |
| PG 58-28 | 10 | 0 | 40 hr. | 87.2 | −30.0 | −26.0 | −4.0 |
| PG 52-34 | 20 | 5 | Unaged | 57.8 | −37.4 | −40.8 | 3.4 |
| PG 52-34 | 20 | 5 | RTFO | 57.8 | −36.6 | −39.5 | 2.9 |
| PG 52-34 | 20 | 5 | 20 hr. | 69.7 | −32.8 | −34.0 | 1.2 |
| PG 52-34 | 20 | 5 | 40 hr. | 76.7 | −33.5 | −31.6 | −1.9 |
| PG 58-28 | 20 | 7.5 | Unaged | 63.2 | −33.5 | −36.1 | 2.6 |
| PG 58-28 | 20 | 7.5 | RTFO | 64.0 | −32.7 | −35.6 | 2.9 |
| PG 58-28 | 20 | 7.5 | 20 hr. | 74.7 | −29.7 | −31.0 | 1.3 |
| PG 58-28 | 20 | 7.5 | 40 hr. | 81.4 | −27.5 | −26.4 | −1.0 |

EXAMPLE 2

To evaluate whether the use of mixed sterols could mitigate the excessive ΔTc results observed with REOB, three binder samples were evaluated. The samples were produced by mixing in a 1 quart can with a low shear Lightning mixer at a temperature of 300-325° F. for about 30 min. The REOB samples require less heat compared to the samples with recovered shingle binder as in Example 1.

Figure 1:
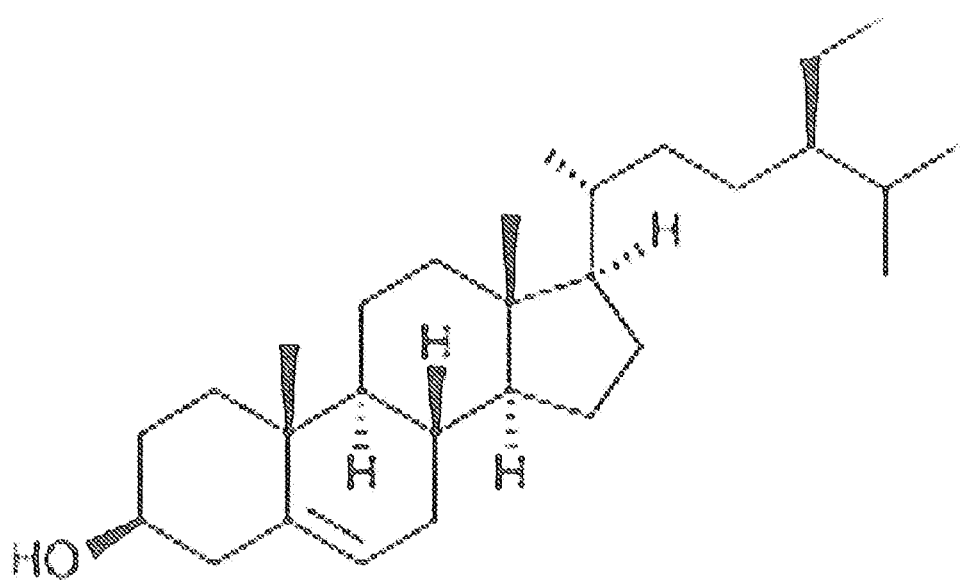
FIG. 1 depicts a representative plant sterol structure e.g., beta-sitosterol.
Figure 2:
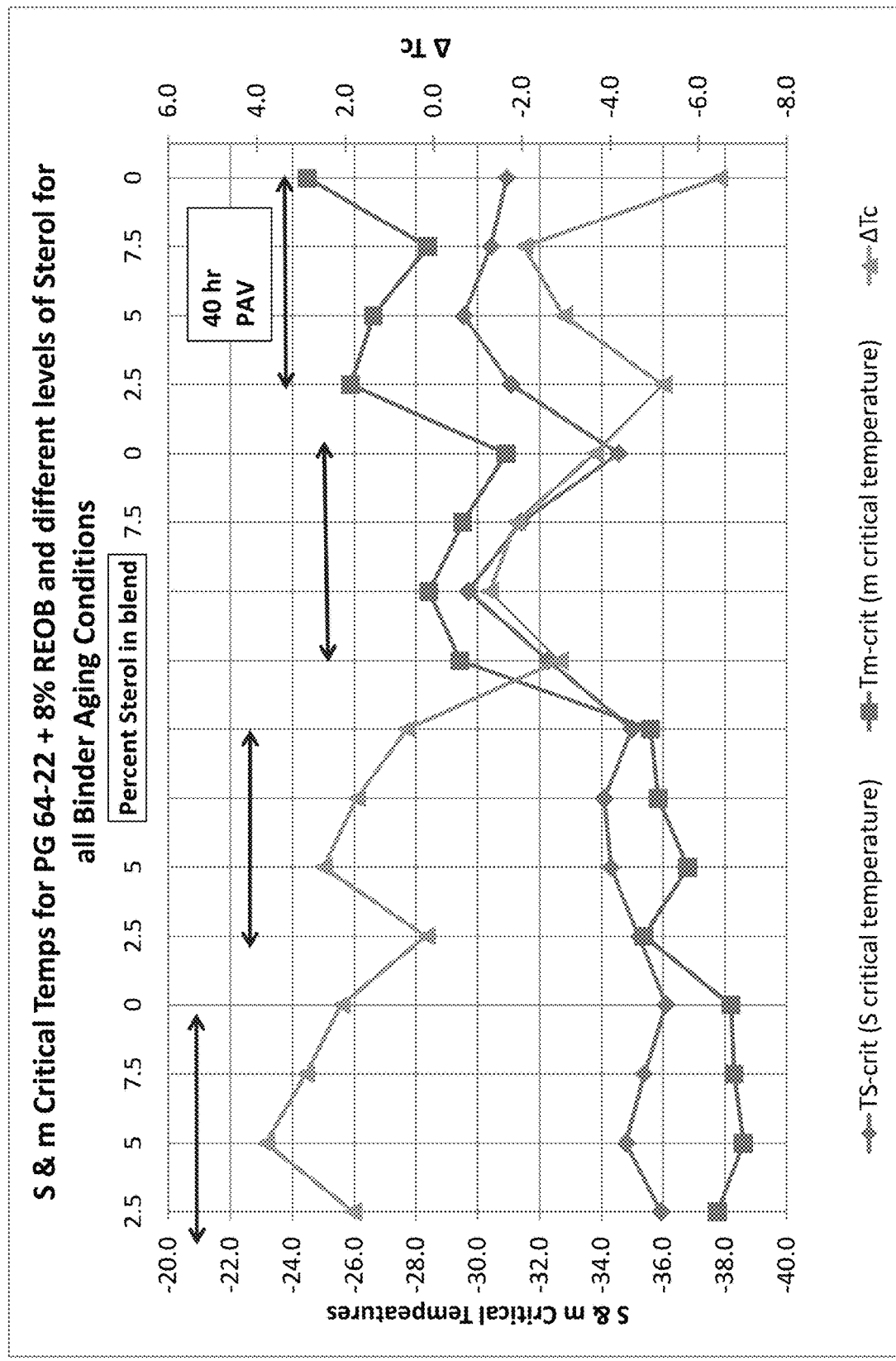
FIG. 2 is a graphical representation showing stiffness and creep temperature results for REOB samples with sterols.
Figure 3:
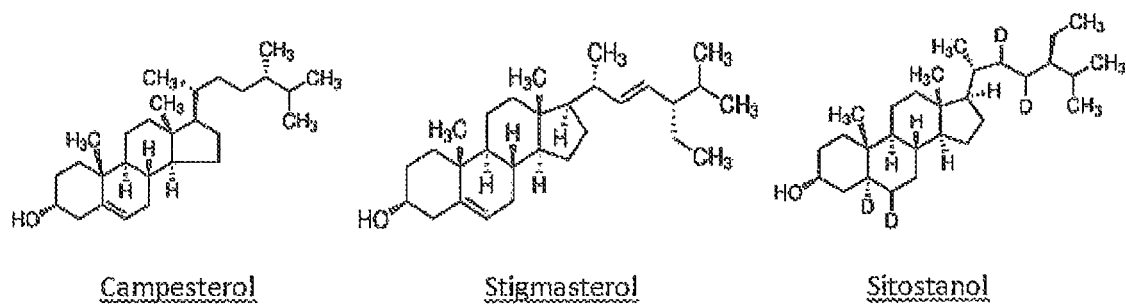
FIG. 3 shows exemplary plant sterols.

The results are shown in Table 4 and plotted in FIG. 2.

TABLE 4

| Sample description | Binder Aging | % Sterol | % REOB | S_critical | m_critical | ΔTc |
|---|---|---|---|---|---|---|
| RHEA G(t) @-24° C. 1531, 06-03-15-G, MIA 64-22 (Tk 6 Winter Fill), 8% REOB,, 4 mm, HR3-2, HR3-2 | unaged | 0 | 8 | −36.1 | −38.2 | 2.1 |
| G(t) @-30° C. 1531, RHEA G(t) @-24° C. 1531, 05-28-15-B, MIA 64-22 (Tk 6), 8% REOB, 5% Plant Sterols,, 4 mm, HR3-4 | unaged | 5 | 8 | −34.8 | −38.6 | 3.8 |
| RHEA G(t) @-24° C. 1531, 05-28-15-C, MIA 64-22 (Tk 6), 8% REOB, 7.5% Plant Sterols, 4 mm, HR3-2 | unaged | 7.5 | 8 | −35.4 | −38.3 | 2.9 |
| RHEA G(t) @-24° C. 1531, 06-03-15-G, MIA 64-22 (Tk 6 Winter Fill), 8% REOB,, 4 mm, HR3-2, HR3-2 | RTFO | 0 | 8 | −35.0 | −35.6 | 0.6 |
| G(t) @-30° C. 1531, RHEA G(t) @-24° C. 1531, 05-28-15-B, MIA 64-22 (Tk 6), 8% REOB, 5% Plant Sterols,, 4 mm, HR3-4 | RTFO | 5 | 8 | −34.3 | −36.8 | 2.5 |
| RHEA G(t) @-24° C. 1531, 05-28-15-C, MIA 64-22 (Tk 6), 8% REOB, 7.5% Plant Sterols, 4 mm, HR3-2 | RTFO | 7.5 | 8 | −34.1 | −35.8 | 1.8 |
| RHEA G(t) @-24° C. 1531, 06-03-15-G, MIA 64-22 (Tk 6 Winter Fill), 8% REOB,, 4 mm, HR3-2, HR3-2 | 20 hr. PAV | 0 | 8 | −34.6 | −30.9 | −3.6 |
| G(t) @-30° C. 1531, RHEA G(t) @-24° C. 1531, 05-28-15-B, MIA 64-22 (Tk 6), 8% REOB, 5% Plant Sterols,, 4 mm, HR3-4 | 20 hr. PAV | 5 | 8 | −29.7 | −28.4 | −1.3 |
| RHEA G(t) @-24° C. 1531, 05-28-15-C, MIA 64-22 (Tk 6), 8% REOB, 7.5% Plant Sterols, Unaged, 4 mm, HR3-2 | 20 hr. PAV | 7.5 | 8 | −31.4 | −29.5 | −1.9 |
| RHEA G(t) @-24° C. 1531, 06-03-15-G, MIA 64-22 (Tk 6 Winter Fill), 8% REOB,, 4 mm, HR3-2, HR3-2 | 40 hr. PAV | 0 | 8 | −30.9 | −24.5 | −6.5 |
| G(t) @-30° C. 1531, RHEA G(t) @-24° C. 1531, 05-28-15-B, MIA 64-22 (Tk 6), 8% REOB, 5% Plant Sterols,, 4 mm, HR3-4 | 40 hr. PAV | 5 | 8 | −29.6 | −26.6 | −2.9 |
| RHEA G(t) @-24° C. 1531, 05-28-15-C, MIA 64-22 (Tk 6), 8% REOB, 7.5% Plant Sterols,, 4 mm, HR3-2 | 40 hr. PAV | 7.5 | 8 | −30.4 | −28.4 | −2.0 |

As the binder aged, the ΔTc value for the samples with zero percent sterol exhibited the lowest value ΔTc. At 40 hr. PAV aging the ΔTc result for both the 5% and 7.5% sterol blends were greater than −3.0° C. while the zero percent sterol blend had a ΔTc value of −6.5° C.

EXAMPLE 3

To evaluate whether the use of mixed sterols could mitigate the excessive ΔTc results observed with REOB in binders, three samples were evaluated. The samples were produced by mixing in a 1 quart can with a low shear Lightning mixer at a temperature of 300-325° F. for about 30 min. The REOB samples require less heat compared to the samples with recovered shingle binder as in Example 1. The mixed sterols used are the same as those described in Example 1.

The binder used in this is example was one of four binders used on a research project on County Trunk Highway 112 in Olmsted County, MN that was constructed in 2006. Three other binders from other crude sources were also evaluated using identical aggregate blends. The test section containing the MN1-4 binder performed significantly more poorly than the other test sections and MN1-4 contained REOB. The REOB content was not specifically provided, but testing for the zinc content of the binder indicated that the REOB content would have been in the range of 8% to 9%.

Using the MN1-4 binder samples were produced using 5% and 7.5% sterol and aged for 20, 40 and 60 hours of PAV conditioning. Low temperature properties and ΔTc values were measured using the 4 mm DSR test procedure for an unaged, RTFO, 20, 40 and 60 hour PAV aging conditions.

Table 5 shows the comparison of total distress data obtained by an independent survey versus 40 hour PAV ΔTc data for the CTH 112-test sections. Test results for the of 5% and 7.5% sterol blends with MN1-4 binder and aged for 40 and 60 hours in the PAV are also shown.

Figure 4:
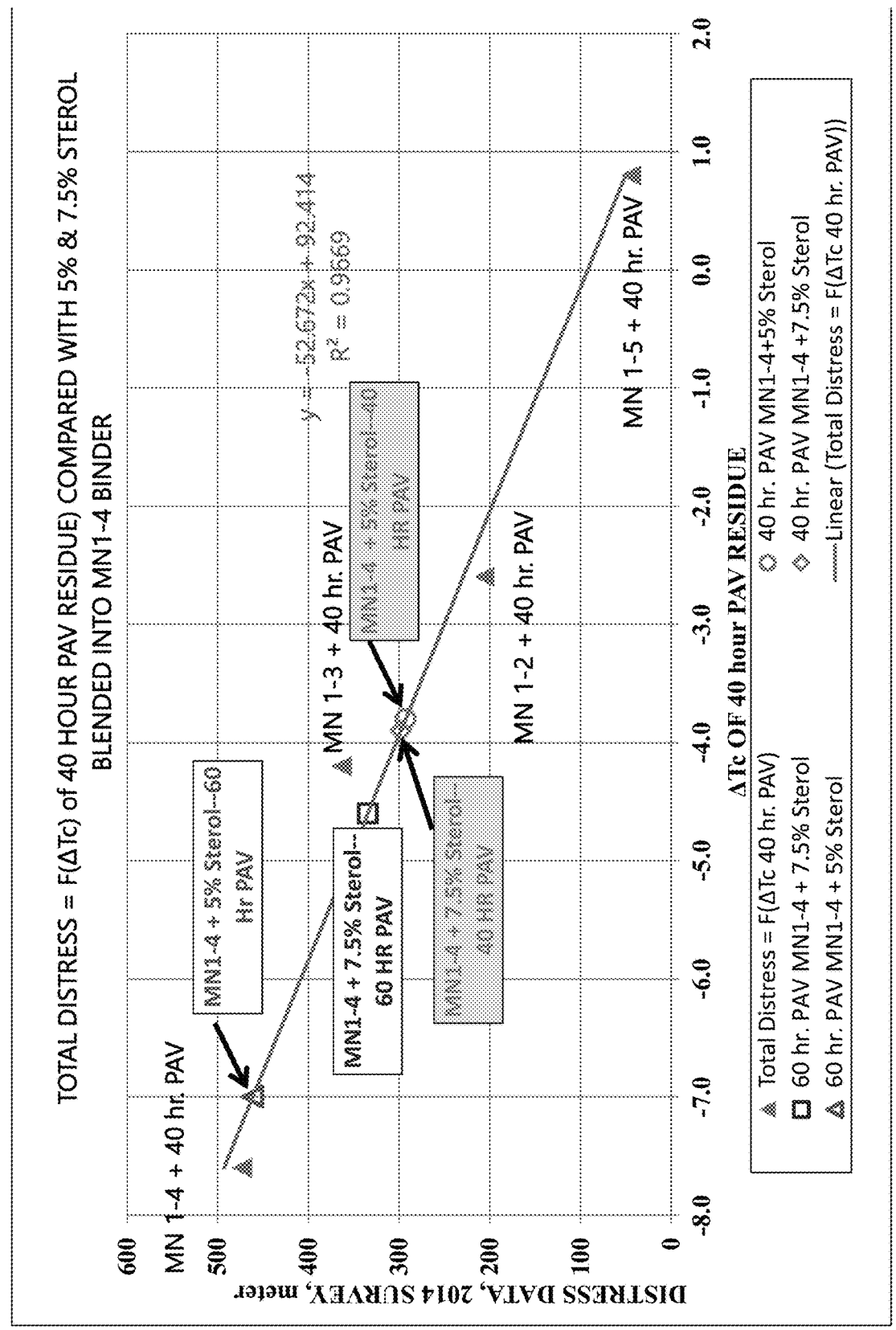
FIG. 4 is a graphical representation showing a change in ΔTc with level of sterol and binder aging.

The data in Table 5 are also plotted in FIG. 4.

values greater than (less negative) than the 40 hour PAV of untreated MN1-4. In a direct comparison of the ΔTc values for 40 hour PAV residues the sterol treated MN1-4 had values approximately half of the untreated MN1-4 binder. The results shown in FIG. 4 suggest that had 5% sterol been used in the MN1-4 along with the REOB the pavement performance after eight years in service could have been comparable to that of the MN1-3 binder.

EXAMPLE 4

To further evaluate the role of sterols on the aging characteristics of binders with reclaimed asphalt binder shingles, four samples were evaluated: a control binder and two binders blended with commercial bio-derived oils that are promoted as rejuvenating additives for use with high levels of RAP and/or RAS. The four binders were:

1. A control binder PG 52-34 with no additive
2. PG 52-34+5% mixed sterols
3. PG 58-28+5% EVOFLEX PC2106 marketed by Ingevity
4. PG 58-28+5% RS1100 marketed by Arizona Chemical To investigate the impact of reclaimed asphalt shingles on the aging characteristics of binders the binders detailed above were used to produce bituminous mixtures containing 5% RAS which were subjected to 24 hours of loose mix aging at 135° C. After this aging step the binders were extracted and recovered and tested for low temperature properties and ΔTc was calculated The samples were produced by mixing in a one quart can with a low shear Lightning mixer at a temperature of 148.9° C.-162.8° C. (300-325° F.) for about 30 min.

The samples that were produced so that the high temperature PG grade of all four binders would be approximately the same. Because the use of 5% bio-derived oil

TABLE 5

| | | | ΔTc for Sterol blends in MN1-4 aged for 40 and 60 hour PAV | | | |
|---|---|---|---|---|---|---|
| Binder | TOTAL DISTRESS | ΔTc 40 Hr. PAV | MN1-4 + 5% Sterol 40 hr. PAV | MN1-4 + 7.5% Sterol 40 hr. PAV | MN1-4 + 7.5% Sterol 60 hr. PAV | MN1-4 + 5% Sterol 60 hr. PAV |
| MN1-2 | 205.9 | −2.6 | | | | |
| MN1-3 | 363.4 | −4.2 | | | | |
| MN1-4 | 472.6 | −7.6 | −3.8 | −3.9 | −4.6 | −7.0 |
| MN1-5 | 44.1 | 0.8 | | | | |

Binder MN1-2 is a polymer modified PG 58-34 produced with a blend of western Canadian crudes; MN1-3 is a PG 58-28 binder from a Minnesota refinery using a blend of western Canadian crudes; MN1-4 is from a Texas refinery using a blend of Middle East crudes from Kirkuk and MN-1-1 is PG 58-34. MN1-4 contained REOB.

Only samples of MN1-4 treated with 5% and 7.5% sterol and aged for 40 and 60 hours in the PAV all exhibited ΔTc typically reduces the high temperature PG grade by 6° C. or more a PG 58-28 binder was used with the PC2106 and the RS1100.

The high temperature PG grade of each binder following ASTM D7175 or AASHTO T315 and the low temperature properties as determined from the 4 mm DSR test after 20 hours of PAV aging are shown in Table 6.

TABLE 6

| Sample | High Temp Pg Grade Unaged Binder | 20 Hr. PAV, 4 mm S Critical Grade | 20 Hr. PAV, 4 mm m Critical Grade | Low temperature grade by 4 mm DSR | ΔTc 20 HR. PAV Binder |
|---|---|---|---|---|---|
| PG 52-34 Control | 54 | −35.76 | −35.89 | −35.8 | 0.1 |
| 52-34 + 5% Sterols | 52.7 | −34.37 | −34.80 | −34.4 | 0.4 |
| PG 58-28 + 5% Evoflex PC2106 | 51.7 | −34.44 | −33.97 | −34.0 | −0.5 |
| PG 58-28, 5%, AZ Chemical RS1100 | 49.6 | −36.96 | −36.69 | −36.7 | −0.3 |

The data in Table 6 shows that although two different starting binders were used once the samples were produced with the bio-derived oils, the high temperature PG grades were nearly the same and in fact the bio-derived oil blends were slightly lower in stiffness. Conventional low temperature PG grading is determined on the binder after the 20 hour PAV aging procedure.

The low temperature PG grade data in Table 6 showed that all four binders met a PG grade of −34. Therefore prior to producing the bituminous mixtures with the 5% RAS and prior to the 24 hour aging, the mixtures had been produced with binders of very similar high and low PG grade values.

Further each unaged binder was mixed with a typical dense graded aggregate suitable for paving a road designed to carry a designed traffic life of 3 million Equivalent Single Axel Loads (ESALs) with the addition of 5% RAS. The 5% RAS contained sufficient binder to provide approximately 20% binder replacement in the mixture. Such a level of RAS in paving mixtures is currently a well-accepted practice in the bituminous paving industry. Each 3000 gram mixture was produced by blending 5% of the RAS with 95% of the 12.5 mm nominal maximum sized aggregate. The total binder content required for the mix was 5.7% but since 20% of the binder content came from the RAS, only 4.56% of each of the binder samples was added by weight of the total mix.

The mixes were produced in a bucket mixer at a target temperature of 162.8° C. (325° F.) with two minutes of mixing time and then each was placed in a pan in a layer approximately 18 inches by approximately 12 inches by approximately 2.5 inches thick. The mix was not compacted but placed in loose condition in the pan. The pans were placed in a Blue M model 166 forced draft oven at 135° C. (275° F.) and held at that temperature for 24 hours. After this period, the mixes were removed, allowed to cool to room temperature and then the binder was extracted from the mixtures using a centrifugal extractor with toluene as the solvent to remove the binder. Recovery of the extracted asphalt was accomplished using a Buchi rotary evaporator following ASTM D7906-14, Standard Practice for Recovery of Asphalt binder from Solution Using Toluene and the Rotary Evaporator. Following recovery the 4 mm DSR test was performed. The ΔTc properties of the binders recovered from the mixtures aged for 24 hours at 135° C. was determined using the 4 mm DSR. The results of those tests are shown in Table 7.

TABLE 7

| Sample | ΔTc UNAGED BINDER | ΔTc RTFO BINDER | ΔTc 20 HR. PAV BINDER | ΔTc 40 HR. PAV BINDER | ΔTc Recovered binder from 5% RAS mix aged 24 hr. @ 135° C. (275° F.) |
|---|---|---|---|---|---|
| PG 52-34 Control | 2.7 | 1.9 | 0.1 | −1.6 | −15.1 |
| 52-34 + 5% Sterols | 2.2 | 1.5 | 0.4 | 0.5 | −8.4 |
| PG 58-28 + 5% Evoflex PC2106 | 2.1 | 2.0 | −0.5 | −1.2 | −15.4 |
| PG 58-28, 5% AZ Chemical RS1100 | 3.0 | 2.2 | −0.3 | −0.3 | −14.0 |

The data in Table 7 shows that through 40 hours of PAV aging there is little difference between the low temperature S-Critical and m-critical grades and the ΔTc properties of the four binders. However Table 8 shows that once the RAS containing mixtures were produced, aged and then the binder recovered and tested it was clear that the sterol-blended binder resisted the aging and loss of binder relaxation that is characteristic of aged RAS mixtures. It should be further noted that this resistance to aging is not a function of the base binder used to produce the mixtures. The base binder used for the Evoflex PC2106 and AZ Chemical RS1100 was a PG 58-28 while the control binder and the binder used in the sterol blend was a PG 52-34. Regardless of the base binder the samples that did not contain sterol had substantially higher high temperature PG values and ΔTc values nearly twice that of the sterol blend as detailed in Table 8

Further Table 8 shows that the 24 hour, 135° C. (275° F.) conditioning had the greatest impact on the m-value Critical Temperature value when compared to the Stiffness and m-value critical data shown in Table 7. Additionally Table 8 shows that the main impact of the plant sterol additive is its ability to retard the loss of binder relaxation due to aging. Further the high temperature PG grades of the PG 52-34 control binder and the binders produced with bio derived oils are similar indicating that those additives did not function as rejuvenating materials at either high or low temperatures.

Mexican asphalt binder designated as Asphalto 64-22 and similar blends were produced using the domestically produced PG 64-22. In total 6 binder samples were evaluated. The samples were produced as described in Example 1 and the sterols used are the same as were described in Example 1.

1. A control sample of Asphalto 64-22 with no additive
2. Asphalto 64-22+5% mixed sterols
3. Asphalto 64-22+7.5% mixed sterols
4. A control sample of domestic PG 64-22 with no additive
5. Domestic PG 64-22+5% mixed sterols
6. Domestic PG 64-22+7.5% mixed sterols

TABLE 8

| Sample | Recovered binder from 5% RAS mix aged 24 hr. @ 135° C.-- High Temp PG Grade | Recovered binder from 5% RAS mix aged 24 hr. @ 135° C.-- 4 mm S Critical Grade | Recovered binder from 5% RAS mix aged 24 hr. @ 135° C.-- 4 mm m Critical Grade |
|---|---|---|---|
| PG 52-34 Control | 122.6 | −32.20 | −17.07 |
| 52-34 + 5% Sterols | 112.6 | −29.59 | −21.15 |
| PG 58-28 + 5% Evoflex PC2106 | 129.6 | −26.07 | −10.65 |
| PG 58-28, 5% RS1100 | 125.4 | −27.79 | −13.74 |

The high temperature grade of the sterol blend is 10° C. to 17° C. below the high temperature grades of the other recovered binders, which amounts to 1.5 and nearly 3 full PG grade changes between the sterol blended binder and the other binder samples. Using the 20 hour PAV aging low temperature data (Table 7) as a basis of comparison the stiffness critical values have increased by 3.6° C. (PG 52-34 control) to as much as 8.9° C. (RS1100 blend), but the m-value critical values have increased by 18.8° C. (for the PG 52-34 control, 13.6° C. (for the Sterol blend) to 23° C. for the two bio-derived oil blends. The conclusions drawn from this example are the relaxation properties are impacted more substantially by the presence of the RAS combined with the mixture aging and the sterol containing mixture was impacted the least at both the high and low temperature properties compared to the other binders.

EXAMPLE 5

A sample of PG 64-22 asphalt binder from Pemex Refinery in Mexico using Mayan crude was found to have very poor aging properties when subjected to up to 60 hours of PAV aging as compared to a PG 64-22 obtained from a domestic US refinery using Canadian crude. Samples were produced by adding 5% and 7.5% mixed Sterols to the Binders were tested in unaged, RTFO, 20 hour PAV, 40 hour PAV and 60 hour PAV aged condition. High and low temperature PG grades were determined. The low temperature results were obtained using the 4 mm DSR procedure previously described. High temperature grade was determined following ASTM D7175. Also determined was the ΔTc result at all aging conditions based on the 4 mm DSR data. Also calculated was the Rheological Index also known as R-Value from the 4 mm DSR data. Compositional data from binders in all aged conditions was measured using the Iatroscan procedure and the Colloidal Index calculated from the data. The data for all tests are summarized in Tables 9, Table 10, Table 11 and Table 12.

As a general trend, as asphalt binders age the R-value increases because of decreased ability to relax stress and the Colloidal Index decreases because the amount of asphaltenes increase while saturates remain mostly unchanged and the cyclics decrease with only modest increases in resins. Inspection of the data in Table 9 showed that as the Asphalto 64-22 binder samples with 0%, 5% and 7.5% sterol is successively more aged as the R-Value increases and the Colloidal Index decreases.

TABLE 9

Iatroscan Test Results

| Base Sample | Aging Condition | 4 mm R-value | Asphaltenes | Resins | Cyclics | Saturates | CI |
|---|---|---|---|---|---|---|---|
| Asfalto 64-22 | unaged | 2.366 | 19.6 | 23.3 | 51.0 | 6.2 | 2.880 |
| Asfalto 64-22 | RTFO | 2.915 | 22.2 | 24.0 | 47.0 | 6.7 | 2.457 |
| Asfalto 64-22 | 20 hr. PAV | 3.609 | 26.9 | 27.8 | 38.7 | 6.5 | 1.991 |
| Asfalto 64-22 | 40 hr. PAV | 4.337 | 29.6 | 31.7 | 31.7 | 6.9 | 1.737 |
| Asfalto 64-22 | 60 hr. PAV | 4.732 | 32.7 | 28.8 | 30.5 | 8.0 | 1.457 |
| Asfalto 64-22, 5% sitosterol | unaged | 1.947 | 19.0 | 28.0 | 45.9 | 7.2 | 2.821 |
| Asfalto 64-22, 5% sitosterol | RTFO | 2.561 | 22.8 | 27.5 | 42.7 | 7.0 | 2.356 |
| Asfalto 64-22, 5% sitosterol | 20 hr. PAV | 2.923 | 25.9 | 32.4 | 34.9 | 6.7 | 2.064 |
| Asfalto 64-22, 5% sitosterol | 40 hr. PAV | 3.319 | 27.4 | 35.7 | 29.4 | 6.7 | 1.909 |
| Asfalto 64-22, 5% sitosterol | 60 hr. PAV | 3.764 | 30.4 | 34.3 | 28.2 | 7.1 | 1.667 |
| Asfalto 64-22, 7.5% sitosterol | unaged | 1.970 | 18.4 | 29.9 | 44.6 | 7.1 | 2.922 |
| Asfalto 64-22, 7.5% sitosterol | RTFO | 2.257 | 21.5 | 29.7 | 41.9 | 6.8 | 2.530 |
| Asfalto 64-22, 7.5% sitosterol | 20 hr. PAV | 2.687 | 25.1 | 34.7 | 33.4 | 6.7 | 2.142 |
| Asfalto 64-22, 7.5% sitosterol | 40 hr. PAV | 3.102 | 27.6 | 36.9 | 29.0 | 6.6 | 1.927 |
| Asfalto 64-22, 7.5% sitosterol | 60 hr. PAV | 3.292 | 29.5 | 36.6 | 27.0 | 7.1 | 1.738 |

Table 10 showed a steady decrease in the value of ΔTc for each sterol dosage level, but much less of a decrease for the 5% and 7.5% blends.

TABLE 10

| Base Sample | Aging Condition | S_critical | m_critical | ΔTc |
|---|---|---|---|---|
| Asfalto 64-22 | unaged | −35.6 | −34.6 | −1.0 |
| Asfalto 64-22 | RTFO | −32.5 | −29.9 | −2.6 |
| Asfalto 64-22 | 20 hr. PAV | −30.0 | −23.1 | −7.0 |
| Asfalto 64-22 | 40 hr. PAV | −29.3 | −16.9 | −12.4 |
| Asfalto 64-22 | 60 hr. PAV | −28.1 | −9.9 | −18.2 |
| Asfalto 64-22, 5% sitosterol | unaged | −33.2 | −33.1 | −0.1 |
| Asfalto 64-22, 5% sitosterol | RTFO | −31.0 | −29.7 | −1.3 |
| Asfalto 64-22, 5% sitosterol | 20 hr. PAV | −28.6 | −25.6 | −3.0 |
| Asfalto 64-22, 5% sitosterol | 40 hr. PAV | −26.6 | −21.9 | −4.7 |
| Asfalto 64-22, 5% sitosterol | 60 hr. PAV | −27.6 | −17.1 | −10.5 |
| Asfalto 64-22, 7.5% sitosterol | unaged | −33.5 | −33.7 | 0.2 |
| Asfalto 64-22, 7.5% sitosterol | RTFO | −30.6 | −29.9 | −0.7 |
| Asfalto 64-22, 7.5% sitosterol | 20 hr. PAV | −27.3 | −25.0 | −2.3 |
| Asfalto 64-22, 7.5% sitosterol | 40 hr. PAV | −27.0 | −23.1 | −3.9 |
| Asfalto 64-22, 7.5% sitosterol | 60 hr. PAV | −25.8 | −20.2 | −5.6 |

TABLE 11

| Sample | Aging Condition | 4 mm_Rvalue | Asphaltenes | Resins | Cyclics | Saturates | CI |
|---|---|---|---|---|---|---|---|
| PG 64-22, 0% Sterol | Unaged | 1.464 | 14.8 | 26.9 | 53.9 | 4.4 | 4.208 |
| Tank 6, 64-22 | RTFO | 1.721 | 16.9 | 29.5 | 49.2 | 4.4 | 3.695 |
| Tank 6, 64-22 | 20 hr. PAV | 2.149 | 23.5 | 32.6 | 38.2 | 4.2 | 2.556 |
| Tank 6, 64-22 | 40 hr. PAV | 2.363 | 26.6 | 33.8 | 35.2 | 4.5 | 2.219 |
| Tank 6, 64-22 new run on May 11, 2016 | 60 hr. PAV | 2.909 | 29.8 | 33.2 | 31.4 | 5.6 | 1.825 |
| PG 64-22, 5% sterol | Unaged | 1.313 | 13.2 | 32.4 | 49.1 | 5.3 | 4.405 |
| Tk 6, 64-22, 5% sitosterol | RTFO | 1.486 | 16.8 | 32.9 | 44.8 | 4.8 | 3.597 |

TABLE 11-continued

| Sample | Aging Condition | 4 mm_Rvalue | Asphaltenes | Resins | Cyclics | Saturates | CI |
|---|---|---|---|---|---|---|---|
| Tk 6, 64-22, 5% sitosterol | 20 hr. PAV | 1.899 | 22.0 | 37.4 | 35.9 | 4.7 | 2.745 |
| Tk 6, 64-22, 5% sitosterol | 40 hr. PAV | 2.196 | 25.4 | 38.6 | 31.0 | 5.0 | 2.289 |
| Tk 6, 64-22, 5% sitosterol | 60 hr. PAV | 2.422 | 27.4 | 39.3 | 28.4 | 5.1 | 2.083 |
| PG 64-22, 7.5% sterol | Unaged | 1.387 | 14.4 | 34.2 | 46.4 | 5.0 | 4.155 |
| Tk 6, 64-22, 7.5% sitosterol | RTFO | 1.500 | 17.3 | 35.5 | 42.5 | 4.7 | 3.545 |
| Tk 6, 64-22, 7.5% sitosterol | 20 hr. PAV | 1.817 | 21.7 | 39.7 | 33.8 | 4.7 | 2.784 |
| Tk 6, 64-22, 7.5% sitosterol | 40 hr. PAV | 1.995 | 24.1 | 41.9 | 29.3 | 4.7 | 2.472 |
| Tk 6, 64-22, 7.5% sitosterol | 60 hr. PAV | 2.228 | 26.4 | 41.7 | 27.2 | 4.7 | 2.215 |

TABLE 12

| Sample | Aging Condition | S_critical | m_critical | ΔTc |
|---|---|---|---|---|
| Tank 6, 64-22 | Unaged | −30.5 | −32.7 | 2.2 |
| Tank 6, 64-22 | RTFO | −27.1 | −28.1 | 1.0 |
| Tank 6, 64-22 | 20 hr. PAV | −24.9 | −24.0 | −0.9 |
| Tank 6, 64-22 | 40 hr. PAV | −23.7 | −22.2 | −1.4 |
| Tank 6, 64-22 | 60 hr. PAV | −23.2 | −18.6 | −4.6 |
| Tk 6, 64-22, 5% sitosterol | Unaged | −29.5 | −31.8 | 2.3 |
| Tk 6, 64-22, 5% sitosterol | RTFO | −27.1 | −28.9 | 1.8 |
| Tk 6, 64-22, 5% sitosterol | 20 hr. PAV | −24.8 | −25.3 | 0.5 |
| Tk 6, 64-22, 5% sitosterol | 40 hr. PAV | −23.5 | −23.4 | −0.2 |
| Tk 6, 64-22, 5% sitosterol | 60 hr. PAV | −21.4 | −20.0 | −1.4 |
| Tk 6, 64-22, 7.5% sitosterol | Unaged | −30.5 | −32.7 | 2.2 |
| Tk 6, 64-22, 7.5% sitosterol | RTFO | −26.9 | −28.4 | 1.5 |
| Tk 6, 64-22, 7.5% sitosterol | 20 hr. PAV | −23.9 | −25.2 | 1.4 |
| Tk 6, 64-22, 7.5% sitosterol | 40 hr. PAV | −23.0 | −22.1 | −0.8 |
| Tk 6, 64-22, 7.5% sitosterol | 60 hr. PAV | −21.9 | −20.7 | −1.2 |

Figure 5:
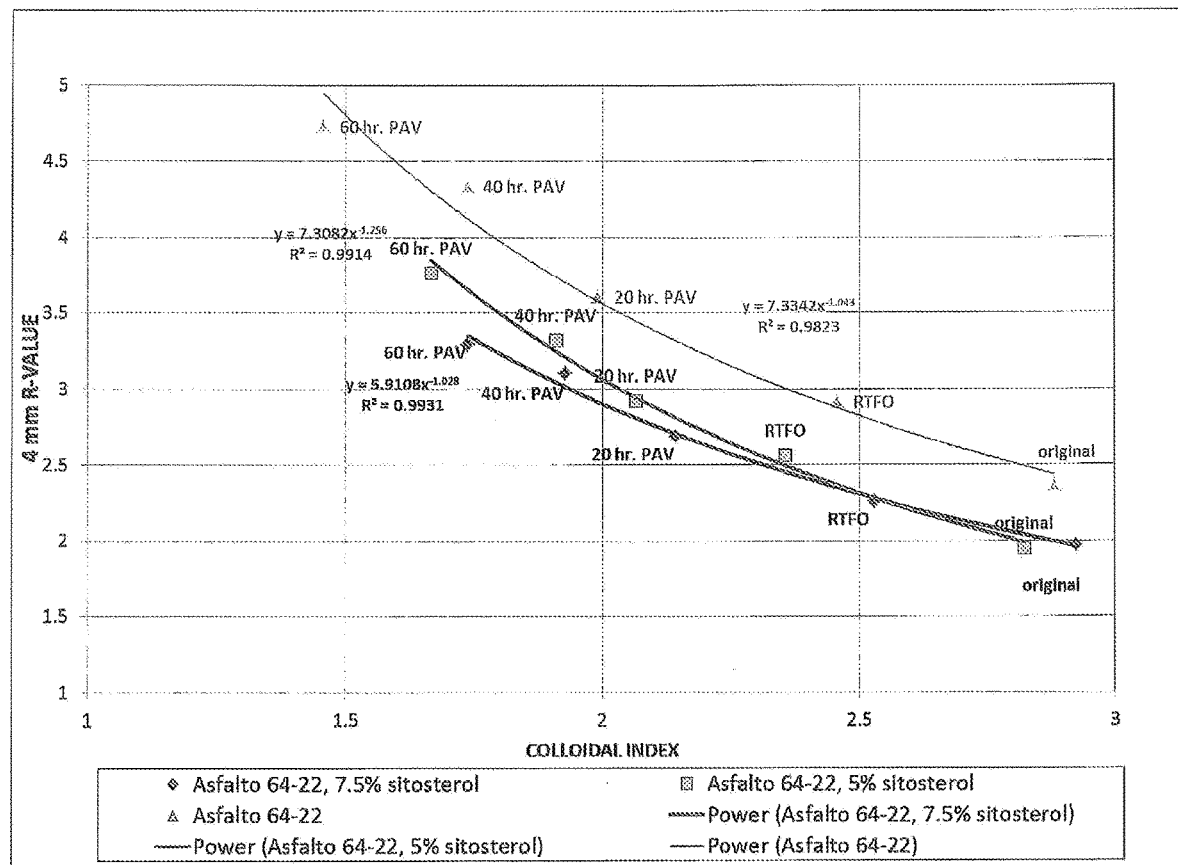
FIG. 5 is a graphical representation of R-value versus Colloidal Index for Mayan crude based Asphalto 64-22 aged through 60 hours in the PAV and for samples containing no sterol, 5% sterol, and 7.5% sterol.
Figure 6:
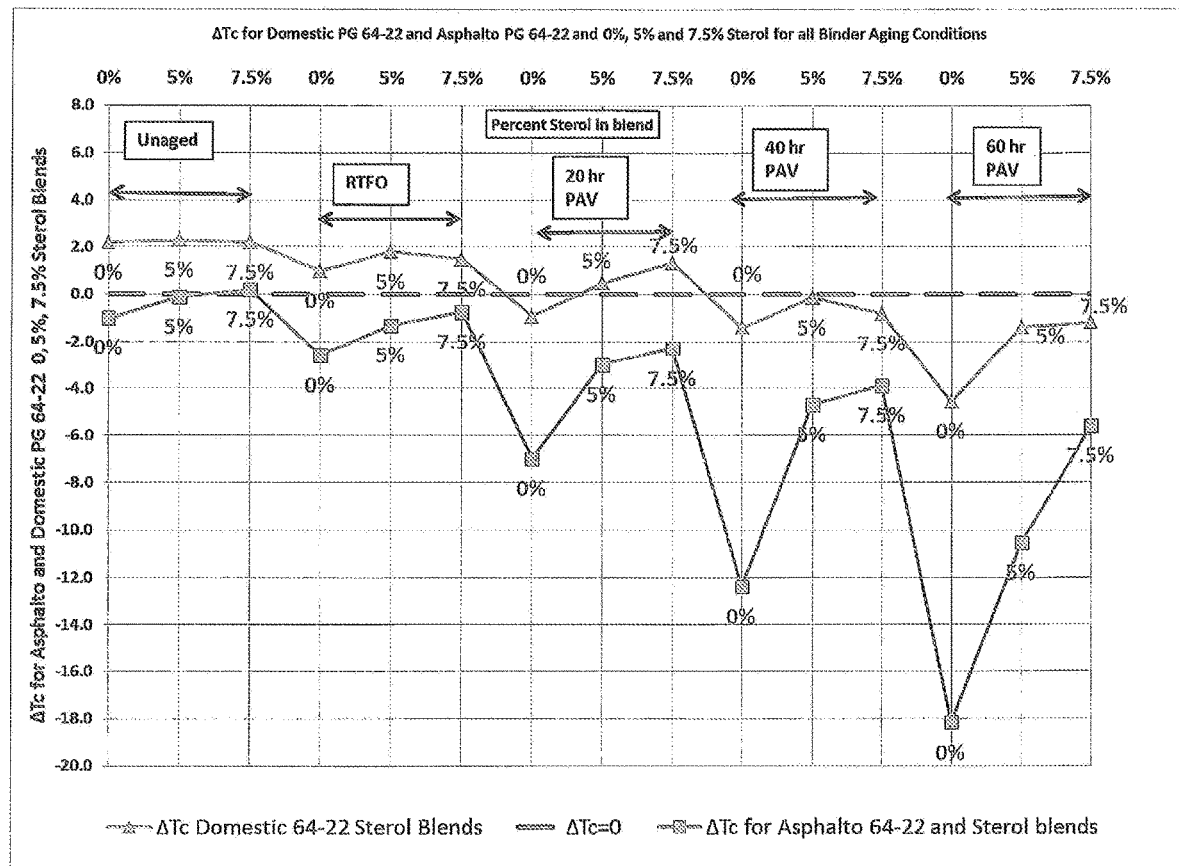
FIG. 6 is a graphical representation showing variation in ΔTc for Mayan crude Asphalto 64-22 and Canadian crude based PG 64-22 through 60 hours of PAV aging and 0% blended sterol, 5% blended sterol and 7.5% blended sterol for both binders.
Figure 7:
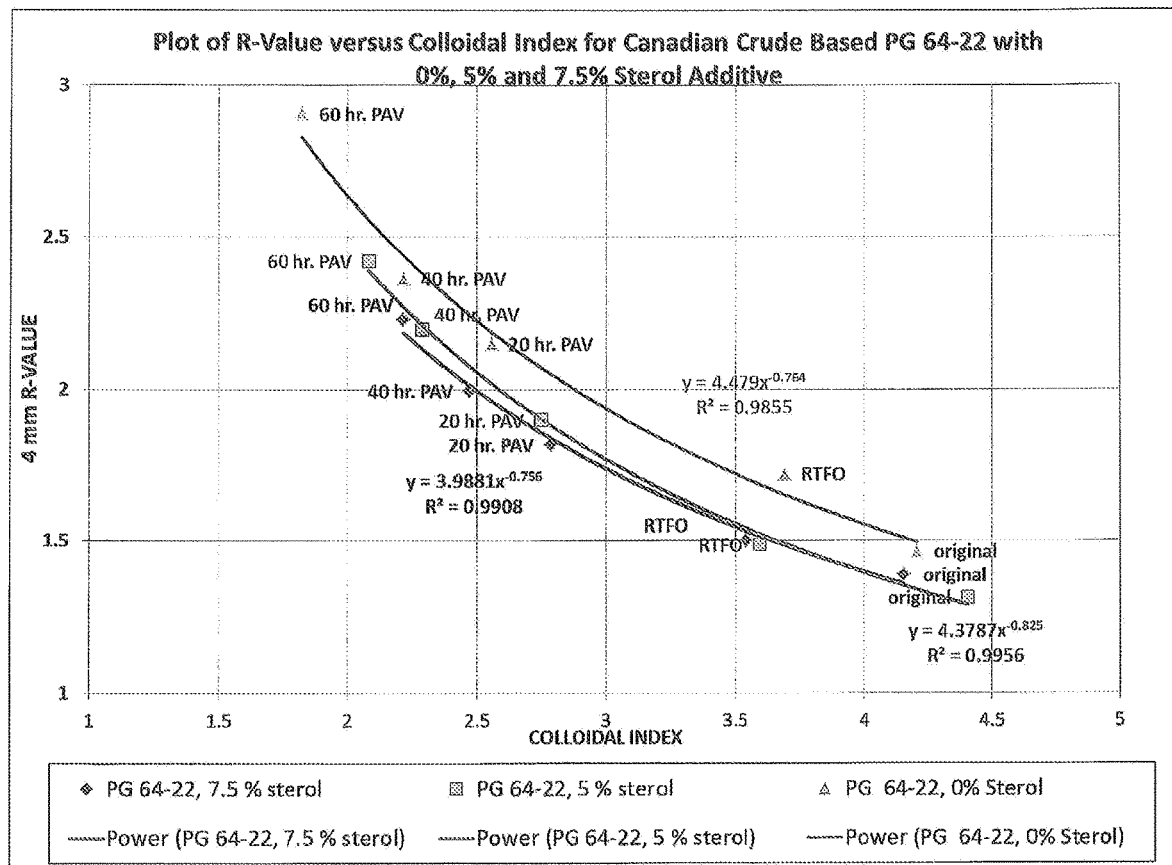
FIG. 7 is a graphical representation of R-value versus Colloidal Index for Canadian crude based PG 64-22 through 60 hours of PAV aging and containing 0% blended sterol, 5% blended sterol, and 7.5% blended sterol.

These trends are illustrated in FIGS. 5, 6 and 7. The data plotted in FIG. 5 showed the relationship between R-Value and Colloidal Index plots sustainably higher in R-Value for every value of Colloidal Index for the 0% sterol blend. The 5% and 7.5% sterol blends have R-Values that are 0.5 or more lower than the corresponding R-Values for the 0% sterol blend. The data also shows that after 20 hours of PAV aging there is a decrease in the R-value for the 7.5% sterol blend compared to the 5% sterol blend thus indicating that there is a dose response effect with the sterol additive for the Asphalto 64-22 binder. Since the colloidal index was a chemical constituent determination and the R-Value was rheological determination the high level of correlation between these two parameters suggests that the impact of the sterol has chemical compositional as well as a rheological basis.

FIG. 6 is a plot of the ΔTc data obtained from the 4 mm DSR test for the unaged, RTFO, 20 hour PAV, 40 hour PAV and 60 hour PAV conditions for the 0%, 5% and 7.5% sterol levels for both the Mayan Crude based Asphalto 64-22 and the Canadian Crude based PG 64-22. The Asphalto 64-22 which exhibited significant decrease in ΔTc with aging was significantly improved with the addition of the sterol additive and again a dose response effect was seen for the Asphalto 64-22 binder although the greatest impact was seen at the 60 hour PAV aged condition. The Canadian Crude based PG 64-22, which does not have a serious problem with negative values of ΔTc also exhibited some improvement in ΔTc with aging, but the effect was much less pronounced.

This comparative analysis of the impact of the sterol additive on asphalt binder binders which exhibit marked differences due to aging suggest that the benefits of the sterol additive are most likely to be of value in asphalt binders that exhibit these large decreases in ΔTc with aging.

Figure 8:
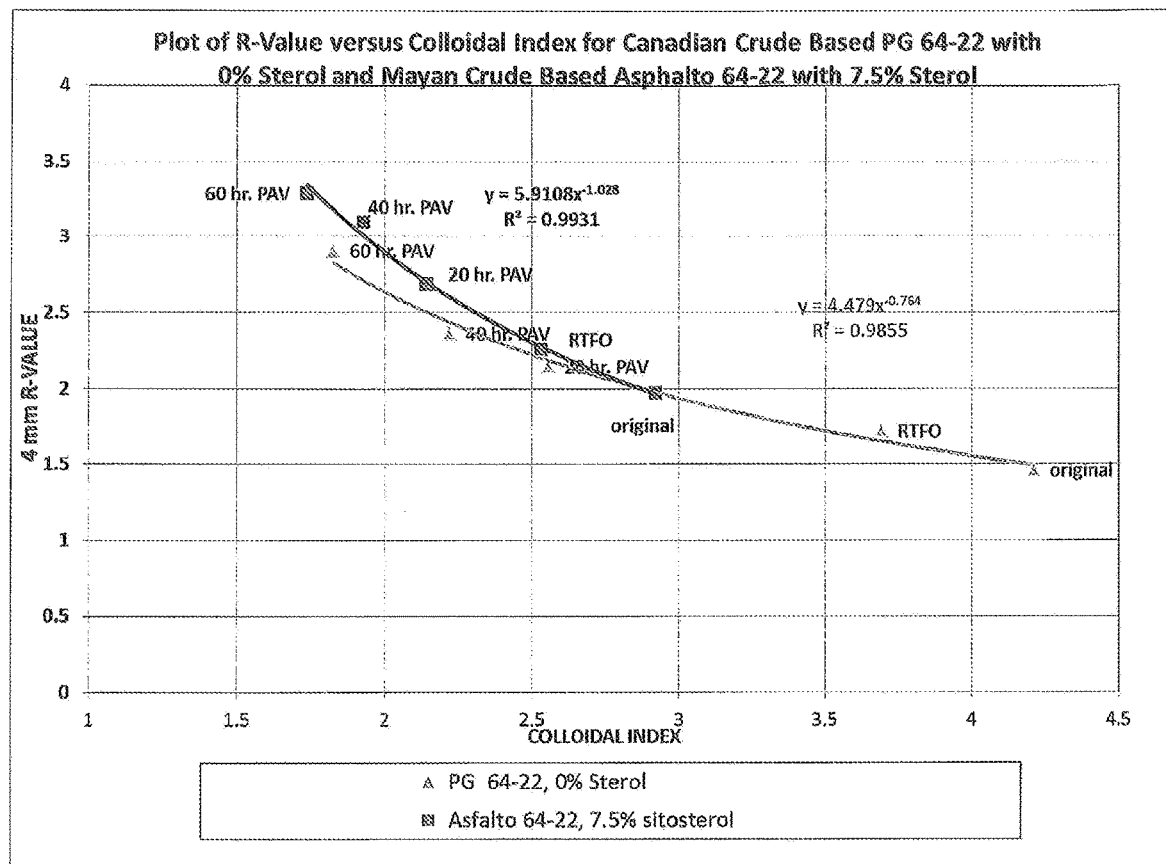
FIG. 8 is a graphical representation of a comparison of R-Value versus Colloidal Index for Canadian crude based PG 64-22 with 0% sterol and Mayan crude based Asphalto 64-22 with 7.5% sterol and both binders aged through 60 hours in the PAV.

FIG. 7 is a plot of R-Value versus Colloidal Index for the Canadian Crude based PG 64-22. The 0% sterol blend showed higher R-Values compared to the 5% and 7.5% blends. However the difference between the sterol blends and the control 0% blend is about half the difference for the Asphalto 64-22. FIG. 8 showed that through a comparison of R-value versus Colloidal Index for the Asphalto 64-22 with 7.5% sterol and the PG 64-22 with no additive that it is possible to move an asphalt binder with severe aging issues closer to the characteristics of an asphalt binder with minimal aging issues.

EXAMPLE 6

Example 4 showed that bio derived oils function as softening additives but their stiffness reducing impact was not sustained when combined with RAS in mixtures or when blended with asphalt recovered from shingles. The current example investigates whether the softening properties of a bio derived oil in conjunction with plant sterol combined with recovered asphalt from shingles followed by extended aging will continue to exhibit the softening properties of the bio derived oil or whether those properties will be degraded as has been seen with non plant sterol containing binders.

A blend of 20% shingle binder was added to the PG 52-34 binder used in previous examples. To this blend 5% mixed plant sterol and 2.5% of a bio derived oil were added. The blends were aged for up to 40 hours in the PAV and the R-Value, low temperature stiffness grade, m-value grade and ΔTc were determined as described previously. The mixed sterol used is as described in Example 1.

Table 13 shows the addition of 2.5% bio-derived oil to the PG 52-34 plus 5% sterol plus 20% shingle binder from RAS can the low temperature properties of the aged binder to nearly the same condition as the PG 52-34 binder plus 5% sterol sample without any shingle binder added. The presence of the shingle binder in the blend resulted in more negative ΔTc values after 20 and 40 hours of aging, but the ΔTc values were still acceptable and not close to the generally accepted point of potential performance damage of a ΔTc=−5.0° C. The low temperature grade of both binders after 20 hours of PAV aging was still a −34 grade and after 40 hours of PAV aging is approximately −33.5° for both blends.

TABLE 13

| Sample | Aging | R-Value | Stiffness Critical Grade | m-value Critical Grade | ΔTc |
|---|---|---|---|---|---|
| MIA 52-34, 20% RAS AC, 2.5% Cargill 1103, 5% Plant Sterols | unaged | 1.674 | −40.3 | −42.4 | 2.0 |
| MIA 52-34, 20% RAS AC, 2.5% Cargill 1103, 5% Plant Sterols | RTFO | 1.932 | −38.1 | −39.4 | 1.3 |
| MIA 52-34, 20% RAS AC, 2.5% Cargill 1103, 5% Plant Sterols | 20 hr. PAV | 2.308 | −37.0 | −35.9 | −1.1 |
| MIA 52-34, 20% RAS AC, 2.5% Cargill 1103, 5% Plant Sterols | 40 hr. PAV | 2.619 | −35.16 | −33.43 | −1.7 |
| 52-34 + 5% Sterols | unaged | 1.315 | −38.50 | −40.71 | 2.2 |
| 52-34 + 5% Sterols | RTFO | 1.604 | −36.44 | −37.93 | 1.5 |
| 52-34 + 5% Sterols | 20 hr. PAV | 1.905 | −34.37 | −34.80 | 0.4 |
| 52-34 + 5% Sterols | 40 hr. PAV | 2.109 | −33.08 | −33.62 | 0.5 |

EXAMPLE 7

To investigate whether crude sterol sources could produce the same results as shown above for pure sterols various blends shown below, were produced and aged by RFTO aged conditions and for 20 and 40 hours in the PAV (Pressured aging vessel) following ASTM D65217. The tall oil pitch was obtained from Union Camp under the trade name Tallex.
1. PG 64-22 plus 5% tall oil pitch
2. PG 64-22 plus 10% tall oil pitch
3. PG 64-22, 5% tall oil pitch, 8% REOB
4. PG 64-22, 10% tall oil pitch, 8% REOB Blends were produced by mixing the components with a low shear Lightning mixer in a 1 gallon can at a temperature of 187.8° C.-204° C. (370-400° F.) for approximately 30 minutes.

Initial testing at high temperatures was conducted to determine the high temperature PG grade of the blends and 4 mm DSR testing was conducted at all four aging conditions to determine the Stiffness Critical and m-value Critical low temperature PG grade of the blends at all four aging conditions. ΔTc, which is obtained by subtracting the m-value Critical low temperature value from the Stiffness Critical low temperature value was determined at all four aging conditions.

TABLE 14

| Binder Aging | % REOB | % Tall Oil Pitch | % Sterol | S_critical Temp | m_critical Temp | ΔTc | Low Temp PG Grade[1] | High temp DSR[2] |
|---|---|---|---|---|---|---|---|---|
| unaged | 0 | 0 | 0 | −30.51 | −32.72 | 2.21 | −30.51 | 66.80 |
| unaged | 0 | 0 | 5 | −29.53 | −31.82 | 2.29 | −29.53 | 64.90 |
| unaged | 0 | 5 | 0 | −31.81 | −34.88 | 3.07 | −31.81 | 64.2 |
| unaged | 0 | 10 | 0 | −32.75 | −34.81 | 2.06 | −32.75 | 61.50 |
| unaged | 8 | 5 | 0 | −37.62 | −38.90 | 1.28 | −37.62 | 59.7 |
| unaged | 8 | 10 | 0 | −37.79 | −39.53 | 1.74 | −37.79 | 56.50 |
| unaged | 8 | 0 | 0 | −36.1 | −38.2 | 2.10 | −36.10 | 63.2 |
| unaged | 8 | 0 | 2.5 | −35.9 | −37.8 | 1.83 | −35.93 | 62.5 |
| unaged | 8 | 0 | 5 | −34.8 | −38.6 | 3.80 | −34.80 | 61.2 |
| unaged | 8 | 0 | 7.5 | −35.4 | −38.3 | 2.90 | −35.40 | 58.9 |
| RTFO | 0 | 0 | 0 | −27.07 | −28.07 | 1.00 | −27.07 | |
| RTFO | 0 | 0 | 5 | −27.05 | −28.86 | 1.81 | −27.05 | |
| RTFO | 0 | 5 | 0 | −29.082 | −32.3 | 3.19 | −29.08 | |
| RTFO | 0 | 10 | 0 | −29.91 | −34.12 | 4.20 | −29.91 | |
| RTFO | 8 | 5 | 0 | −34.45 | −35.55 | 1.10 | −34.45 | |
| RTFO | 8 | 10 | 0 | −35.98 | −36.46 | 0.48 | −35.98 | |
| RTFO | 8 | 0 | 0 | −35.0 | −35.6 | 0.60 | −35.00 | |
| RTFO | 8 | 0 | 2.5 | −35.2 | −35.4 | 0.17 | −35.21 | |
| RTFO | 8 | 0 | 5 | −34.3 | −36.8 | 2.50 | −34.30 | |
| RTFO | 8 | 0 | 7.5 | −34.1 | −35.8 | 1.75 | −34.09 | |
| 20 hr. PAV | 0 | 0 | 0 | −24.91 | −23.99 | −0.92 | −23.99 | |
| 20 hr. PAV | 0 | 0 | 5 | −24.81 | −25.29 | 0.48 | −24.81 | |
| 20 hr. PAV | 0 | 5 | 0 | −25.346 | −25.5 | 0.16 | −25.35 | |
| 20 hr. PAV | 0 | 10 | 0 | −26.48 | −25.90 | −0.58 | −25.90 | |
| 20 hr. PAV | 8 | 5 | 0 | −31.48 | −28.97 | −2.51 | −28.97 | |

TABLE 14-continued

| Binder Aging | % REOB | % Tall Oil Pitch | % Sterol | S_critical Temp | m_critical Temp | ΔTc | Low Temp PG Grade[1] | High temp DSR[2] |
|---|---|---|---|---|---|---|---|---|
| 20 hr. PAV | 8 | 10 | 0 | −33.11 | −30.62 | −2.49 | −30.62 | |
| 20 hr. PAV | 8 | 0 | 0 | −34.6 | −30.9 | −3.64 | −30.92 | |
| 20 hr. PAV | 8 | 0 | 2.5 | −32.3 | −29.4 | −2.84 | −29.43 | |
| 20 hr. PAV | 8 | 0 | 5 | −29.7 | −28.4 | −1.27 | −28.42 | |
| 20 hr. PAV | 8 | 0 | 7.5 | −31.4 | −29.5 | −1.87 | −29.52 | |
| 40 hr. PAV | 0 | 0 | 0 | −23.66 | −22.24 | −1.42 | −22.24 | |
| 40 hr. PAV | 0 | 0 | 5 | −23.54 | −23.38 | −0.15 | −23.38 | |
| 40 hr. PAV | 0 | 5 | 0 | −23.952 | −22.0 | −2.00 | −21.96 | |
| 40 hr. PAV | 0 | 10 | 0 | −25.76 | −23.25 | −2.51 | −23.25 | |
| 40 hr. PAV | 8 | 5 | 0 | −29.86 | −24.39 | −5.47 | −24.39 | |
| 40 hr. PAV | 8 | 10 | 0 | −30.79 | −26.38 | −4.41 | −26.38 | |
| 40 hr. PAV | 8 | 0 | 0 | −30.9 | −24.5 | −6.46 | −24.48 | |
| 40 hr. PAV | 8 | 0 | 2.5 | −31.1 | −25.9 | −5.20 | −25.88 | |
| 40 hr. PAV | 8 | 0 | 5 | −29.6 | −26.6 | −2.93 | −26.62 | |
| 40 hr. PAV | 8 | 0 | 7.5 | −30.4 | −28.4 | −2.05 | −28.38 | |

[1]The low temperature PG grade is determined as the warmest temperature between the S Critical Temperature and the m-value Critical Temperature. Examination of this table shows that as the binders age the m-value critical temperature increases at a more rapid rate than the S Critical temperature. As a result the value of ΔTc decreases with aging becoming less positive and eventually after the 20 hour PAV aging period becomes negative.
[2]The high temperature PG grade is determined as the lowest temperature value at which the unaged binder achieves a stiffness of 1 kiloPascal or the RTFO aged sample achieves a stiffness of 2.2 kiloPascals. Data is only shown for the unaged samples because for all the samples in question the temperature at which the 1 kiloPascal stiffness was achieved was lower than the temperature at which the 2.2 kiloPascal stiffness was achieved.

Figure 9:
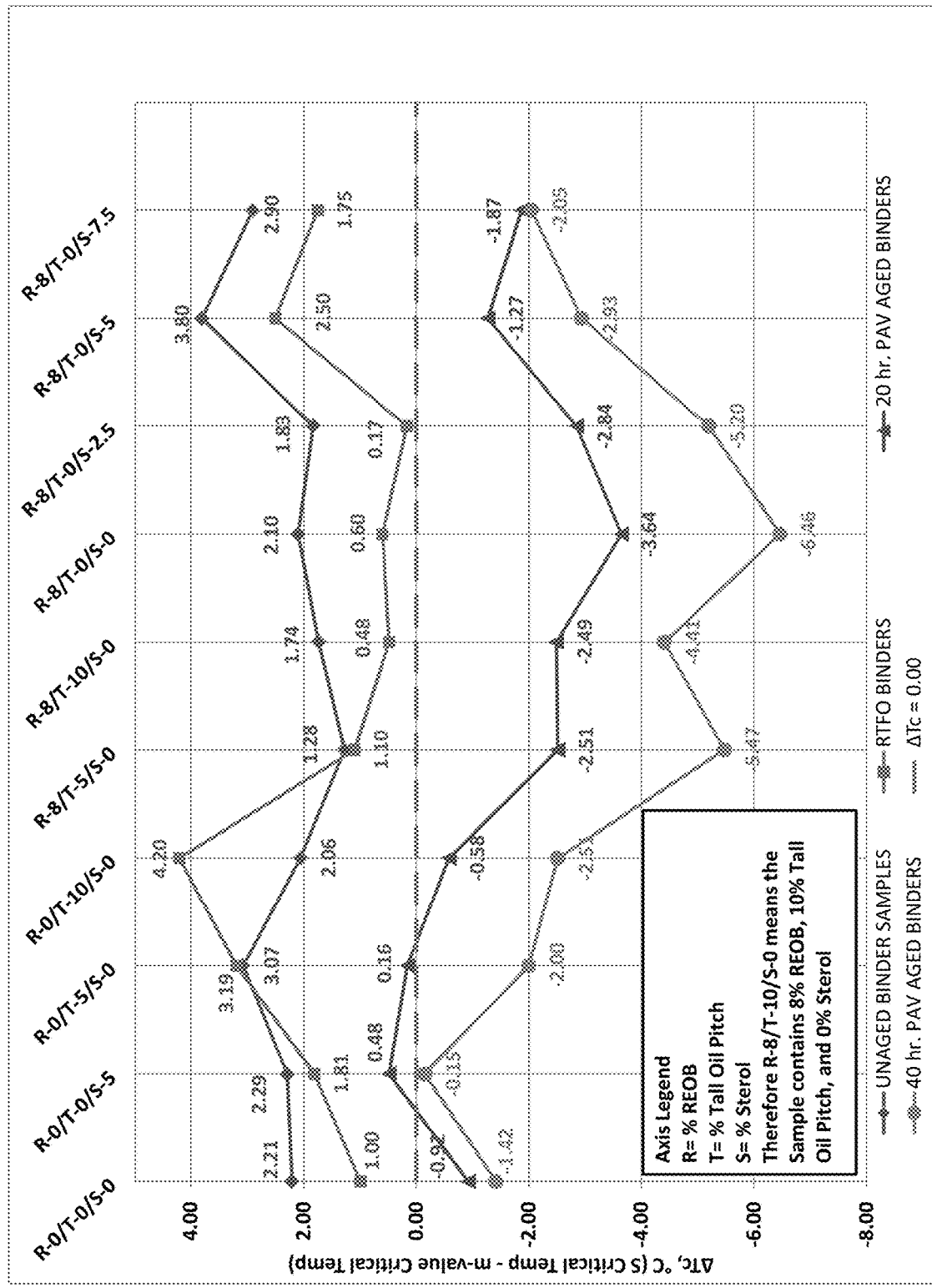
FIG. 9 is a graphical representation of high temperature binder grade and ΔTc for various blends of tall oil pitch, sterols and REOB in PG 64-22 and aged under various aging conditions.

The data from Table 14 is plotted and shown in FIG. 9. Compared to the control PG 64-22 all blends have reduced high temperature stiffness values, if only by minor amounts in some instances.

The blends with tall oil pitch (5% (R-0/T-5/S-0) and 10% (R-0/T-10/S-0) exhibit decreasing high temperature stiffness values as would be expected with the addition of a softening additive. The blends with tall oil pitch plus REOB show further decreases in high temperature stiffness, also expected because of the stiffness reducing properties of the REOB. The sterol blends with REOB also show decreasing high temperature stiffness grades as the sterol content increases with the addition of 8% REOB.

There is a linear decrease in the high temperature binder stiffness grade as the binder blend changes from no additives (R-0/T-0/S-0) to the blend with the greatest amount of additives (R-8/T-10/S-0). This implies that only the softening effect of the REOB and tall oil pitch are responsible for the reduction in the high temperature stiffness grade. The data shown in Table 15 for blends with just 8% REOB and 0, 5 and 10% tall oil pitch have an $R^2$ value of 0.99 for the prediction of high temperature stiffness grade as a linear function of percent tall oil pitch as described in FIG. 10.

There is a second order decrease in the high temperature binder stiffness grade as the binder blend changes from no additives (R-0/T-0/S-0) to blends with 8% REOB and no sterol (R-8/T-0/S-0) to the blends with 8% REOB and increasing levels of sterol (2.5%, 5%, 7.5%). The R2 for the second order relationship is also 0.99. Data plots for the information presented in Tables 15 and 16 are shown in FIG. 10.

Figure 10:
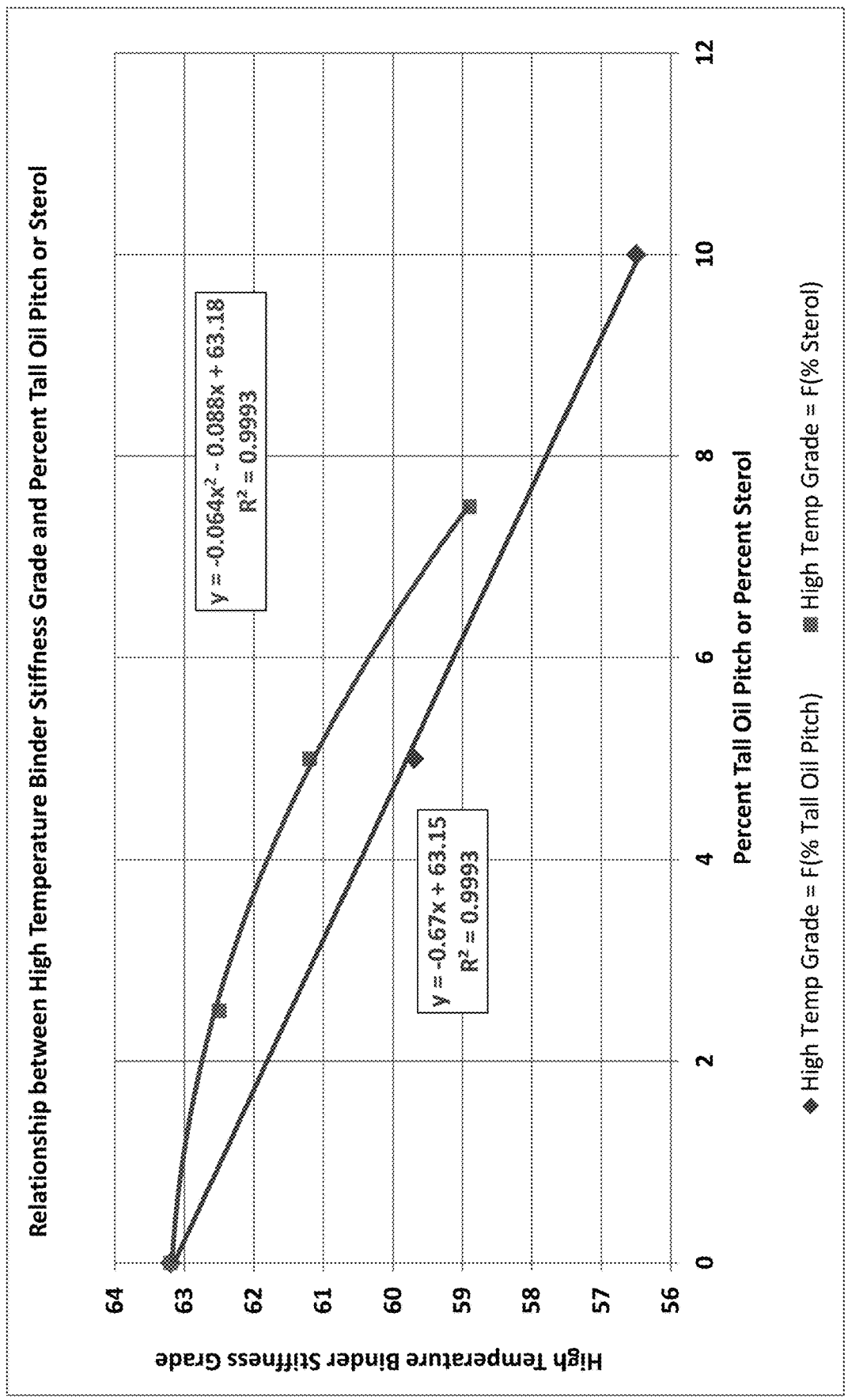
FIG. 10 is a graphical representation comparing the relationship of high temperature binder stiffness grade as a function of percent tall oil pitch and the relationship of high temperature stiffness grade as a function of percent sterol.

The data shown in FIG. 10 implies that for equivalent amounts of either tall oil pitch or sterol with 8% REOB the high temperature stiffness grade of the binder decreases at a slower rate when sterol is employed versus when tall oil pitch is employed. The second order functional nature of the pure sterol blends also suggests an interaction between the sterol and the REOB in the PG 64-22.

TABLE 15

| % Tall Oil Pitch | High Temperature Stiffness Grade | Increase in low PG grade between 20 & 40 hour PAV |
|---|---|---|
| 0 | 63.2 | 6.46 |
| 5 | 59.7 | 4.58 |
| 10 | 56.5 | 4.24 |

TABLE 16

| % Sterol | High Temperature Stiffness Grade | Increase in low PG grade between 20 & 40 hour PAV |
|---|---|---|
| 0 | 63.2 | 6.44 |
| 2.5 | 62.5 | 3.55 |
| 5 | 61.2 | 1.8 |
| 7.5 | 58.9 | 1.14 |

Figure 11:
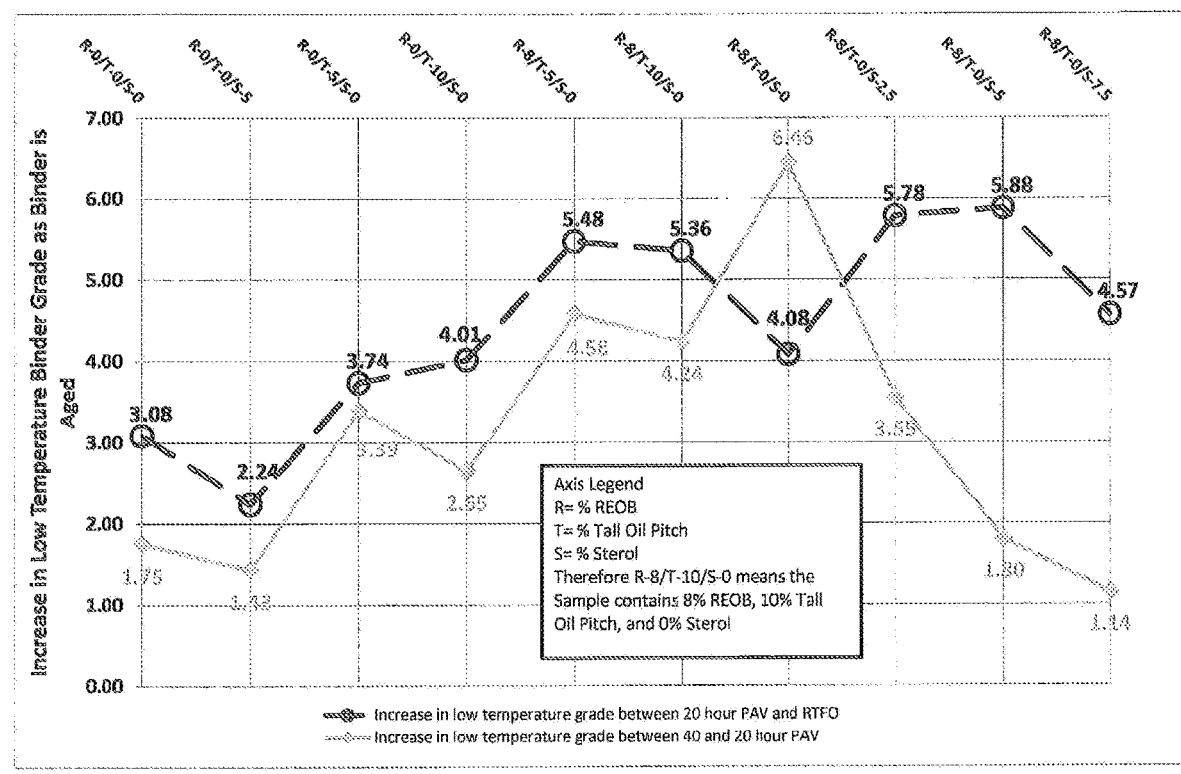
FIG. 11 is a graphical representation showing increase in binder low temperature PG grade when binder is aged in a RTFO to 20 hours of PAV aging and when the binder is aged from 20 hours of PAV aging to 40 hours of PAV aging.
Figure 12:
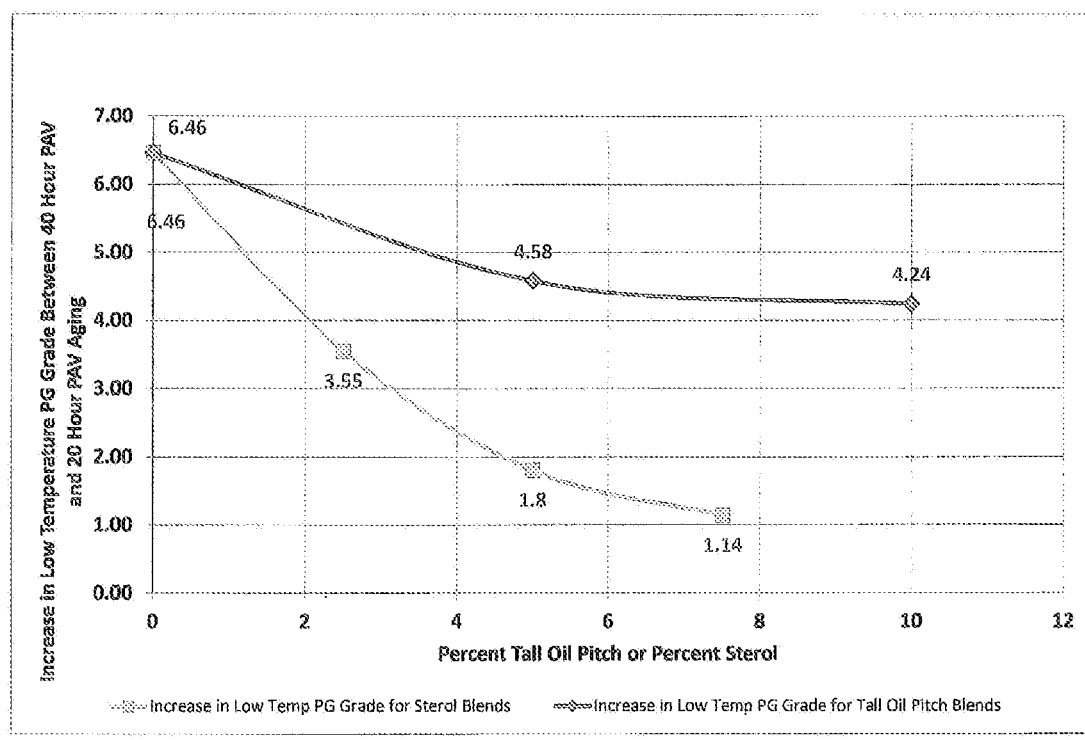
FIG. 12 is a graphical representation showing the relative rate of increase in low temperature PG grade between the 20 hours of PAV aging and 40 hours of PAV aging for sterol and tall oil pitch.

These similarities in high temperature stiffness reflect the unaged condition. The long range performance properties of these blends are obtained from examination of the low temperature properties after aging has occurred. Further examination of FIG. 9 shows the following results for the low temperature ΔTc properties of the binders as they are aged. After RTFO aging plus 20 and 40 hours of PAV aging the 5% and 10% tall oil pitch blends with 8% REOB showed ΔTc properties similar to the 2.5% sterol blend with 8% REOB. The 40 hour PAV residue of the 5% sterol blend with 8% REOB had ΔTc properties similar to the 20 hour properties of the previously described samples. FIG. 11 plots the increase in the low temperature PG grades of the binder blends at the 20 hour PAV condition compared to the RTFO aged condition and at the 40 hour PAV aged condition compared to the 20 hour PAV aged condition. The trends in FIG. 11 show that for blends containing tall oil pitch the increase in low temperature PG grade is less as the binder aged from 20 to 40 hours in the PAV compared to the RTFO to 20 hour PAV aged condition. This is the case whether REOB is present or not. The sample with only REOB shows more than a 50% increase in the low temperature PG grade aging from 20 to 40 hours in the PAV while the 40 hour PAV low temperature grade increase 5% and 10% tall oil pitch blends with REOB maintain the low temperature grade increase of the 20 hour PAV residue of the blend containing only REOB. The most interesting trend of all is that the 20 hour to 40 hour change in the low temperature PG grade for the 2.5%, 5% and 7.5% sterol blends with REOB show a decreasing level of low temperature grade change as the sterol level increases. This is another indication of the age retarding power of the sterol additive. This impact of sterol containing materials is significant because research has shown that long range performance is better correlated to the low temperature binder properties after 40 hours of PAV aging compared to 20 hour PAV aging.

EXAMPLE 8

To investigate whether enriching the tall oil pitch with additional sterol could produce results comparable to using the pure sterol alone, blends of pure sterol in tall oil pitch were produced as shown below and aged by RFTO aged conditions and for 20 and 40 hours in the PAV (Pressured aging vessel) following ASTM D65217. The tall oil pitch was obtained from Union Camp. A PG 64-22 base asphalt plus 8% REOB was chosen to produce the various blends. Based on the literature for tall oil pitch, 15% is a reasonable amount for the sterol content in the tall oil pitch. Sufficient pure sterol was added to the tall oil pitch such that a 10% addition of the tall oil pitch plus pure sterol blend would approximate 2.5%, 5% or 7.5% pure sterol. It was determined that10% of a 85% tall oil pitch plus 15% pure sterol blend would approximate a sterol loading in the asphalt equivalent to 2.5% pure sterol. Similarly a blend 10% of a 60% tall oil pitch and 40% pure sterol would approximate a 5% pure sterol loading and a blend of 10% of a 30% tall oil pitch and 70% pure sterol would approximate a 7.5% pure sterol loading. Table 17 shows the information for the blends, the aging condition, the low temperature stiffness critical temperatures, the low temperature m-critical temperatures, the ΔTc values, the low temperature PG grade and the high temperature PG grade. The 60 hour PAV aging was not performed on the PG 64-22 with 8% REOB only.

Blends were produced by mixing the components with a low shear Lightning mixer in a 1 gallon can at a temperature of 187.8° C.-204° C. (370-400° F.) for approximately 30 minutes.

Initial testing at high temperatures was conducted to determine the high temperature PG grade of the blends and 4 mm DSR testing was conducted at all four aging conditions to determine the Stiffness Critical and m-value Critical low temperature PG grade of the blends at all four aging conditions. ΔTc, which is obtained by subtracting the m-value Critical low temperature value from the Stiffness Critical low temperature value was determined at all four aging conditions. A comparison of the 40 hour PAV ΔTc results for the 2.5%, 5% and 7.5% pure sterol blends shown in Table 14 with the results for the 10% blends of 85/15, 60/40, and 30/70 shown in Table 17 provides the following data. The 2.5% pure sterol blend has a ΔTc value of −5.20° C. and the 10% blend of 85/15 tall oil pitch/pure sterol has a ΔTc value of −4.66° C.; 5% pure sterol has a ΔTc of −2.93° C. and 10% of the 60/40 blend a ΔTc of −3.57° C. and 7.5% pure sterol has a ΔTc of −2.05° C. and 10% of the 30/70 blend a ΔTc of −2.05° C. These results suggest that sterol level in tall oil pitch plus pure sterol blends employed is comparable to using pure sterol at the dosages indicated. Therefore by using 10% or less of such a sterol concentrated tall oil pitch can result in comparable results.

TABLE 17

| Binder Aging | % REOB added to binder | % Tall oil Pitch and Sterol blend added to binder | Ratio of tall oil pitch to Sterol TOP/Sterol | S-Critical Temp | m-Critical temp | ΔTc | Low temp PG Grade | High Temp PG Grade |
|---|---|---|---|---|---|---|---|---|
| Unaged | 8 | 0 | 0/0 | −36.1 | −38.2 | 2.10 | −36.1 | 63.2 |
| Unaged | 8 | 10 | 85/15 | −38.20 | −39.26 | 1.06 | −38.2 | 56.4 |
| Unaged | 8 | 10 | 60/40 | −36.29 | −38.27 | 1.98 | −36.29 | 56.9 |
| Unaged | 8 | 10 | 30/70 | −34.20 | −37.51 | 3.30 | −34.20 | 57.0 |
| RTFO | 8 | 0 | 0/0 | −35 | −35.60 | 0.60 | −35.0 | 64.0 |
| RTFO | 8 | 10 | 85/15 | −35.666 | −36.394 | 0.73 | −35.67 | 57.1 |
| RTFO | 8 | 10 | 60/40 | −34.90 | −35.92 | 1.03 | −34.90 | 57.1 |
| RTFO | 8 | 10 | 30/70 | −33.05 | −35.55 | 2.49 | −33.05 | 57.3 |

TABLE 17-continued

| Binder Aging | % REOB added to binder | % Tall oil Pitch and Sterol blend added to binder | Ratio of tall oil pitch to Sterol TOP/Sterol | S-Critical Temp | m-Critical temp | ΔTc | Low temp PG Grade | High Temp PG Grade |
|---|---|---|---|---|---|---|---|---|
| 20 hr. PAV | 8 | 0 | 0/0 | −34.56 | −30.92 | −3.64 | −30.92 | 82.5 |
| 20 hr. PAV | 8 | 10 | 85/15 | −33.045 | −31.231 | −1.81 | −31.23 | 75.1 |
| 20 hr. PAV | 8 | 10 | 60/40 | −32.32 | −30.46 | −1.86 | −30.46 | 75.2 |
| 20 hr. PAV | 8 | 10 | 30/70 | −30.52 | −29.65 | −0.87 | −29.65 | 74.3 |
| 40 hr. PAV | 8 | 0 | 0/0 | −30.94 | −24.48 | −6.46 | −24.48 | 95.1 |
| 40 hr. PAV | 8 | 10 | 85/15 | −32.345 | −27.681 | −4.66 | −27.681 | 83.2 |
| 40 hr. PAV | 8 | 10 | 60/40 | −30.75 | −27.18 | −3.57 | −27.18 | 81.8 |
| 40 hr. PAV | 8 | 10 | 30/70 | −28.40 | −26.36 | −2.05 | −26.36 | 80.4 |
| 60 hr. PAV | 8 | 10 | 85/15 | −30.42 | −22.98 | −7.44 | −22.98 | 89.9 |
| 60 hr. PAV | 8 | 10 | 60/40 | −30.48 | −25.40 | −5.08 | −25.40 | 87.4 |
| 60 hr. PAV | 8 | 10 | 30/70 | −28.52 | −25.60 | −2.91 | −25.60 | 84.1 |

EXAMPLE 9

To evaluate whether Cashew Nut Shell Liquid (CNSL) and cholesterol can retard the aging on asphalt binders, the blends noted below were mixed as in Example 2:

PG 64-22, 8% REOB, and 5% Cashew Nut Shell Liquid (CNSL) marketed as Rheofalt HP-EM obtained from Van Weezenbeek Specialties in the Netherlands. CNSL is said to contain approximately 10% plant sterols and is promoted as an asphalt rejuvenator.

PG 64-22, 8% REOB and 5% lab grade cholesterol purchased from VWR scientific and supplied by Amresco, LLC of Solon, OH.

The pure plant sterols used are the same as those described in Example 1.

Using PG 64-22, blends were produced using 0%, 2.5%, 5% and 7.5% sterol, 5% CNSL, or 5% cholesterol with 8% REOB and tested for their low temperature stiffness and m-value critical temperatures in the unaged, RTFO aged, 20 hour PAV aged, 40 hour PAV and 60 hour PAV conditions using the 4 mm DSR test procedure. Low temperature properties and ΔTc values were measured using the 4 mm DSR test procedure.

Figure 13:
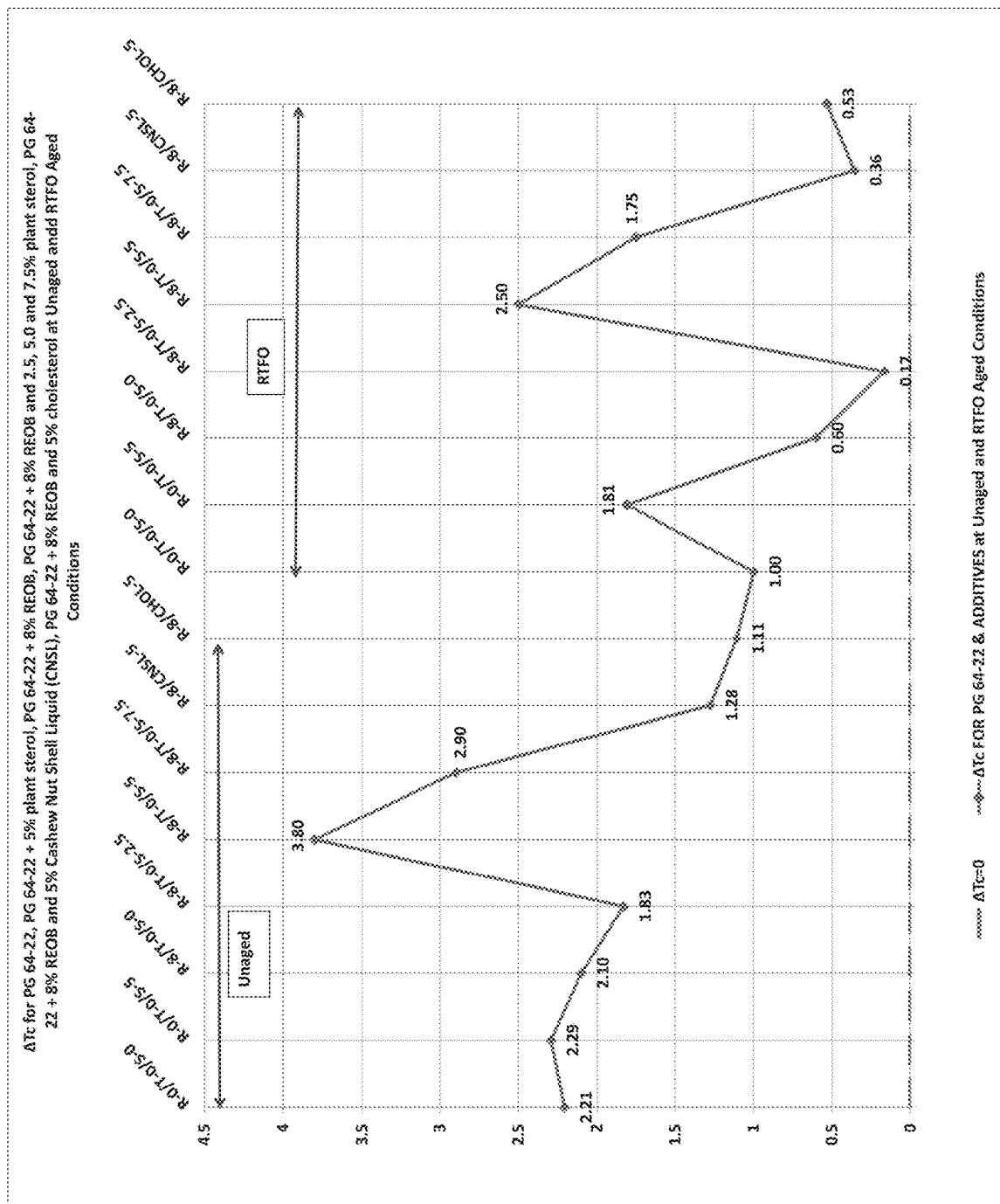
FIG. 13 is a graphical representation for PG 64-22 with no additive (base case control), 5% plant sterol only (positive control), 8% REOB only (negative control) and samples containing 8% REOB plus 2.5, 5% or 7.5% plant sterol; 5% cholesterol; or 5% cashew nut shell liquid (CNSL) and showing ΔTc for the unaged and RFTO aging of samples.
Figure 14:
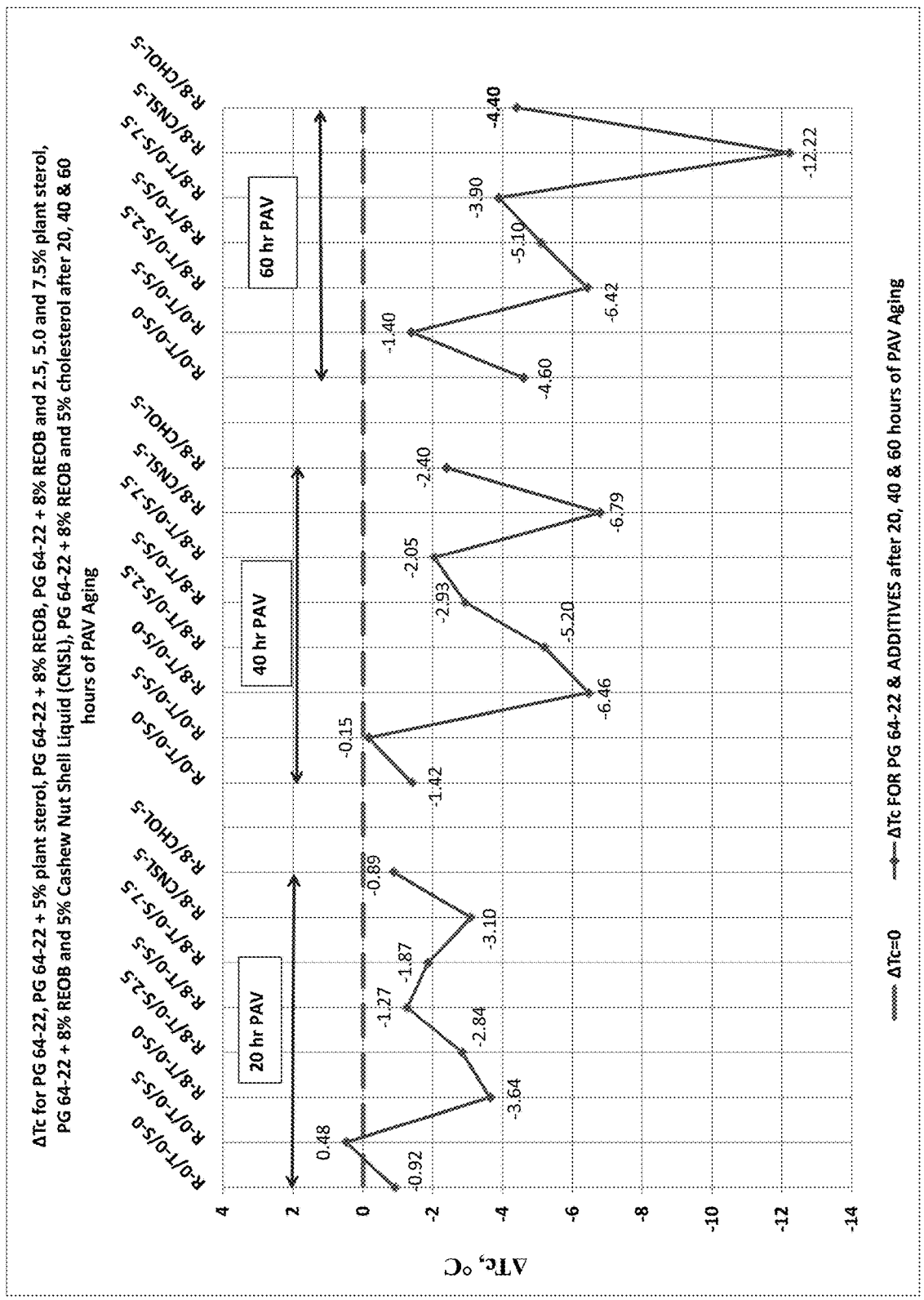
FIG. 14 is a graphical representation for samples of PG 64-22 with no additive (base case control), 5% plant sterol only (positive control), 8% REOB only (negative control) and samples containing 8% REOB plus 2.5, 5% or 7.5% plant sterol; 5% cholesterol; or 5% cashew nut shell liquid (CNSL) and showing ΔTc for the 20, 40 and 60 hours of PAV aging of samples.

The data is shown in Table 18 and plotted in FIGS. 13 and 14.

TABLE 18

| Binder Aging | % REOB | % Tall Oil Pitch | % Sterol | % CNSL | % Cholesterol | S_critical Temp | m_critical Temp | ΔTc | R-Value |
|---|---|---|---|---|---|---|---|---|---|
| unaged | 0 | 0 | 0 | 0 | 0 | −30.51 | −32.72 | 2.21 | 1.46 |
| unaged | 0 | 0 | 5 | 0 | 0 | −29.53 | −31.82 | 2.29 | 1.31 |
| unaged | 0 | 5 | 0 | 0 | 0 | −31.81 | −34.88 | 3.07 | 1.448 |
| unaged | 0 | 10 | 0 | 0 | 0 | −32.75 | −34.81 | 2.06 | 1.376 |
| unaged | 8 | 5 | 0 | 0 | 0 | −37.62 | −38.90 | 1.28 | 1.6 |
| unaged | 8 | 10 | 0 | 0 | 0 | −37.79 | −39.53 | 1.74 | 1.535 |
| unaged | 8 | 0 | 0 | 0 | 0 | −36.10 | −38.20 | 2.10 | 1.759 |
| unaged | 8 | 0 | 2.5 | 0 | 0 | −35.93 | −37.76 | 1.83 | 1.627 |
| unaged | 8 | 0 | 5 | 0 | 0 | −34.80 | −38.60 | 3.80 | 1.59 |
| unaged | 8 | 0 | 7.5 | 0 | 0 | −35.40 | −38.30 | 2.90 | 1.496 |
| unaged | 8 | 0 | 0 | 5 | 0 | −38.69 | −39.97 | 1.28 | 1.54 |
| unaged | 8 | 0 | 0 | 0 | 5 | −35.23 | −36.34 | 1.11 | 1.47 |
| RTFO | 0 | 0 | 0 | 0 | 0 | −27.07 | −28.07 | 1.00 | 1.721 |
| RTFO | 0 | 0 | 5 | 0 | 0 | −27.05 | −28.86 | 1.81 | 1.486 |
| RTFO | 0 | 5 | 0 | 0 | 0 | −29.08 | −32.27 | 3.19 | 1.666 |
| RTFO | 0 | 10 | 0 | 0 | 0 | −29.91 | −34.12 | 4.20 | 1.618 |
| RTFO | 8 | 5 | 0 | 0 | 0 | −34.45 | −35.55 | 1.10 | 1.824 |
| RTFO | 8 | 10 | 0 | 0 | 0 | −35.98 | −36.46 | 0.48 | 1.777 |
| RTFO | 8 | 0 | 0 | 0 | 0 | −35.00 | −35.60 | 0.60 | 2.04 |
| RTFO | 8 | 0 | 2.5 | 0 | 0 | −35.21 | −35.38 | 0.17 | 1.955 |
| RTFO | 8 | 0 | 5 | 0 | 0 | −34.30 | −36.80 | 2.50 | 1.788 |
| RTFO | 8 | 0 | 7.5 | 0 | 0 | −34.09 | −35.84 | 1.75 | 1.836 |
| RTFO | 8 | 0 | 0 | 5 | 0 | −36.61 | −36.97 | 0.36 | 1.79 |
| RTFO | 8 | 0 | 0 | 0 | 5 | −33.02 | −33.55 | 0.53 | 1.68 |

TABLE 18-continued

| Binder Aging | % REOB | % Tall Oil Pitch | % Sterol | % CNSL | % Cholesterol | S_critical Temp | m_critical Temp | ΔTc | R-Value |
|---|---|---|---|---|---|---|---|---|---|
| 20 hr. PAV | 0 | 0 | 0 | 0 | 0 | −24.91 | −23.99 | −0.92 | 2.15 |
| 20 hr. PAV | 0 | 0 | 5 | 0 | 0 | −24.81 | −25.29 | 0.48 | 1.90 |
| 20 hr. PAV | 0 | 5 | 0 | 0 | 0 | −25.35 | −25.50 | 0.16 | 2.096 |
| 20 hr. PAV | 0 | 10 | 0 | 0 | 0 | −26.48 | −25.90 | −0.58 | 2.069 |
| 20 hr. PAV | 8 | 5 | 0 | 0 | 0 | −31.48 | −28.97 | −2.51 | 2.434 |
| 20 hr. PAV | 8 | 10 | 0 | 0 | 0 | −33.11 | −30.62 | −2.49 | 2.331 |
| 20 hr. PAV | 8 | 0 | 0 | 0 | 0 | −34.56 | −30.92 | −3.64 | 2.49 |
| 20 hr. PAV | 8 | 0 | 2.5 | 0 | 0 | −32.27 | −29.43 | −2.84 | 2.311 |
| 20 hr. PAV | 8 | 0 | 5 | 0 | 0 | −29.69 | −28.42 | −1.27 | 2.371 |
| 20 hr. PAV | 8 | 0 | 7.5 | 0 | 0 | −31.39 | −29.52 | −1.87 | 2.078 |
| 20 hr. PAV | 8 | 0 | 0 | 5 | 0 | −32.05 | −28.95 | −3.10 | 2.49 |
| 20 hr. PAV | 8 | 0 | 0 | 0 | 5 | −29.74 | −28.85 | −0.89 | 2.07 |
| 40 hr. PAV | 0 | 0 | 0 | 0 | 0 | −23.66 | −22.24 | −1.42 | 2.36 |
| 40 hr. PAV | 0 | 0 | 5 | 0 | 0 | −23.54 | −23.38 | −0.15 | 2.20 |
| 40 hr. PAV | 0 | 5 | 0 | 0 | 0 | −23.95 | −21.96 | −2.00 | 2.422 |
| 40 hr. PAV | 0 | 10 | 0 | 0 | 0 | −25.76 | −23.25 | −2.51 | 2.358 |
| 40 hr. PAV | 8 | 5 | 0 | 0 | 0 | −29.86 | −24.39 | −5.47 | 2.822 |
| 40 hr. PAV | 8 | 10 | 0 | 0 | 0 | −30.79 | −26.38 | −4.41 | 2.694 |
| 40 hr. PAV | 8 | 0 | 0 | 0 | 0 | −30.94 | −24.48 | −6.46 | 3.03 |
| 40 hr. PAV | 8 | 0 | 2.5 | 0 | 0 | −31.08 | −25.88 | −5.20 | 2.537 |
| 40 hr. PAV | 8 | 0 | 5 | 0 | 0 | −29.55 | −26.62 | −2.93 | 2.440 |
| 40 hr. PAV | 8 | 0 | 7.5 | 0 | 0 | −30.42 | −28.38 | −2.05 | 2.360 |
| 40 hr. PAV | 8 | 0 | 0 | 5 | 0 | −30.12 | −23.33 | −6.79 | 3.240 |
| 40 hr. PAV | 8 | 0 | 0 | 0 | 5 | −29.17 | −26.77 | −2.40 | 2.330 |
| 60 hr. PAV | 0 | 0 | 0 | 0 | 0 | −23.20 | −18.60 | −4.60 | 2.909 |
| 60 hr. PAV | 0 | 0 | 5 | 0 | 0 | −21.40 | −20.00 | −1.40 | 2.422 |
| 60 hr. PAV | 8 | 0 | 2.5 | 0 | 0 | −29.92 | −23.50 | −6.42 | 2.956 |
| 60 hr. PAV | 8 | 0 | 5 | 0 | 0 | −28.30 | −23.20 | −5.10 | 2.704 |
| 60 hr. PAV | 8 | 0 | 7.5 | 0 | 0 | −28.70 | −24.80 | −3.90 | 2.501 |
| 60 hr. PAV | 8 | 0 | 0 | 5 | 0 | −28.72 | −16.50 | −12.22 | 3.840 |
| 60 hr. PAV | 8 | 0 | 0 | 0 | 5 | −28.83 | −24.43 | −4.40 | 2.530 |

Table 18 summarizes data produced for PG 64-22 with no additive to serve as a baseline. PG 64-22 plus 8% REOB served as a negative control and PG 64-22+5% pure sterol served as a positive control. Other blends used PG 64-22+ 8% REOB plus additives that contained varying levels of pure sterol, 5% CNSL, and 5% cholesterol. When REOB is combined with different amounts of sterol there is a dose response effect wherein greater sterol amounts provide increased retardation of the effect of aging as quantified by the parameter ΔTc. It was found that as the dose sterol level decreased at any given aging period, the ΔTc parameter became more negative. Additionally as the binder aging time or process was increased for a given sterol dosage level, the ΔTc parameter became more negative. The more negative the value of ΔTc becomes, the greater the possibility that pavement distress will occur.

Table 18 also shows that through 40 hours of PAV aging, the 8% REOB+5% CNSL blend ΔTc is similar to that of the 8% REOB blend with no additive, 2.38° C. worse than the blend with 10% tall oil pitch+8% REOB, and 1.32° C. worse than the blend with 5% tall oil pitch+8% REOB. At the 20 hour PAV aging point the CNSL blend already has worse ΔTc values than either the 5% or 10% tall oil pitch blends with 8% REOB.

FIG. 13 shows the trend of ΔTc for the different samples being reported for just the unaged and the rolling thin film oven (RTFO) aged condition. As the data shows, when there is less severe aging the impact on ΔTc is negligible and the ΔTc value is greater than zero. It is possible to observe from the ΔTc data in FIG. 13 that testing binders containing REOB with no or minimal aging could lead to the conclusion that REOB is a material that would perform well in asphalt mixtures.

FIG. 14 shows the trend of ΔTc for the 20, 40 and 60 hour pressure aging vessel (PAV) aged samples. As these data show, the impact on ΔTc is substantial and more negative with more severe aging. The data also shows no REOB or no REOB plus 5% pure sterol results in very minor aging impact through 40 hours of PAV aging. The data shows that blends containing 8% REOB and no sterol or varying levels of pure sterol are benefited by greater amounts of the pure sterol additive. Even though the CNSL is reported to contain approximately 10% sterol there is little beneficial impact even at the 20 PAV aging condition. As aging continues to 40 and 60 hours, the CNSL blend matches the blend containing only 8% REOB. The blend containing 8% REOB and 5% CNSL was aged for 60 hours and the ΔTc value dropped from −6.42° C. to −12.22° C. or effectively a doubling of the negative impact of aging. Given the data trends at 20 and 40 hours of PAV aging between the 5% CNSL blend with 8% REOB and the 8% REOB only blend it is reasonable to assume the 8% REOB only blend would after 60 hours of PAV aging exhibit a ΔTc value near −12° C.

FIG. 14 also shows the blend of PG 64-22+8% REOB and 5% cholesterol at the 40 and 60 hour aging condition exhibited ΔTc results that lie between the 5% pure plant sterol and the 7.5% pure plant sterol data. A conclusion based on these data would be that the sterol chemical structure and not necessarily the source of the sterol material is the important driver in the age retarding impact of these materials.

FIGS. 15, 16 and 17 are Black Space plots for RTFO, 20 hour PAV and 60 hour PAV binders respectively. This progression of plots is intended to show the impact of increasing severity of binder aging on all blends and specifically focus on the benefits of cholesterol and showing the relatively poor performance of the CNSL blend compared to some of the plant sterol blends and the cholesterol blend (all with 8% REOB added to PG 64-22) as aging progresses from RTFO to 60 hours in the PAV. A Black Space plot can be informative with respect to the impact of aging on a binder. In all three figures a vertical line is shown at a phase angle of 45°. The 45° phase angle is important because at that phase angle the elastic and viscous moduli of bitumen are the same. Any given binder will have its maximum Black Space curve when unaged. The 45° phase angle is therefore a convenient reference point for comparing the relative impact of aging on a binder or the relative impact of comparing the impact of additives on a binder when the aging conditions for a series of binders is the same. Also shown on all three figures is a horizontal line at the log of binder stiffness of 1 MPa or a log value of 6. The phase angles of the different binder blends were compared at a consistent value of 1 MPa. The choice to compare phase angles at a constant complex modulus of 1 MPa (1E6 Pa) was because that stiffness value is approximately midway between the typical maximum stiffness modulus for bitumen of 100 MPa (1E9 Pa) also known as the glassy modulus and the lower stiffness modulus at the 25° C. reference temperature for most of the binders investigated of 1000 Pa (1E3 Pa). At the constant stiffness value of 1 MPa higher phase angles indicate less aged binder and the lower phase angles indicate more aged binder. A review of the overall data plots for FIGS. 15-17 shows that as the binder aging progresses from RTFO to 60 hour PAV all of the data plots move closer to the intersection point of the vertical phase angle line of 45° and the horizontal modulus line of 1 MPa.

RTFO binder data for the G* modulus at a constant phase angle of 45° and for the phase angle at a constant shear modulus of 1 MPa are shown in Table 19. The plot number values are in descending order from plot #1 at the top of FIG. 15 to plot #7 at the bottom of the data races. All samples shown in FIG. 15 are RTFO residues of PG 64-22 with 8% REOB (except for plot #1 which is intended to serve as a positive control and plot #3 which is the original base binder for all the blends). Additionally the other samples contained additives that are supposed to provide some rejuvenating benefits. It stands to reason that plot #1 would have the highest Black Space plot because it contained no REOB and also contained 5% plant sterol. Plot #2 contained 5% cholesterol and has a higher modulus at 45° and greater phase angle at 1 MPa than the sample #3 with no REOB. Plot #4 with 5% mix plant sterol lies nearly on the same trace as the sample with no REOB. These two samples, the 5% cholesterol and 5% plant sterol show in Black Space the benefit they bring to retard binder aging. Plot #6 contains 5% tall oil pitch, plot #5 contains 5% cashew nut shell liquid (CNSL) and plot #7 is the PG 64-22+5% REOB with no rejuvenating additive. The 5% tall oil pitch has some benefits to retard aging as earlier data in this document has shown, but it is also not as effective as the pure plant sterol or the cholesterol. The CNSL shows improvement over the no treatment option, but it is the poorest performing of all the additives for the RTFO aged binders. The tall oil pitch additive can be seen to perform slightly better than the CNSL blend.

TABLE 19

| Plot # Data for RTFO residue | Log G* at phase angle = 45° | G* @ 45° phase angle, Pascals | phase angle at Log G* = 6 (1 MPa) |
|---|---|---|---|
| #1-5% sterol no REOB | 7.66 | 4.57E+07 | 67.668 |
| #2-8% REOB, 5% cholesterol | 7.54 | 3.47E+07 | 66.6 |
| #3-64-22 only, no additive | 7.529 | 3.38E+07 | 65.4 |
| #4-8% REOB, 5% plant sterol | 7.467 | 2.93E+07 | 64.4 |
| #5-8% REOB, 5% CNSL | 7.469 | 2.94E+07 | 63.5 |
| #6-8% REOB, 5% Tall oil pitch | 7.405 | 2.54E+07 | 64.0 |
| #7-8% REOB only | 7.275 | 1.88E+07 | 60.3 |

Table 20 shows 20 hour PAV data taken from the Black Space plots in FIG. 16. Table 21 shows 60 hour PAV data taken from the Black Space plots in FIG. 17.

TABLE 20

| Plot # Base binder for blends was PG 64-22, all 20 hr. PAV aged | Log G* at phase angle = 45° | G* @ 45° phase angle, Pascals | phase angle at Log G* = 6 (1 MPa) |
|---|---|---|---|
| #1-5% sterol no REOB | 7.36 | 2.29E+07 | 62.53 |
| #2-8% REOB, 5% cholesterol | 7.19 | 1.55E+07 | 59.9 |
| #3-64-22 only, no additive | 7.11 | 1.29E+07 | 58.7 |
| #4-8% REOB, 5% plant sterol | 7.13 | 1.35E+07 | 58.5 |

TABLE 20-continued

| Plot # Base binder for blends was PG 64-22, all 20 hr. PAV aged | Log G* at phase angle = 45° | G* @ 45° phase angle, Pascals | phase angle at Log G* = 6 (1 MPa) |
|---|---|---|---|
| #5-8% REOB, 5% CNSL | 6.78 | 6.03E+06 | 54.3 |
| #6-8% REOB, 5% Tall oil pitch | 6.89 | 7.76E+06 | 55.9 |
| #7-8% REOB only | 6.73 | 5.37E+06 | 53.1 |

TABLE 21

| Plot #--all data 60 hour PAV | Log G* at phase angle = 45° | G* @ 45° phase angle, Pascals | phase angle at Log G* = 6 (1 MPa) |
|---|---|---|---|
| #1-5% sterol no REOB | 6.91 | 8.13E+06 | 56.2 |
| #2-7.5% plant sterol, 8% REOB | 6.75 | 5.62E+06 | 53.7 |
| #3-5% Cholesterol, 8% REOB | 6.72 | 5.25E+06 | 53.4 |
| #4-no sterol no REOB | 6.51 | 3.24E+06 | 50.5 |
| #5-5% plant sterol, 8% REOB | 6.59 | 3.89E+06 | 51.7 |
| #6-2.5% plant sterol, 8% REOB | 6.41 | 2.57E+06 | 49.2 |
| #7-5% CNSL, 8% REOB | 5.81 | 6.46E+05 | 43.02 |
| #8-5% Tall Oil Pitch, 8% REOB Ψ | 6.106 | 1.28E+06 | 45.05 |
| #9-REOB only Ψ | 5.875 | 7.50E+05 | 42.55 |

The 60 hour data for samples #8 and #9 were estimated from the RTFO, 20 and 40 hour PAV data for those samples, the data was not directly measured.

Scanning the data in Tables 19 through 21 shows that the phase angle when the binder stiffness is 1 MPa is continually decreasing as the binder ages. This shows that the binder is becoming more brittle.

FIG. 17 shows a Black Space plot of the 60 hour PAV residues for several samples discussed above plus some others. There are seven sample plots in FIG. 17 and there is data in Table 21 for each sample showing the complex modulus (G*) at a 45° phase angle and showing the phase angle for each sample at G* stiffness of 1 MPa. The sample for plot #1 is only 5% plant sterol and no REOB, which has the best Black Space plot. Plots #2 and #3 are nearly identical for 7.5% plant sterol and 5% cholesterol with 8% REOB. The next data is grouped closely, but the 5% plant sterol with 8% REOB has better properties than the control sample of the PG 64-22, which contained no REOB or rejuvenating additive. The 2.5% plant sterol blend with 8% REOB had worse properties than the control sample and the 5% CNSL sample with 8% REOB had a much lower Black Space plot than any of the other blends. The main conclusions from this evaluation is that 5% cholesterol can be as effective as 7.5% plant sterol and the benefit of cashew nut shell liquid (CNSL) is substantially diminished with extended aging. The Black Space results in FIGS. 15 through 17 coupled with the data extracted from those Figures and shown in Tables 19 through 21 support the ΔTc data and conclusions drawn for the CNSL and cholesterol shown in FIG. 14.

FIGS. 18 and 19 are bar charts summarizing the data in Tables 19 through 21. FIG. 18 shows the decrease in binder stiffness at a constant phase angle of 45° for the different additives as the binders are aged. FIG. 19 shows the decrease in phase angle at a constant modulus of 1 MPa as the binders are aged.

EXAMPLE 10

Sterols were investigated to determine if they could retard aging when bio derived oils had been combined with 20% levels of binder extracted from post-consumer waste shingles.

The binders evaluated in this study were PG 52-34 binder and PG 52-34 plus the sterol (which did not significantly alter either the high or low temperature grade, based on the standard 20 hour PAV aging procedure) and compared the impact of PG 58-28 containing two bio derived oils, Cargill's 1103 and Arizona Chemical's RS1100 added to the PG 58-28 to produce a PG-34 binder (a blend of 2.5% Cargill 1103 plus the 5% of the blended sterol additive).

While the high temperature grade of some of these samples did not meet a PG 52, the low temperature PG grade is significantly more important mixture performance that undergoes long term aging in the field and was studied.

Each of the binders listed in Table 22 was used to produce a sample that would meet Wisconsin specification suitable for a 3 million ESAL pavement. Each of these samples contain 5% RAS, which based on the binder content in the RAS contributed 19.4% of the total 5.7% binder needed to produce the samples. The samples that were produced were subjected to several different aging procedures prior to extracting and recovering the binder from the samples and performing PG grading of the aged materials. The binders were extracted with toluene using a centrifugal extractor and recovered using ASTM D 7906 using a rotary evaporator.

The aging procedures for the samples produced with each of the binders are summarized below.

1. Two hours of loose mix aging at 135° C. followed by extraction and recovery.
2. The binder recovered from the 2 hour loose mix, 135° C. aged samples were subjected to 20 hours of PAV aging following ASTM D6521.
3. The binder recovered from the 2 hour loose mix, 135° C. aged samples were subjected to a second 20 hours of PAV aging following ASTM D652.1
4. The mixtures produced were subjected to 12 hours of loose mix aging in a forced draft oven followed by extraction and recovery using D7906.
5. The mixtures produced were subjected to 24 hours of loose mix aging in a forced draft oven followed by extraction and recovery using D7906.
6. The mixtures aged for 2 hours at 135° C. were compacted to a target air voids level of 7% in a gyratory compactor to form cylindrical specimens according to ASTM D6925 and specimens so produced were aged for 10 days and 20 days at 85° C. in a forced draft oven. After the aging time the specimens were broken apart and the binder extracted and recovered using procedures identified above.

All recovered binders were tested for high temperature PG properties using ASTM D7175 and the low temperature properties were tested and evaluated using the 4 mm DSR procedures developed by Sui, Farrar et. al.

TABLE 22

| MIX # | Base Binder Blend use to produce RAS mixtures | High Temp PG (Unaged) Temp where stiffness = 1 kPa | Low Temp PG 20 hr. PAV | Low Temp PG 40 hr. PAV | ΔTc of 20 hr. PAV | ΔTc of 40 hr. PAV residue |
|---|---|---|---|---|---|---|
| Mix #1 | PG 52-34 | 54 | −35.3 | −32.2 | 0.5 | −1.9 |
| Mix #2 | PG 52-34 + 5% Sterol | 52.7 | −34.2 | −32.7 | 0.56 | 0.61 |
| Mix #3 | PG 52-34 + 5% Sterol, 2.5% Cargill 1103 | 48.3 | −36.5 | −35.6 | 1.6 | 0.4 |
| Mix #4 | PG 58-28 | 59.6 | −29.7 | −25.1 | −0.2 | −3.1 |
| Mix #5 | PG 58-28 + 5% Cargill 1103 | 51.2 | −36.5 | −33.3 | −0.4 | −1.5 |
| Mix #6 | PG 58-28 + 5% AZ Chemical RS1100 | 49.3 | −36.2 | −33.1 | 0.6 | −0.5 |

The data in Table 22 is intended to show that all of the binders investigated, with the exception of the PG 58-28, meet a PG-34 grade at the low temperature. The PAV aged ΔTc data also shows that none of the binders exhibited serious aging even after 40 hours of PAV aging.

Table 23 shows the properties of the binders recovered from the 2 hour, 135° C. aged loose mix.

TABLE 23

| MIX # | Recovered binder from 10 day, 85° C. aged compacted mix, all mixes contained 5% RAS | High-temp PG grade, Temp = 2.2 kPa | Low temp PG grade | ΔTc | R-Value | CI |
|---|---|---|---|---|---|---|
| Mix #1 | PG 52-34 | 66.8 | −37.2 | 0.65 | 2.34 | 2.555 |
| Mix #2 | PG 52-34 + 5% Sterol | 63.0 | −36.76 | 1.4 | 2.12 | 2.614 |
| Mix #3 | PG 52-34 + 5% Sterol & 2.5% Cargill 1103 | 60.4 | −36.12 | 1.4 | 2.13 | 2.546 |
| Mix #4 | PG 58-28 | 73.7 | −31.8 | 0.11 | 2.43 | 2.61 |
| Mix #5 | PG 58-28 + 5% Cargill 1103 | 65.9 | −38.7 | 0.28 | 2.43 | 2.704 |
| Mix #6 | PG 58-28 + 5% AZ Chemical RS1100 | 66.5 | −38.2 | 1.8 | 2.38 | 2.546 |

Table 24 shows the properties of the binders recovered from the 2 hour, 135° C. aged loose mix followed by 20 hour PAV aging.

TABLE 24

| MIX # | Recovered binder from 10 day, 85° C. aged compacted mix, all mixes contained 5% RAS | High-temp PG grade, Temp = 2.2 kPa | Low temp PG grade | ΔTc | R-Value | CI |
|---|---|---|---|---|---|---|
| Mix #1 | PG 52-34 | 77.4 | −32.75 | −2.57 | 2.89 | 2.112 |
| Mix #2 | PG 52-34 + 5% Sterol | 77.2 | −33.48 | −0.7 | 2.47 | 2.319 |
| Mix #3 | PG 52-34 + 5% Sterol & 2.5% Cargill 1103 | 71.1 | −36.24 | −0.21 | 2.47 | 2.367 |
| Mix #4 | PG 58-28 | 82.6 | −27.5 | −3.48 | 2.88 | 2.161 |
| Mix #5 | PG 58-28 + 5% Cargill 1103 | 78.1 | −32.6 | −3.12 | 2.9 | 2.096 |
| Mix #6 | PG 58-28 + 5% AZ Chemical RS1100 | 77.7 | −33.1 | −1.56 | 2.73 | 2.115 |

Table 25 shows the properties of the binders recovered from the 2 hour, 135° C. aged loose mix followed by 40 hour PAV aging.

TABLE 25

| MIX # | Recovered binder from 10 day, 85° C. aged compacted mix, all mixes contained 5% RAS | High-temp PG grade, Temp = 2.2 kPa | Low temp PG grade | ΔTc | R-Value | CI |
|---|---|---|---|---|---|---|
| MIX #1 | PG 52-34 | 86.2 | −28.6 | −3.89 | 3.32 | 1.717 |
| MIX #2 | PG 52-34 + 5% Sterol | 80.8 | −30.1 | −2.31 | 2.84 | 1.882 |
| MIX #3 | PG 52-34 + 5% Sterol & 2.5% Cargill 1103 | 77.2 | −32.9 | −2.13 | 2.75 | 1.889 |
| MIX #4 | PG 58-28 | 90.9 | −23.1 | −4.7 | 3.31 | 1.775 |
| MIX #5 | PG 58-28 + 5% Cargill 1103 | 85.5 | −28.5 | −4.77 | 3.23 | 1.868 |
| MIX #6 | PG 58-28 + 5% AZ Chemical RS1100 | 86.8 | −27.7 | −5.63 | 3.07 | 1.713 |

Table 26 shows the properties of the binders recovered from the 12 hour, 135° C. aged loose mix.

TABLE 26

| MIX # | Recovered binder from 10 day, 85° C. aged compacted mix, all mixes contained 5% RAS | High-temp PG grade, Temp = 2.2 kPa | Low temp PG grade | ΔTc | R-Value | CI |
|---|---|---|---|---|---|---|
| Mix #1 | PG 52-34 | 85.60 | −31.13 | −2.78 | 3.17 | 1.781 |
| Mix #2 | PG 52-34 + 5% Sterol | 80.90 | −30.99 | −1.84 | 2.76 | 1.997 |
| Mix #3 | PG 52-34 + 5% Sterol & 2.5% Cargill 1103 | 79.70 | −33.60 | −1.93 | 2.86 | 2.003 |
| Mix #4 | PG 58-28 | 93.40 | −23.97 | −5.13 | 3.24 | 1.737 |
| Mix #5 | PG 58-28 + 5% Cargill 1103 | 90.20 | −29.26 | −4.06 | 3.36 | 1.825 |
| Mix #6 | PG 58-28 + 5% AZ Chemical RS1100 | 94.40 | −26.18 | −5.33 | 3.38 | 1.669 |

Table 27 shows the properties of the binders recovered from the 24 hour, 135° C. aged loose mix.

TABLE 27

| MIX # | Recovered binder from 10 day, 85° C. aged compacted mix, all mixes contained 5% RAS | High-temp PG grade, Temp = 2.2 kPa | Low temp PG grade | ΔTc | R-Value | CI |
|---|---|---|---|---|---|---|
| MIX #1 | PG 52-34 | 114.3 | −20.08 | −12.09 | 4.03 | 1.375 |
| MIX #2 | PG 52-34 + 5% Sterol | 99.8 | −23.97 | −7.36 | 3.71 | 1.542 |
| MIX #3 | PG 52-34 + 5% Sterol & 2.5% Cargill 1103 | 98.7 | −25.66 | −5.75 | 3.56 | 1.563 |
| MIX #4 | PG 58-28 | 115.9 | −12.42 | −13.11 | 4.31 | 1.406 |
| MIX #5 | PG 58-28 + 5% Cargill 1103 | 118.9 | −14.77 | −14.77 | 4.56 | 1.387 |
| MIX #6 | PG 58-28 + 5% AZ Chemical RS1100 | 123.1 | −12.16 | −15.61 | 4.60 | 1.270 |

Table 28 shows the properties of the binders recovered from the 10 day, 85° C. aged compacted mix samples.

TABLE 28

| MIX # | Recovered binder from 10 day, 85° C. aged compacted mix, all mixes contained 5% RAS | High-temp PG grade, Temp = 2.2 kPa | Low temp PG grade | ΔTc | R-Value | CI |
|---|---|---|---|---|---|---|
| Mix #1 | PG 52-34 | 77.9 | −32.68 | −1.75 | 2.83 | 2.145 |
| Mix #2 | PG 52-34 + 5% Sterol | 75.4 | −32.53 | −0.67 | 2.54 | 2.265 |
| Mix #3 | PG 52-34 + 5% Sterol & 2.5% Cargill 1103 | 71.7 | −36.18 | −0.79 | 2.47 | 2.250 |
| Mix #4 | PG 58-28 | 86.6 | −25.74 | −3.78 | 3.00 | 2.064 |
| Mix #5 | PG 58-28 + 5% Cargill 1103 | 79.4 | −31.42 | −2.48 | 2.81 | 2.099 |
| Mix #6 | PG 58-28 + 5% AZ Chemical RS1100 | 83.4 | −28.18 | −3.25 | 2.92 | 1.910 |

Table 29 shows the properties of the binders recovered from the 20 day, 85° C. aged compacted mix samples.

TABLE 29

| MIX # | Recovered binder from 10 day, 85° C. aged compacted mix, all mixes contained 5% RAS | High-temp PG grade, Temp = 2.2 kPa | Low temp PG grade | ΔTc | R-Value | CI |
|---|---|---|---|---|---|---|
| MIX #1 | PG 52-34 | 85.4 | −29.12 | −3.78 | 3.18 | 1.755 |
| MIX #2 | PG 52-34 + 5% Sterol | 82.1 | −29.85 | −2.81 | 2.83 | 1.913 |
| MIX #3 | PG 52-34 + 5% Sterol & 2.5% Cargill 1103 | 80.6 | −30.44 | −2.59 | 2.81 | 1.876 |
| MIX #4 | PG 58-28 | 94.90 | −20.41 | −7.36 | 3.36 | 1.778 |
| MIX #5 | PG 58-28 + 5% Cargill 1103 | 88.9 | −26.30 | −5.03 | 3.23 | 1.722 |
| MIX #6 | PG 58-28 + 5% AZ Chemical RS1100 | 94 | −20.63 | −8.56 | 3.39 | 1.577 |

Impact of binder aging on high temperature PG grade of the recovered binders and trends in the high temperature PG grade related to sterol and bio derived oils:

1. For Tables 23 through 29 the binders recovered from Mixes #2 and #3 (the samples produced with binders containing sterol) have the lowest high temperature PG grade compared to other binders. This indicates less susceptibility to the aging process described in each Table due to the presence of sterol.
2. Mixes #5 and #6 (containing 5% of bio derived oils) had the lowest high temperature PG grade after initial blending (Table 22), but as the data and FIG. 20 show after the 2 hour 135° C. aging step their high temperature PG grade was already greater than Mixes 1, 2 and 3. The recovered binder from these mixtures had high temperature properties comparable to those of Mix #4 (PG 58-28 with no bio oil additive) for the 12 and 24 hour, 135° C. loose mix aged recovered binder (Tables 26 and 27) and for the 10 and 20 day, 85° C. aged recovered binders (Tables 28 and 29). After 20 and 40 hours of PAV aging of the binder recovered from the 2 hour, 135° C. aged mixture the binders containing the bio derived oils had high temperature properties lower than the original PG 58-28. This relationship did not continue as more severe aging of the mixtures occurred. These high temperature trends are also easily observed in FIG. 17.

Trends in the low temperature PG grade related to sterol and bio derived oils:

1. The low temperature PG grade of the binders recovered from the 2 hour, 135° C. aged loose mix shows that the blends of PG 58-28 plus 5% bio derived oil (Mixes #5 and #6) had the best low temperature properties (Table 23); however after aging the recovered binder in the 20 and 40 hour PAV the binders for Mixes #2 and #3 had the best low temperature properties.
2. After the 12 hour loose mix aging procedure Mix #1 had a slightly colder low temperature grade than Mix #2, however after the 24 hour loose mix aging procedure Mixes #2 and #3 had the best low temperature grade values. After the 10 and 20 day, 85° C. compacted mix conditioning Mixes #2 and #3 had the coldest low temperature grades although Mix #1 and Mix #2 were essentially the same after the 10 day aging step. FIG. 21 shows all of these results in one plot.
3. Binder recovered from Mix #3, containing sterol and 2.5% Cargill 1103 bio oil, had after 20 days of 85° C. compacted mix aging (Table 29) the best low temperature recovered binder properties of all mixes. Mix #2, containing 5% sterol, had after 10 days of 85° C. aging (Table 28) recovered binder low temperature PG grade properties similar to the PG 52-34 recovered binder and properties colder than the blends produced with 5% bio derived oil (Mixes #5 & #6).

Trends in the ΔTc and R-Value properties of the aged, recovered binders related to sterol and bio derived oils. To avoid confusion note that warmer ΔTc values are indicative of a binder with less detrimental aging which favors long term pavement performance. The ΔTc results are plotted in FIG. 22.

1. For the 2 hour 135° C. conditioning step all ΔTc values were positive and Mix #6 had the highest value.
2. For any of the subsequent mix aging conditions the recovered binder ΔTc values for the Mixes containing sterol (Mixes #2 & #3) were always the least negative.

3. When comparing the ΔTc properties of Mixes #2 & #3 for similar types of aging Mix #3 always has least negative ΔTc properties for the recovered binder from the mix with greater aging. This comparison is more easily visualized in FIG. 22
4. After PAV aging the binder recovered from the 2 hour, 135° C. aged loose mix for 40 hours the binders recovered from Mixes #5 and #6 had ΔTc properties similar to the ΔTc of the PG 58-28 that did not contain either of the bio derived oils used in the binders for Mixes #5 and #6. See FIG. 22
5. Binders recovered from the 12 and 24 hour, 135° C. aged loose mix from Mixes #5 and #6 had ΔTc properties similar to the ΔTc of the PG 58-28 that did not contain either of the bio derived oils used in the binders for Mixes #5 and #6. See FIG. 19
6. Binders recovered from the 10 and 20 day, 85° C. aged, compacted mix for Mixes #5 and #6 had ΔTc properties similar to the ΔTc of the PG 58-28 that did not contain either of the bio derived oils used in the binders for Mixes #5 and #6. See FIG. 19
7. Similar data trends can be seen in FIG. 23 which is a plot of R-Value for these blends. R-Value or Rheological Index is a measure of the relaxation properties of a binder. Lower R-Values indicate a binder with better relaxation characteristics. Values of 3 are generally indicative of a binder that has aged to a point where fatigue cracking could be a problem. FIG. 23 shows that only Mixes #2 and #3 are able to maintain a value below 3 with the exception of the 24 hour 135° C. loose mix aging procedure and at that aging condition they still maintain the lowest R-Values.

Trends in Colloidal Index properties of properties of the aged, recovered binders related to sterol and bio derived oils. The colloidal index is an indicator of compositional changes in a binder as it ages. As binder ages its Colloidal Index (CI) decreases due to increases in asphaltenes and reduction in cyclics primarily. FIG. 24 is a plot of the colloidal index for the different aging conditions of the binder blends being investigated. FIG. 24 shows that all the binders recovered after 2 hours of aging 135° C. had CI values greater than 2.5, which is a very good value. As with the other parameters discussed once aging commences the detrimental impact of aging begins to manifest itself. As aging becomes more severe the general trend for all the binders is a decrease in CI, but for all of the aging steps the sterol containing blends, Mixes #2 and #3 exhibit the highest values. As with other parameters discussed the blends containing bio derived oil additives have CI values similar to the base PG 58-28. However the 40 hour PAV residue samples Mix #5 has a CI value similar to those of Mixes #2 and #3.

1. The CI values for the 12 & 24 hour, 135° C. loose mix aged samples recovered binder and the 10 & 20 day, 85° C. aged compacted mix samples recovered binder to show the binders for the sterol containing mixes (MIX #2 and MIX #3) to have the highest values. The CI values for the Cargill 1103 containing mixes (MIX #5) are a slightly higher than those for the Arizona Chemical RS1100 containing mixes (MIX #6) and CI's for both of those mixtures are similar to the CI for the PG 58-28 mix with no bio oil additive (MIX #4).

See FIG. 24 for a composite summary graph of the Colloidal Index data for all the aged, recovered binders.

The results above show that the addition of sterol to a binder used to produce a mixture containing high level of reclaimed binder can retard the impact of mixture or binder aging. It is important that the short term oven aged (2 hour, 135° C.) recovered binder when aged for 20 and 40 hours showed that the sterol blends maintained the best Colloidal Index values as well as the warmest ΔTc values. It is also important that the sterol containing mixtures when aged loose at 135° C. and aged compacted at 85° C. had recovered binders that also maintained the best Colloidal Index and ΔTc properties compared to the other mixtures. This demonstrates that the impact of the sterol is not an artifact of how the aging occurs, that is in the PAV or on aggregate; the aging procedure, loose or compacted mix or in an asphalt film; or specific temperature, 100° C. PAV, 85° C. compacted mix or 135° C. loose mix. The aging rates may be affected by these factors, but for a given set of aging criteria the impact on the materials investigate is always the same.

The results above also show that the blending of bio derived oils into binders so that those binders can be used to produce mixtures with high levels of reclaimed binder does not appear to result in retarding the subsequent aging of those blended binders back to a condition approaching that of the original binder into which the bio derived oils had been added. This is not rejuvenation or aging retardation but rather simple softening of the overall mix and does not appear to be sustainable.

The addition of sterol shows that it does not soften the binder more than 1 or 2° C. at either high or low temperature. However as the data for MIX #2 and MIX #3 demonstrate the presence of the sterol performs the function of retarding the destructive effects of aging. The sterol does not prevent binder aging but it does alter the rate of aging and based on the MIX #3 data does preserve the reduced stiffening benefits of low levels of bio derived oil without the reversal of properties as a consequence of extended aging.

Some additional non-limiting embodiments are provided below to further exemplify the present disclosure:

1. An asphalt binder paving comprising aggregate, virgin asphalt binder, reclaimed asphalt binder material comprising reclaimed asphalt pavement (RAP), reclaimed asphalt shingles (RAS) or combinations of both, a triterpenoid, and a softening agent, wherein the triterpenoid is free of cyclic organic compositions that contain esters or ester blends, and a sterol content in the rage of 0.5 to 15 wt. % of the virgin asphalt binder.
2. An asphalt binder comprising virgin asphalt binder, reclaimed asphalt binder material comprising reclaimed asphalt pavement (RAP), reclaimed asphalt shingles (RAS) or combinations of both, a triterpenoid, and a softening agent, wherein the triterpenoid is free of cyclic organic compositions that contain esters or ester blends, and a sterol content is within the rage of 0.5 to 15 wt. % of the virgin asphalt binder.
3. A method for retarding oxidative aging of the asphalt binder, which method comprises adding one of more triterpenoid or a triterpenoid blends to a bituminous or asphalt binder composition, wherein the triterpenoid or triterpenoid blend does not contain an ester or an ester blend, and wherein the triterpenoid or triterpenoid blend is used in the composition in a range of 0.5 to 15 wt. %, wherein the triterpenoid additive is present within the range of 1 to 10 wt. %, or within the range of 1 to 3 wt. % of the virgin asphalt binder.
4. A method for reusing reclaimed asphalt binder for asphalt pavement production, which method comprises the use of a triterpenoid or a triterpenoid blend as an additive to bituminous or asphalt binder mixture without the use of an ester or an ester blend, and wherein the triterpenoid additive is present within the range of 0.5 to 15 wt. %, 1 to 10 wt. %, or 1 to 3 wt. % of the virgin asphalt binder.

5. A method for applying a road pavement surface which method incorporates the use of asphalt binder of any of the preceding embodiments, wherein the asphalt binder composition of any of the preceding embodiments are prepared, mixed, applied to a base surface, and compacted.
6. The composition and methods of any of the preceding embodiments wherein the triterpenoid is a sterol.
7. The composition and methods of any of the preceding embodiments wherein the triterpenoid is a stanol.
8. The composition and methods of any of the preceding embodiments wherein the triterpenoid is a plant sterol.
9. The composition and methods of any of the preceding embodiments wherein the triterpenoid is a plant stanol.
10. The composition and methods of any of the preceding embodiments wherein the reclaimed asphalt binder material is RAP.
11. The composition and methods of any of the preceding embodiments wherein the reclaimed asphalt binder material is RAS.
12. The composition and methods of any of the preceding embodiments wherein sterol content is in a range of 1 to 15 wt. % of the virgin asphalt binder.
13. The composition and methods of any of the preceding embodiments wherein the asphalt binder compositions comprising reclaimed asphalt shingles (RAS) at a binder replacement level 1% and greater.
14. The composition and methods of any of the preceding embodiments wherein the asphalt binder compositions comprising reclaimed asphalt pavement (RAP) at binder replacement levels 10% and greater or 20% and greater.
15. The composition and methods of any of the preceding embodiments wherein the asphalt binder comprising reclaimed asphalt pavement (RAP) and reclaimed asphalt shingles (RAS) used in combination at RAP binder replacement levels of 10% and greater and RAS binder replacement levels of 1% and greater.
16. The composition and methods of any of the preceding embodiments wherein the asphalt binder comprising asphalt binder extracted and recovered from post-consumer waste shingles at levels of 1% and greater or 5% by weight and greater.
17. The composition and methods of any of the preceding embodiments wherein the asphalt binder comprising asphalt binder extracted from manufacture's waste shingles at levels of 1%, 2% or 5% by weight and greater.
18. The composition and methods of any of the preceding embodiments wherein the asphalt binder comprising oxidized asphalt binders meeting ASTM specification D312 for Type II, Type III, Type IV and coating asphalt binder at levels of 1% or greater, or 5% by weight and greater.
19. The composition and methods of any of the preceding embodiments wherein the asphalt binder comprising extracted and recovered RAP at levels of 10% by weight and greater.
20. The composition and methods of any of the preceding embodiments wherein the asphalt binder comprising re-refined engine oil bottoms at levels of 3% and higher by weight or volume percent.
21. The composition and methods of any of the preceding embodiments wherein the asphalt binder comprising paraffinic oils at levels of 1% and higher by weight or volume percent.
22. The composition and methods of any of the preceding embodiments wherein the asphalt binder paving comprising re-refined engine oil bottoms at levels of 1% and higher by weight or volume percent.
23. The composition and methods of any of the preceding embodiments wherein the asphalt binder paving comprising paraffinic oils at levels of 1% and higher by weight or volume percent.
24. An asphalt binder paving comprising aggregate, virgin asphalt binder, reclaimed asphalt binder material comprising reclaimed asphalt pavement (RAP), reclaimed asphalt shingles (RAS) or combinations of both, a triterpenoid, and a softening agent, wherein the triterpenoid is free of cyclic organic compositions that contain esters or ester blends, and a sterol content in the rage of 0.5 to 15 wt. % of the virgin asphalt binder.
25. An asphalt binder composition comprising virgin asphalt binder, reclaimed asphalt binder material comprising reclaimed asphalt pavement (RAP), reclaimed asphalt shingles (RAS) or combinations of both, a triterpenoid, and a softening agent, wherein the triterpenoid is free of cyclic organic compositions that contain esters or ester blends, and a sterol content is within the rage of 0.5 to 15 wt. % of the virgin asphalt binder.
26. A method for retarding oxidative aging of the asphalt binder, which method comprises adding one of more triterpenoid or a triterpenoid blends to a bituminous or asphalt binder, wherein the triterpenoid or triterpenoid blend does not contain an ester or an ester blend, and wherein the triterpenoid or triterpenoid blend is used in the composition in a range of 0.5 to 15 wt. %, wherein the triterpenoid additive is present within the range of 1 to 10 wt. %, or within the range of 1 to 3 wt. % of the virgin asphalt binder.
27. A method for reusing reclaimed asphalt binder for asphalt binder pavement production, which method comprises the use of a triterpenoid or a triterpenoid blend as an additive to bituminous or asphalt binder mixture without the use of an ester or an ester blend, and wherein the triterpenoid additive is present within the range of 0.5 to 15 wt. %, 1 to 10 wt. %, or 1 to 3 wt. % of the virgin asphalt binder.
28. A method for applying a road pavement surface which method incorporates the use of asphalt binder composition of any of the preceding embodiments, wherein the asphalt binder of any of the preceding embodiments are prepared, mixed, applied to a base surface, and compacted.
29. The composition and methods of any of the preceding embodiments wherein the triterpenoid is a sterol.
30. The composition and methods of any of the preceding embodiments wherein the triterpenoid is a stanol.
31. The composition and methods of any of the preceding embodiments wherein the triterpenoid is a plant sterol.
32. The composition and methods of any of the preceding embodiments wherein the triterpenoid is a plant stanol.
33. The composition and methods of any of the preceding embodiments wherein the reclaimed asphalt binder material is RAP.
34. The composition and methods of any of the preceding embodiments wherein the reclaimed asphalt binder material is RAS.
35. The composition and methods of any of the preceding embodiments wherein sterol content is in a range of 1 to 15 wt. % of the virgin asphalt binder.
36. The composition and methods of any of the preceding embodiments wherein the asphalt binder comprising reclaimed asphalt shingles (RAS) at a binder replacement level 1% and greater.

37. The composition and methods of any of the preceding embodiments wherein the asphalt binder comprising reclaimed asphalt pavement (RAP) at binder replacement levels 20% and greater.
38. The composition and methods of any of the preceding embodiments wherein the asphalt binder comprising reclaimed asphalt pavement (RAP) and reclaimed asphalt shingles (RAS) used in combination at RAP binder replacement levels of 10% and greater and RAS binder replacement levels of 1% and greater.
39. The composition and methods of any of the preceding embodiments wherein the asphalt binder comprising asphalt binder extracted and recovered from post-consumer waste shingles at levels of 1% or greater or 5% by weight and greater.
40. The composition and methods of any of the preceding embodiments wherein the asphalt binder comprising asphalt binder extracted from manufacture's waste shingles at levels of 1% or greater or 5% by weight and greater.
41. The composition and methods of any of the preceding embodiments wherein the asphalt binder comprising oxidized asphalt binders meeting ASTM specification D312 for Type II, Type III, Type IV and coating asphalt binder at levels of 1% or greater or 5% by weight and greater.
42. The composition and methods of any of the preceding embodiments wherein the asphalt binder comprising extracted and recovered RAP at levels of 10% by weight and greater.
43. The composition and methods of any of the preceding embodiments wherein the asphalt binder comprising re-refined engine oil bottoms at levels of 3% and higher by weight or volume percent.
44. The composition and methods of any of the preceding embodiments wherein the asphalt binder comprising paraffinic oils at levels of 1% and higher by weight or volume percent.
45. The composition and methods of any of the preceding embodiments wherein the asphalt binder paving comprising re-refined engine oil bottoms at levels of 1% and higher by weight or volume percent.
46. The composition and methods of any of the preceding embodiments wherein the asphalt binder paving comprising paraffinic oils at levels of 1% and higher by weight or volume percent.

Further additional non-limiting embodiments are provided below to further exemplify the present disclosure:
1. An asphalt binder comprising virgin asphalt binder, reclaimed asphalt binder material comprising reclaimed asphalt pavement (RAP), reclaimed asphalt shingles (RAS) or combinations of both and 0.5 to 15 wt. % of an anti-aging additive based on the virgin asphalt binder.
2. The asphalt binder of embodiment 1, wherein the anti-aging additive is 1 to 10 wt. %, or 1 to 3 wt. % of the virgin asphalt binder.
3. The asphalt binder of embodiment 1, wherein the anti-aging additive comprises a triterpenoid or triterpenoid blend.
4. The asphalt binder of embodiment 3, wherein the triterpenoid comprises a sterol.
5. The asphalt binder of embodiment 3, wherein the triterpenoid comprises a stanol.
6. The asphalt binder composition of embodiment 4, wherein the sterol comprises a plant sterol.
7. The asphalt binder composition of embodiment 5, wherein the stanol comprises a plant stanol.
8. The asphalt binder of embodiment 1, further comprising a softening agent.
9. The asphalt binder of embodiment 8, wherein the softening agent comprises a re-refined engine oil bottoms.
10. The asphalt binder of embodiment 1, further comprising aggregate.
11. The asphalt binder of embodiment 1, wherein the asphalt binder composition provides a $\Delta Tc$ of $-5.0$ or greater.
12. The asphalt binder of embodiment 1, wherein the anti-aging additive is present in an amount effective to provide a less negative $\Delta Tc$ value after aging the asphalt binder compared to a similarly-aged binder without the age retarding additive.
13. A paved surface comprising the asphalt binder composition of embodiment 1.
14. A method for slowing the aging or restoring aged asphalt binder comprising:
    adding an anti-aging additive to an asphalt binder, wherein the asphalt binder comprises a virgin asphalt binder, reclaimed asphalt binder material comprising embodiment asphalt pavement (RAP), embodiment asphalt shingles (RAS) or combinations of both and 0.5 to 15 wt. % of an anti-aging additive based on the virgin asphalt binder.
15. The method of embodiment 14, wherein the anti-aging additive is 1 to 10 wt. %, or 1 to 3 wt. % of the virgin asphalt binder.
16. The method of embodiment 14, wherein the anti-aging additive comprises a triterpenoid.
17. The method of embodiment 16, wherein the triterpenoid comprises a sterol.
18. The method of embodiment 16, wherein the triterpenoid comprises a stanol.
19. The method of embodiment 17, wherein the sterol comprises a plant sterol.
20. The method of embodiment 18, wherein the stanol comprises a plant stanol.
21. A method to identity at least one deleterious component present in an asphalt binder comprising measuring defect areas in an Atomic Force Microscopy image.
22. The method according to embodiment 21, wherein the deleterious component is Re-refined Engine Oil Bottoms.
23. The method according to embodiment 21, wherein the deleterious component is Vacuum Tower Asphalt Extender.
24. The method according to embodiment 21, wherein the deleterious component is any drain oil product or waste engine oil material with or without post-consumer processing.
25. The method according to embodiment 21, wherein the deleterious component is paraffinic processing oil.
26. The method according to embodiment 21, wherein the deleterious component is lubricating base oil.
27. The method according to claim 21, wherein the deleterious component is asphalt binder extracted from a paving mixture containing Reclaimed Asphalt Pavement (RAP) and the RAP is present in an asphalt binder in an amount ranging from 0.1% to 100% of the paving mixture.
28. The method according to claim 21, wherein the deleterious Component is asphalt binder extracted from a paving mixture containing Reclaimed Asphalt Shingles (RAS) and the RAS is present in a binder replacement amount of 0.1% to 50%.
29. The method according to embodiment 21, wherein the deleterious material is asphalt binder extracted from a paving mixture containing Reclaimed Asphalt Pavement (RAP) and Reclaimed Asphalt Shingles (RAS), and wherein a combination of RAP and RAS is present in an asphalt binder in an amount of 0.1% to 100%.

30. The method according to embodiment 21, wherein deleterious material is naturally occurring in an asphalt binder and not resulting from any materials added after the asphalt binder has been produced.

The invention claimed is:

1. A method for slowing the aging rate of aged asphalt binder in a paved surface comprising:
adding a crude sterol comprising at least 13.5 wt. % sterol molecules to an asphalt binder composition, wherein the asphalt binder composition comprises 60 wt. % to about 95 wt. % of a virgin asphalt binder, from about 5 wt. % to about 40 wt. % reclaimed asphalt binder material obtained from aged pavement comprising asphalt pavement (RAP) at binder replacement levels 20% and greater, asphalt shingles (RAS) at a binder replacement level 1% and greater or combinations of both and from 0.5 to 15 wt. % of the crude sterol based on the virgin asphalt binder,
combining the asphalt binder composition with aggregate to provide paving mix, and
applying the paving mix on a base surface to provide the paved surface with slower aging rate.

2. The method of claim 1, wherein the crude sterol is a bio-derived source or distilled residue of the bio-derived source.

3. The method of claim 1 wherein the crude sterol comprises 1 to 10 wt. %, of the virgin asphalt binder.

4. The method of claim 1, wherein the crude sterol comprises 1 to 3 wt. % based on the virgin asphalt binder.

5. The method of claim 1, wherein the crude sterol source comprises a tall oil pitch.

6. The method of claim 1, wherein the crude sterol comprises crude sterol derived from soybean oil.

7. The method of claim 1, wherein the crude sterol source comprises corn oil.

8. The method of claim 1, wherein the crude sterol source comprises cholesterol.

9. The method of claim 1, wherein the reclaimed asphalt binder material comprises a softening agent.

10. The method of claim 9, wherein the softening agent comprises a re-refined engine oil bottoms.

11. The method of claim 1, wherein the asphalt binder provides a ΔTc of greater than or equal to −5.0° C.

12. The method of claim 1, wherein crude sterol comprises an amount effective to provide a less negative ΔTc value after aging the asphalt binder compared to a control aged asphalt binder.

13. A method for reusing reclaimed asphalt binder for asphalt pavement production, comprising:
forming the paving mix of claim 1, and
applying the paving mix on a base surface to provide the asphalt pavement.

14. The method of claim 13, wherein the reclaimed asphalt binder material comprises reclaimed asphalt pavement.

15. The method of claim 13, wherein the reclaimed asphalt binder material comprises reclaimed asphalt shingles.

16. The method of claim 13, further comprising compacting the paving mix applied to the base surface.

* * * * *